US011186643B2

(12) United States Patent
Micklem et al.

(10) Patent No.: US 11,186,643 B2
(45) Date of Patent: *Nov. 30, 2021

(54) ANTI-AXL ANTIBODIES

(71) Applicant: BerGenBio ASA, Bergen (NO)

(72) Inventors: David Robert Micklem, Bergen (NO);
Sergej Kiprijanov, Oslo (NO); Linn Hodneland Nilsson, Bergen (NO);
Lavina Ahmed, Bergen (NO);
Hallvard Haugen, Bergen (NO)

(73) Assignee: BerGenBio ASA, Bergen (NO)

( * ) Notice: Subject to any disclaimer, the term of this patent is extended or adjusted under 35 U.S.C. 154(b) by 496 days.

This patent is subject to a terminal disclaimer.

(21) Appl. No.: 15/958,076

(22) Filed: Apr. 20, 2018

(65) Prior Publication Data

US 2018/0371096 A1 Dec. 27, 2018

Related U.S. Application Data

(63) Continuation of application No. 15/318,028, filed as application No. PCT/EP2015/063700 on Jun. 18, 2015, now Pat. No. 9,975,954.

(30) Foreign Application Priority Data

Jun. 18, 2014 (GB) .................................... 1410826

(51) Int. Cl.
| C07K 16/28 | (2006.01) |
| C07K 16/30 | (2006.01) |
| G01N 33/574 | (2006.01) |
| A61K 45/06 | (2006.01) |
| A61K 47/68 | (2017.01) |
| A61K 38/05 | (2006.01) |
| A61K 39/395 | (2006.01) |

(52) U.S. Cl.
CPC .......... *C07K 16/2863* (2013.01); *A61K 38/05* (2013.01); *A61K 39/39558* (2013.01); *A61K 45/06* (2013.01); *A61K 47/6817* (2017.08); *A61K 47/6849* (2017.08); *A61K 47/6851* (2017.08); *A61K 47/6867* (2017.08); *C07K 16/3061* (2013.01); *G01N 33/57426* (2013.01); *G01N 33/57484* (2013.01); *G01N 33/57492* (2013.01); *C07K 2317/24* (2013.01); *C07K 2317/33* (2013.01); *C07K 2317/52* (2013.01); *C07K 2317/56* (2013.01); *C07K 2317/565* (2013.01); *C07K 2317/622* (2013.01); *C07K 2317/73* (2013.01); *C07K 2317/75* (2013.01); *C07K 2317/77* (2013.01); *C07K 2317/92* (2013.01); *G01N 2333/71* (2013.01)

(58) Field of Classification Search
CPC .... C07K 16/28; C07K 16/30; C07K 16/2863; A61K 39/395–39558
See application file for complete search history.

(56) References Cited

U.S. PATENT DOCUMENTS

| 6,884,879 | B1 * | 4/2005 | Baca ...................... C07K 16/22 |
| | | | 435/320.1 |
| 9,975,954 | B2 * | 5/2018 | Micklem .......... G01N 33/57426 |
| 10,544,223 | B2 * | 1/2020 | Van Berkel .......... A61K 31/138 |
| 2010/0330095 | A1 | 12/2010 | Hettmann et al. |
| 2013/0243753 | A1 | 9/2013 | Pei et al. |
| 2017/0107290 | A1 | 4/2017 | Micklem et al. |
| 2017/0349658 | A1 | 12/2017 | Micklem et al. |
| 2019/0352407 | A1 * | 11/2019 | Van Berkel ........ C07K 16/2863 |

FOREIGN PATENT DOCUMENTS

| EP | 2228392 A1 | 9/2010 |
| EP | 2431393 A1 | 3/2012 |
| EP | 2589609 A1 | 5/2013 |
| WO | 2011014457 A1 | 2/2011 |
| WO | 2011159980 A1 | 12/2011 |
| WO | 2012175691 A1 | 12/2012 |
| WO | 2012175692 A1 | 12/2012 |
| WO | WO-2016166296 A2 * | 10/2016 | ......... C07K 16/2863 |

OTHER PUBLICATIONS

Almagro & Fransson, Frontiers in Bioscience; 13:1619-33 (Year: 2008).*
Bowers et al., J Biol Chem 288:7688-96 (Year: 2013).*
"Mus Musculus Isolate 26 Immunoglobulin V Kappa Light Chain mRNA, Partial CDS," NCBI Accession No. GU563184; 1 page, 2010.
International Preliminary Report on Patentability and Written Opinion issued in PCT/EP20105/063700, dated Dec. 20, 2016; 8 pages.
International Preliminary Report on Patentability and Written Opinion issued in PCT/EP2015/063704, dated Dec. 20, 2016, 8 pages.
Rudikoff et al., "Somatic Diversification of Immunoglobulins," Proc. Natl. Acad. Sci USA, vol. 81, pp. 2162-2166; Apr. 1984.
UKIPO Search Report issued in corresponding GB1410825.2 dated Mar. 17, 2015; 5 pages.
UKIPO Search Report issued in corresponding GB1410826.0 dated Mar. 30, 2015; 6 pages.
Ye et al., "An Anti-Axl Monocolnal Antibody Attenuates Xenograft Tumor Growth and Enhances the Effect of Multiple Anticancer Therapies," Oncogene 29, pp. 5254-5264; 2010.
International Search Report and Written Opinion issued in corresponding PCT Application No. PCT/EP2015/063700, dated Dec. 8, 2015, 14 pages.

(Continued)

*Primary Examiner* — Jessica H Roark
(74) *Attorney, Agent, or Firm* — McNeill Baur PLLC

(57) ABSTRACT

Antibodies which specifically bind to the Axl protein are described. Also disclosed are methods for the production and use of the anti-Axl antibodies.

16 Claims, 17 Drawing Sheets

Specification includes a Sequence Listing.

(56) References Cited

OTHER PUBLICATIONS

Leconet et al., "Preclinical validation of AXL receptor as a target for antibody-based pancreatic cancer immunotherapy," Oncogene (2014) 33, 5405-5414.
Ben-Batalla et al., "Axl, a prognostic and therapeutic target in acute myeloid leukemia mediates paracrine crosstalk of leukemia cells with bone marrow stroma," Blood, Oct. 3, 2013, 122(14):2443-2452.

* cited by examiner

VH5 C9-3

EVKLVESGGDLVKPGGSLKLSCAASGFTFSSYGMSWVRQTPDKRLEWVATISSGGSYTYY
PDSVKGRFTISRDNAKNTLYLQMSSLKSEDTAMYYCARHPIYYTYDDTMDYWGQGTSVTV
SS

Vκ4 G4-1

DIVLTQSPAIMAASPGEKVTMTCSASSSVSSGNFHWYQQKPGTSPKLWIYRTSNLASGVPA
RFSGSGSGTSYSLTISSMEAEDAATYYCQQWSGYPWTFGGGTKLEIK

FIGURE 8

ANTI-AXL ANTIBODIES

This application is a continuation of U.S. application Ser. No. 15/318,028, filed Dec. 12, 2016, which is a national phase entry pursuant to 35 U.S.C. § 371 of International Application No. PCT/EP2015/063700, filed Jun. 18, 2015, which claims the benefit of priority of Great Britain Application No. 1410826.0, filed Jun. 18, 2014, each of which is incorporated by reference herein in its entirety for any purpose.

The present disclosure relates to antibodies which specifically bind to the Axl protein. Also disclosed are methods for the production and use of the anti-Axl antibodies.

BACKGROUND

Axl is a member of the TAM (Tyro3-Axl-Mer) receptor tyrosine kinases (RTK) that share the vitamin K-dependent ligand Gas6 (growth arrest-specific 6). TAM family RTKs regulate a diverse range of cellular responses including cell survival, proliferation, autophagy, migration, angiogenesis, platelet aggregation, and natural killer cell differentiation. Axl is expressed in many embryonic tissues and is thought to be involved in mesenchymal and neural development, with expression in adult tissues largely restricted to smooth muscle cells (MGI Gene Expression Database; www.informatics.jax.org). Axl activation is linked to several signal transduction pathways, including Akt, MAP kinases, NF-κB, STAT, and others. Originally identified as a transforming gene from a patient with chronic myelogenous leukaemia, Axl has since been associated with various high-grade cancers and correlated with poor prognosis.

Axl receptor overexpression has been detected in a wide range of solid tumours and myeloid leukaemia (Linger et al, Adv Cancer Res. 100: 35, 2008; Linger et al, Expert Opin Ther Targets. 14:1073, 2010).

Axl expression correlates with malignant progression and is an independent predictor of poor patient overall survival in several malignancies including pancreatic (Song et al, Cancer. 117:734, 2011), prostate (Paccez et al, Oncogene. 32:698, 2013), lung (Ishikawa et al. Ann Surg Oncol. 2012; Zhang et al, Nat Genet. 44:852, 2012), breast (Gjerdrum, Proc natl Acad Sci USA 107:1124, 2010), colon cancer (Yuen et al, PLoS One, 8:e54211, 2013) and acute myeloid leukaemia (AML) (Ben-Batalla et al, Blood 122:2443, 2013).

Axl signal transduction is activated by a protein ligand (Gas6) secreted by tumour associated macrophages (Loges et al, Blood. 115:2264, 2010) or autocrine mechanisms (Gjerdrum, Proc natl Acad Sci USA 107:1124, 2010), that drives receptor dimerization, autophosphorylation and downstream signalling, such as via PI3 kinase (PI3K)-AKT, particularly AKT and mitogen-activated protein kinase (MAPK) pathways (Korshunov, Clinical Science. 122:361, 2012). Heterodimerization with other tyrosine kinase receptors, e.g. epidermal growth factor receptor (EGFR), is also reported to occur (Linger et al, Expert Opin Ther Targets. 14:1073, 2010; Meyer et al Science Signalling 6:ra66, 2013).

Aberrant activation of Axl in tumour cells is widely associated with acquired drug resistance to targeted therapeutics in vitro and in vivo (Zhang et al. Nat Genet. 44: 852, 2012; Byers et al. Clin Cancer Res. 19: 279, 2013). Axl-targeting agents block tumour formation, metastasis and reverse drug resistance (e.g. to erlotinib) by reversing EMT/CSC characteristics in several experimental cancer models, including triple negative breast cancer, hormone resistant prostate cancer and adenocarcinoma of the lung (Holland et al Cancer Res 70:1544, 2010; Gjerdrum, Proc natl Acad Sci USA 107:1124, 2010; Zhang et al. Nat Genet. 44: 852, 2012; Paccez et al, Oncogene. 32:698, 2013).

Other applications relating to Axl and anti-Axl antibodies include EP2267454A2 [Diagnosis and prevention of cancer cell invasion measuring . . . Axl-Max Planck]; WO2009063965 [anti Axl—Chugai Pharmaceutical]; WO2011159980A1 [anti-Axl-Genentech], WO2011014457A1 [combination treatments Axl and VEGF antagonists-Genentech]; WO2012-175691A1 [Anti Axl 20G7-D9—INSERM], WO2012-175692A1 [Anti Axl 3E3E8 -INSERM]; WO2009/062690A1 [anti Axl-U3 Pharma] and WO2010/130751A1 [humanised anti Axl-U3 Pharma].

In view of the role of Axl in tumourigenesis, it is desirable to identify further antibodies with advantageous properties, which specifically bind Axl. The present disclosure concerns such antibodies.

Figure 1:
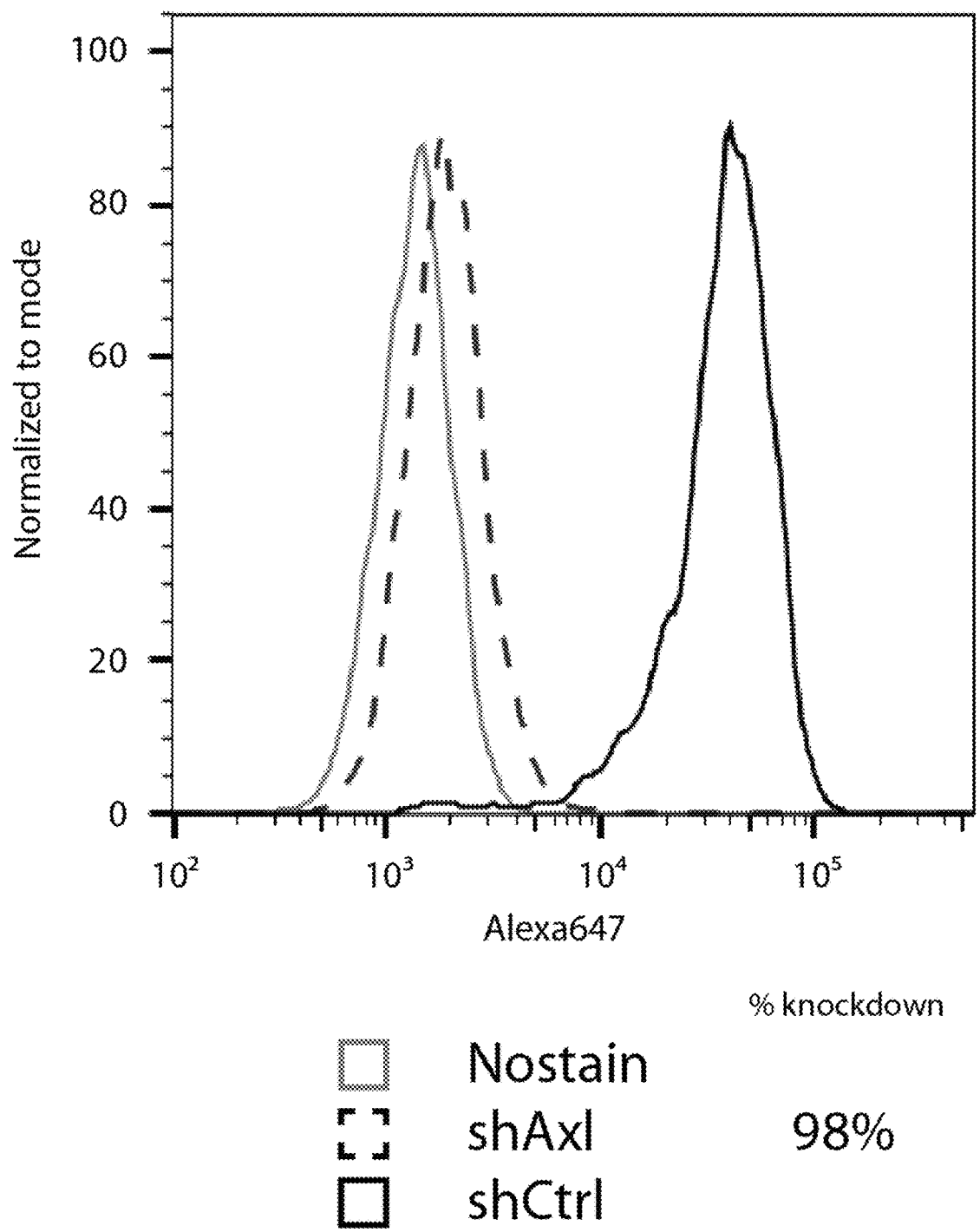
FIG. 1

Binding of monoclonal antibody (MAb) 1H12 to Axl$^+$ triple-negative breast cancer cell line MDA-MB-231 in flow cytometry. MAb 1H12 was conjugated with Alexa647 (Invitrogen) and incubated with either MDA-MB-231 cells having knocked down Axl expression or with cells transfected with a control shRNA. The cell staining was measured using Accuri C6 flow cytometer (BD Biosciences). The knockdown level was measured using values of geometric mean fluorescent intensity.

FIG. 2

Overlay plot of sensograms from a binding analysis showing interactions of MAb 1H12 with recombinant human (rh) Axl, rhMer and rhTyro3. The curves after subtraction of blank surface signals are shown.

FIG. 3

Biacore analyses of ligands (MAb 1H12 and rmGas6) interacting with a sensor chip CM5 coated with rhAxl, rmAxl and rhTyro3-Fc. The curves after subtraction of blank surface signals are shown.

FIG. 4

Kinetic analysis of MAb 1H12 interacting with rhAxl immobilized on the surface of the Biacore sensor chip. Overlay plot of sensograms for different concentrations (1.3-666.7 nM) of MAb 1H12 is shown. The precise kinetic analysis was performed using BIAevaluation software and curve fitting according to the model '1:1 binding with mass transfer'. The affinity constants (kinetic and steady state) as well as the calculated half-live of antigen binding at 25° C. are shown in the inset Table.

FIG. 5

Analysis of the competition between MAb 1H12 (1st sample) and anti-Axl MAb 1H12, MAbs 1-3, rhGas6 and rmGas6 (2nd samples) using Biacore 3000. The overlay plot of sensograms using different 2nd samples is shown. Start points of injections of the 1st sample (1H12) and the 2nd sample are indicated with arrows.

FIG. 6

Western blot analysis of anti-Axl MAb 1H12 binding to recombinant human (rh) Mer-Fc and Axl-Fc antigens under reducing and non-reducing conditions. Lanes: M, molecular weight markers (Magic Mark), the MW values in kDa are shown on the left; 1, rhAxl-Fc, non-reduced; 2, rhMer-Fc, non-reduced; 3, rhAxl-Fc, reduced; 4, rhMer-Fc, reduced. The protein bands corresponding to rhAxl-Fc are indicated with arrows.

FIG. 7

Western blot analysis of anti-Axl MAb 1H12 binding to the lysates of Axl+ and Axl− cells under reducing and non-reducing conditions. Lanes: M, molecular weight markers (Magic Mark), the MW values in kDa are shown on the left; 1, lysate of Axl− LNCaP cells (prostatic adenocarcinoma), reduced; 2, lysate of Axl+ NCI—H1299 (non-small cell lung carcinoma), reduced; 3, lysate of Axl+ NCI—H1299, non-reduced. The protein bands corresponding to Axl receptor are indicated with an arrow.

FIG. 8

Amino acid sequences of the VH (SEQ ID NO: 3) and VL (SEQ ID NO: 4) domains derived from anti-Axl monoclonal antibody 1H12.

FIG. 9

Dose-dependent binding of anti-Axl mouse antibody 1H12 and its chimeric (mouse variable/human constant) counterpart to Axl-positive cells. Different concentrations of mouse (m 1H12) and chimeric (ch 1H12) antibodies were tested in flow cytometry for binding to triple-negative breast cancer cell line MDA-MB-231. The bound mouse and chimeric antibodies were detected with APC-conjugated donkey F(ab')$_2$ fragments specific for either mouse IgG (H+L), 1:500 dilution, or human IgG (H+L), 1:300 dilution, respectively (both from Jackson ImmunoResearch). The cell staining was measured using Accuri C6 flow cytometer (BD Biosciences). MFI, geometric mean fluorescence intensity.

FIG. 10

Kinetic analysis of chimeric MAb ch1H12 interacting with rhAxl immobilized on the surface of the Biacore sensor chip. Overlay plot of sensograms for different concentrations (1.3-666.7 nM) of MAb ch1H12 is shown. The precise kinetic analysis was performed using BIAevaluation software and curve fitting according to 1:1 Langmuir binding model. The affinity constants (kinetic and steady state) as well as the calculated half-live of antigen binding at 25° C. are shown in the inset Table.

FIG. 11

Biacore analysis of the murine antibody 1H12 interacting with a sensor chip coated with human-Axl-Fc, cyno-Axl-Fc and rhesus-Axl-Fc.

FIG. 12

Tumour cell killing using antibody-Saporin conjugates. Unconjugated Saporin and an isotype control antibody (human IgG1) coupled to Saporin (control SAP) were used as negative controls. Effective concentrations leading to 50% cell killing ($EC_{50}$, pM) are shown in the inset Table.

FIG. 13

Western blot analysis illustrating agonistic activity of 1H12 antibody cross-linked with the secondary anti-mouse antibodies. Phosphorylation of Akt on Ser$^{473}$ was used as surrogate readout for Axl activity. Lanes: 1, molecular weight markers; 2, positive control (lysate of LNCaP cells from prostatic adenocarcinoma); 3, lysate of HeLa cells after starvation; 4, HeLa cells after starvation treated with cross-linked 1H12. Immunoblots of total cell lysates were probed with anti-phospho-Akt (Ser$^{473}$).

FIG. 14

Western blot analysis illustrating dose-dependent agonistic activity of 1H12 antibody cross-linked with the secondary anti-mouse antibodies. Phosphorylation of Akt on Ser$^{473}$ was used as surrogate readout for Axl activity. Lanes: 1, molecular weight markers; 2, positive control (lysate of LNCaP cells from prostatic adenocarcinoma); 3, lysate of HeLa cells after starvation; 4-7, HeLa cells after starvation treated with different doses of cross-linked 1H12 (0.2, 0.6, 2.0 and 6.0 µg/ml, respectively). Immunoblots of total cell lysates were probed with anti-phospho-Akt (Ser$^{473}$).

FIG. 15

Western blot analysis illustrating agonistic activity of 1H12 antibody alone. Phosphorylation of Akt on Ser$^{473}$ was used as surrogate readout for Axl activity. Lanes: 1, molecular weight markers; 2, positive control (lysate of LNCaP cells from prostatic adenocarcinoma); 3, lysate of HeLa cells after starvation; 4, lysate of HeLa cells after starvation additionally treated with Axl-Fc; 5, HeLa cells after starvation treated with cross-linked 1H12; 6, HeLa cells after starvation treated with cross-linked 1H12 lone. Immunoblots of total cell lysates were probed with anti-phospho-Akt (Ser$^{473}$).

FIG. 16

Analysis of the competition between MAb 1H12 as a 1st sample and either anti-Axl MAB154 or rmGas6 as 2nd samples using Biacore 3000. The overlay plot of sensograms using different 2nd samples is shown. Start points of injections of the 1st sample (1H12) and the 2nd sample are indicated with arrows.

FIG. 17

Comparative IHC staining of Axl+ and Axl− (A) cells using MAb 1H12, commercial antibody polyclonal AF154, and monoclonal MAB154. Wild type (wt) and Axl-knocked down MDA-MB-231 cells were used as Axl+ and Axl− cells, respectively. (B) Comparative Western blot analysis of Axl+ and Axl− cell lysates (wt and Axl-knocked-down MDA-MB-231 cells) developed using either MAb 1H12 or polyclonal AF154 and monoclonal MAB154. As a loading control, GAPDH detection is shown on every blot.

DISCLOSURE OF THE INVENTION

The following sequences are disclosed herein (see 'SEQUENCES' section below for full sequence):

| | | |
|---|---|---|
| SEQ ID NO. 1 | → | 1H12 VH encoding nucleotide sequence |
| SEQ ID NO. 2 | → | 1H12 VL encoding nucleotide sequence |
| SEQ ID NO. 3 | → | 1H12 VH encoding amino acid sequence |
| SEQ ID NO. 4 | → | 1H12 VL encoding amino acid sequence |
| SEQ ID NO. 5 | → | 1H12 VH CDR1 encoding amino acid sequence |
| SEQ ID NO. 6 | → | 1H12 VH CDR2 encoding amino acid sequence |
| SEQ ID NO. 7 | → | 1H12 VH CDR3 encoding amino acid sequence |
| SEQ ID NO. 8 | → | 1H12 VL CDR1 encoding amino acid sequence |
| SEQ ID NO. 9 | → | 1H12 VL CDR2 encoding amino acid sequence |
| SEQ ID NO. 10 | → | 1H12 VL CDR3 encoding amino acid sequence |
| SEQ ID NO. 11 | → | 1H12 VH FR1 encoding amino acid sequence |
| SEQ ID NO. 12 | → | 1H12 VH FR2 encoding amino acid sequence |
| SEQ ID NO. 13 | → | 1H12 VH FR3 encoding amino acid sequence |
| SEQ ID NO. 14 | → | 1H12 VH FR4 encoding amino acid sequence |
| SEQ ID NO. 15 | → | 1H12 VL FR1 encoding amino acid sequence |
| SEQ ID NO. 16 | → | 1H12 VL FR2 encoding amino acid sequence |
| SEQ ID NO. 17 | → | 1H12 VL FR3 encoding amino acid sequence |
| SEQ ID NO. 18 | → | 1H12 VL FR4 encoding amino acid sequence |
| SEQ ID NO. 19 | → | Human Axl encoding amino acid sequence |
| SEQ ID NO. 20 | → | Murine Axl encoding amino acid sequence |
| SEQ ID NO. 21 | → | Human Tyro3 encoding amino acid sequence |
| SEQ ID NO. 22 | → | Human Mer encoding amino acid sequence |

In one aspect, the present invention provides an isolated antibody which binds Axl and which comprises the 1H12 VH domain (SEQ ID NO: 3) and/or the 1H12 VL domain (SEQ ID NO: 4). Preferably the bound Axl is human Axl.

Generally, a VH domain is paired with a VL domain to provide an antibody antigen binding site, although as discussed further below a VH domain alone may be used to bind antigen. In one preferred embodiment, the 1H12 VH domain (SEQ ID NO: 3) is paired with the 1H12 VL domain (SEQ ID NO: 4), so that an antibody antigen binding site is formed comprising both the 1H12 VH and VL domains. In other embodiments, the 1H12 VH is paired with a VL domain other than the 1H12 VL. Light-chain promiscuity is well established in the art.

One or more CDR's may be taken from the 1H12 VH or VL domain and incorporated into a suitable framework. This is discussed further below. 1H12 VH CDR's 1, 2 and 3 are shown in SEQ ID Nos 5, 6 and 7, respectively. 1H12 VL CDR's 1, 2 and 3 are shown in SEQ ID Nos 8, 9, and 10, respectively.

In one aspect of the invention, there is provided an antibody that binds Axl and which comprises:
- an antibody VH domain selected from the group consisting of the 1H12 VH domain (SEQ ID NO.3) and a VH domain comprising a VH CDR3 with the amino acid sequence of SEQ ID NO.7 and optionally one or more VH CDR's with an amino acid sequence selected from SEQ ID NO.6 and SEQ ID NO.5; and/or
- an antibody VL domain selected from the group consisting of the 1H12 VL domain (SEQ ID NO. 4) and a VL domain comprising one or more VL CDR's with an amino acid sequence selected from SEQ ID NO.8, SEQ ID NO.9 and SEQ ID NO.10.

For example, the antibody may comprise an antibody VH domain comprising the VH CDR's with the amino acid sequences of SEQ ID NO.5, SEQ ID NO.6 and SEQ ID NO.7. The antibody may further comprise an antibody VL domain comprising the VL CDR's with the amino acid sequences of SEQ ID NO.8, SEQ ID NO.9 and SEQ ID NO.10.

In some embodiments the antibody comprises: (i) an antibody VH domain comprising the VH CDR's with the amino acid sequences of SEQ ID NO.5, SEQ ID NO.6 and SEQ ID NO.7, and (ii) an antibody VL domain comprising the VL CDR's with the amino acid sequences of SEQ ID NO.8, SEQ ID NO.9 and SEQ ID NO.10.

The antibody may comprise the 1H12 VH domain (SEQ ID NO. 3) and, optionally, further comprise the 1H12 VL domain (SEQ ID NO. 4)

Preferably, the antibody competes for binding to human Axl with an Axl binding domain of an antibody comprising the 1H12 VH domain (SEQ ID NO. 3) and the 1H12 VL domain (SEQ ID NO. 4).

According to a further aspect of the invention, there are provided variants of the VH and VL domains of which the sequences are set out herein and which can be employed in antibodies for Axl and can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1. Alterations may be made in one or more framework regions and/or one or more CDR's.

An antibody according to the invention may be one which competes for binding to antigen with any antibody which both binds the antigen and comprises an antibody VH and/or VL domain disclosed herein, or VH CDR3 disclosed herein, or variant of any of these. That is, in some embodiments the antibody according to the invention is an antibody which binds the same epitope or an overlapping epitope as an antibody which comprises an antibody VH and/or VL domain disclosed herein, or VH CDR3 disclosed herein, or variant of any of these. Competition between antibody may be assayed easily in vitro, for example using ELISA, using binding analysis in a Biacore 3000 machine (see, for example, Example 15 & FIG. 16), and/or by tagging a specific reporter molecule to one antibody which can be detected in the presence of other untagged antibody(s), to enable identification of antibodies which bind the same epitope or an overlapping epitope.

Accordingly, the present invention comprises a variant of any specifically disclosed herein, wherein the variant comprises one or more amino acid sequence alterations in one or more framework regions and/or one or more CDRs. For example, the variant antibody may comprise no more than 4 sequence alterations in any one CDR, such as no more than 3, no more than 2, no more than 1 sequence alterations, or no sequence alterations in any one CDR (such as CDR3 of the VH domain). The variant antibody may compete for binding to Axl (for example, human Axl) with an Axl binding domain of an antibody comprising the 1H12 VH domain (SEQ ID NO. 3) and the 1H12 VL domain (SEQ ID NO. 4).

Thus a further aspect of the present invention provides an antibody comprising a human antibody antigen-binding site which competes with 1H12 for binding to human Axl. Various methods are available in the art for obtaining antibodies against Axl and which may compete with 1H12 for binding to Axl.

In a further aspect, the present invention provides a method of obtaining one or more antibodies able to bind the antigen, the method including bringing into contact a library of antibodies according to the invention and said antigen, and selecting one or more antibody members of the library able to bind said antigen.

The library may be displayed on the surface of bacteriophage particles, each particle containing nucleic acid encoding the antibody VH variable domain displayed on its surface, and optionally also a displayed VL domain if present.

Following selection of antibodies able to bind the antigen and displayed on bacteriophage particles, nucleic acid may be taken from a bacteriophage particle displaying a said selected antibody. Such nucleic acid may be used in subsequent production of an antibody or an antibody VH variable domain (optionally an antibody VL variable domain) by expression from nucleic acid with the sequence of nucleic acid taken from a bacteriophage particle displaying a said selected antibody.

An antibody VH variable domain with the amino acid sequence of an antibody VH variable domain of a said selected antibody may be provided in isolated form, as may an antibody comprising such a VH domain.

Ability to bind Axl may be further tested, also ability to compete with 1H12 for binding to Axl.

An antibody according to the present invention may bind Axl with the affinity of 1H12.

An antibody of the invention may bind to murine, rat, monkey, non-human primate and/or human Axl. Preferably, the antibody binds to human and monkey Axl. In some embodiments the antibody specifically binds primate Axl. For example, the antibody may specifically bind human and monkey Axl. In one embodiment the antibody specifically binds only human Axl.

The antibody may be a chimeric, humanised, or CDR-grafted anti-Axl antibody. For example, the antibody may be a chimeric human/mouse antibody.

Binding affinity and neutralisation potency of different antibodies can be compared under appropriate conditions.

In addition to antibody sequences, an antibody according to the present invention may comprise other amino acids, e.g. forming a peptide or polypeptide, such as a folded domain, or to impart to the molecule another functional characteristic in addition to ability to bind antigen.

Antibodies of the invention may carry a detectable label, or may be conjugated to a toxin (such as a cytotoxin), enzyme, or an organic moiety (e.g. via a peptidyl bond or linker).

Those skilled in the art are aware of numerous approaches to chemically conjugating molecules to proteins. In one embodiment of the present invention, the antibody can be conjugated to a detectable, fluorescent label, e.g. fluorescein isothiocyanate (FITC), or to a reporter enzyme such as horseradish peroxidase (HRP)

In a preferred embodiment, the antibody is conjugated to a cytotoxic drug with a formation of the antibody-drug conjugate (ADC). When the antibody is for pharmaceutical use, the bond linking the antibody and drug is preferably stable in circulation (for example, blood circulation) but labile once the conjugate is sequestered intracellularly. Thus, the antibody conjugated as an immunoconjugate may be used in a method of treatment of, for example, cancer.

In further aspects, the invention provides an isolated nucleic acid which comprises a sequence encoding an antibody, VH domain and/or VL domain according to the present invention, and methods of preparing an antibody, a VH domain and/or a VL domain of the invention, which comprise expressing said nucleic acid under conditions to bring about production of said antibody, VH domain and/or VL domain, and recovering it.

Antibodies according to the invention may be used in a method of treatment or diagnosis of the human or animal body, such as a method of treatment (which may include prophylactic treatment) of a disease or disorder in a human patient which comprises administering to said patient an effective amount of an antibody of the invention, or a conjugate, or drug-conjugate thereof. Conditions treatable in accordance with the present invention include those discussed elsewhere herein.

Antibodies according to the invention may be used in a method of imaging, for example, to determine the presence or location of cells to which the antibody binds.

In a further aspect, the present invention provides a diagnostic kit comprising an antibody according to the invention and one or more reagents to determine binding of the antibody to the antigen.

A further aspect of the present invention provides nucleic acid, generally isolated, encoding an antibody VH variable domain (SEQ ID NO: 3) and/or VL variable domain (SEQ ID NO: 4) disclosed herein. In some embodiments the VH encoding nucleic acid has the sequence set out in SEQ ID NO: 1. In some embodiments the VL encoding nucleic acid has the sequence set out in SEQ ID NO: 2.

Another aspect of the present invention provides nucleic acid, generally isolated, encoding a VH CDR or VL CDR sequence disclosed herein, especially a VH CDR selected from SEQ ID NOs 5, 6, and 7 or a VL CDR selected from SEQ ID NOs 8, 9, or 10, most preferably1H12 CDR3 (SEQ ID NO: 7).

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and antibodies comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

Antibody Properties

High Affinity for Axl

The 1H12 antibody described herein binds to human Axl with high affinity. As described in Example 4, the 1H12 antibody was determined to have a $K_D$ of $4.98 \times 10^{-11}$ M. This is the lowest $K_D$ yet described for an anti-Axl antibody.

Unexpectedly, the chimeric MAb ch1H12 (see Example 11 & FIG. 10) has higher affinity still, with a $K_D = 1.10 \times 10^{-11}$ M; this figure is 4.5-fold lower than the parental murine antibody, possibly due to a better orientation of the VH and VL domains when mounted on a human constant domain scaffold.

Accordingly, the antibodies described herein bind Axl with high affinity; preferably human Axl is bound with high affinity. In some embodiments, an antibody binds to Axl (or human Axl) with a $K_D$ no greater than $10^{-6}$ M, such as no greater than $5 \times 10^{-7}$ M, no greater than $10^{-7}$ M, no greater than $5 \times 10^{-8}$ M, no greater than $10^{-8}$ M, no greater than $5 \times 10^{-9}$ M, no greater than $10^{-9}$ M, no greater than $5 \times 10^{-10}$ M, no greater than $10^{-10}$ M, no greater than $5 \times 10^{-11}$ M, no greater than $1.5 \times 10^{-11}$ M, no greater than $10^{-11}$ M, no greater than $5 \times 10^{-12}$ M, no greater than $10^{-12}$ M, no greater than $5 \times 10^{-13}$ M, no greater than $10^{-13}$ M, no greater than $5 \times 10^{-14}$ M, no greater than $10^{-14}$ M, no greater than $5 \times 10^{-15}$ M, or no greater than $10^{-15}$ M.

In some embodiments, an antibody binds to Axl (or human Axl) with a $K_D$ from $10^{-8}$ M to $10^{-10}$ M, from $10^{-10}$ M to $10^{-12}$, from $10^{-12}$ M to $10^{-14}$, or from $10^{-14}$ M to $10^{-16}$.

The $K_D$ may be determined and calculated as set out in Example 4.

The 1H12 antibody described herein is characterized by having a very slow dissociation rate ($k_{off}$). Specifically, in Example 4 the 1H12 antibody was determined to have very slow dissociation rate ($k_{off} = 1.07 \times 10^{-5}$ s$^{-1}$).

Unexpectedly, the chimeric MAb ch1H12 (see Example 11 & FIG. 10) has lower disassociation rate still, with a $k_{off} = 2.99 \times 10^{-6}$ s$^{-1}$), which resulted in 64.4 hr half-life of the ch1H12/Axl complex.

Accordingly, the antibodies described herein preferably bind human Axl with a slow disassociation rate. In some embodiments, an antibody binds to Axl (or human Axl) with a $k_{off}$ no greater than $10^{-3}$ s$^{-1}$, such as no greater than $5 \times 10^{-4}$ s$^{-1}$, no greater than $10^{-4}$ s$^{-1}$, no greater than $5 \times 10^{-5}$ s$^{-1}$, no greater than $2 \times 10^{-5}$ s$^{-1}$, no greater than $10^{-5}$ s$^{-1}$, no greater than $3 \times 10^{-6}$ s$^{-1}$, no greater than $5 \times 10^{-6}$ s$^{-1}$, no greater than $10^{-6}$ s$^{-1}$, no greater than $5 \times 10^{-7}$ s$^{-1}$, no greater than $10^{-7}$ s$^{-1}$, no greater than $5 \times 10^{-8}$ s$^{-1}$, or no greater than $10^{-8}$ s$^{-1}$.

Specific Binding

Generally, the terms 'specific' and 'specifically binds' may be used to refer to the situation in which an antibody will not show any significant binding to molecules other than its specific binding partner(s). For example, an antibody which 'specifically binds' human Axl would not show any significant binding for murine Axl.

The term is also applicable where e.g. an antibody is specific for a particular epitope which is carried by a number of antigens, in which case an antibody which 'specifically binds' an epitope will be able to bind to all of the various antigens which carry the recognised epitope.

Typically, specificity may be determined by means of a binding assay such as ELISA employing a panel of antigens.

The 1H12 antibody described herein binds to human Axl with high specificity. This is demonstrated in the examples, where it is shown that:
  (1) In Example 2, 1H12 shows no significant binding to recombinant antigens derived from hMer and hTyro3, the other members of the human TAM receptor tyrosine kinase family.
  (2) In Example 3, 1H12 binds strongly to human Axl, but shows no binding to murine Axl (this is in contrast to murine Axl ligand, murine Gas 6, which binds strongly to both murine and human Axl, as well as (more weakly) binding human Tyro3);
  (3) In Example 9, 1H12 shows either no or very little binding to the overwhelming majority of the tested tissue samples.

Accordingly, the antibodies described herein preferably specifically bind primate Axl. In some embodiments the antibodies described herein specifically bind human and monkey Axl. In one embodiment the antibodies specifically bind only human Axl.

In some embodiments of the present invention, the antibodies described herein show no significant binding to human Tyro3 and/or human Mer. In some embodiments the antibodies described herein show no significant binding to murine Axl. In some embodiments the antibodies described herein show no significant binding to any of human Tyro3, human Mer, or murine Axl.

Whether an antibody shows "no significant binding" to an antigen can be readily determined by the skilled person using, for example, the techniques described in Examples 2 and 3. In some embodiments, an antibody is deemed to show "no significant binding" to a particular antigen if it binds the antigen with a $K_D$ greater than $10^{-3}$ M, such as greater than $10^{-2}$ M, greater than $10^{-1}$ M, or greater than 1 M. The $K_D$ may be determined and calculated as set out in Example 4.

In one aspect, the antibodies of the invention bind the same epitope as the 1H12 antibody, or an epitope which overlaps with the epitope bound by the 1H12 antibody. Competition between different antibodies may be assayed easily in vitro, for example using ELISA and/or by tagging a specific reporter molecule to one binding member which can be detected in the presence of other untagged antibody (ies), to enable identification of antibodies which bind the same epitope or an overlapping epitope.

Antibody Internalisation

The 1H12 antibody described herein demonstrates good cell internalisation upon binding its target, Axl. Internalisation is also observed when the antibody is conjugated to a cytotoxin, such as Saporin (see Example 13 & FIG. 12).

Accordingly, the antibodies of the invention, or conjugates thereof, are preferably internalised following binding to Axl present on a cell surface.

Utility in Axl Detection

The unexpectedly good binding properties of the antibodies described herein make them particularly effective in applications involving the detection of Axl. For example, comparative tests have shown that the 1H12 antibody gives a notably stronger signal than the commercial anti-Axl antibodies to AF154 and MAB154 in both immunohistochemistry and western blotting applications (see Example 16 and FIG. 17); competition analysis indicates that 1H12 and MAB154 bind the same or overlapping epitope (see FIG. 16). This stronger signal and increased sensitivity of Axl detection provides a significant advantage in detection and analytical assays.

Agonism of Axl Signalling

The 1H12 antibody described herein can induce Axl signalling on binding to Axl. This is demonstrated in Example 14, along with FIGS. 13-15, where 1H12 binding is seen to induce strong Axl signalling in a dose-dependent manner as determined by measuring phosphorylation of the Axl-effector Akt on $Ser^{473}$.

Accordingly, in one aspect the antibodies described herein agonise Axl signalling; that is, the antibodies described herein are preferably Axl agonists.

In a further aspect, the present invention provides an antibody which binds the same epitope or an overlapping epitope as an antibody which comprises an antibody VH and/or VL domain disclosed herein, or VH CDR3 disclosed herein, or variant of any of these, wherein the antibody is an Axl agonist. Binding of ther same or an overlapping epitope can be readily determine in vitro by completion studies, as described herein.

In some embodiments Axl signalling is at least 10% greater in the presence of the antibody of the invention than in the presence of a non-Axl binding control antibody; for example, at least 10% greater, at least 20% greater, at least 30% greater, at least 40% greater, at least 50% greater, at least 60% greater, at least 70% greater, at least 80% greater, at least 90% greater, at least 100% greater, at least 200% greater, at least 500% greater or at least 1000% greater, in the presence of the antibody of the invention than in the presence of a non-Axl binding control antibody. The level of Axl signalling may be assessed by measuring phosphorylation of the Axl-effector Akt on $Ser^{473}$, as described herein in Example 14.

Down-Regulation of Axl Expression and/or Activity

In some embodiments, an anti-Axl antibody induces down-regulation of Axl receptor expression on a cell surface (e.g. a tumour cell surface).

In some embodiments, cell surface Axl expression is reduced to less than 80% of Axl cell surface expression in the absence of Axl antibody treatment. In some embodiments, cell surface expression is reduced to less than 70%, less than 60%, less than 50% or less than 40% of Axl cell surface expression in the absence of Axl antibody treatment.

In some embodiments, total Axl expression in a cell (e.g., a tumour cell) is reduced to less than 80% of total Axl expression in the absence of Axl antibody treatment. In some embodiments, total Axl expression is reduced to less than 70%, less than 60%, less than 50% or less than 40% of total Axl expression in the absence of Axl antibody treatment. In some embodiments, down-regulation of Axl expression occurs rapidly and lasts for at least 24 hours.

In some embodiments, an anti-Axl antibody inhibits constitutive Axl activity.

In some embodiments, an anti-Axl antibody inhibits Axl activity.

In some embodiments, an anti-Axl antibody promotes cell death, for example by apoptosis e.g., a tumour cell, such as a A549 tumour cell; this may be measured by, for example BrdU incorporation assay, MTT, $[^3H]$-thymidine incorporation (e.g., TopCount assay (PerkinElmer)), cell viability assays (e.g., CellTiter-Glo (Promega)), DNA fragmentation assays, caspase activation assays, tryptan blue exclusion, chromatin morphology assays and the like.

In some embodiments, an anti-Axl antibody inhibits Axl downstream signalling. In some embodiments, an anti-Axl antibody inhibits Gas6 dependent cell proliferation.

In some embodiments, an anti-Axl antibody inhibits inflammatory cytokine expression from tumour-associated macrophages.

In some embodiments, an anti-Axl antibody inhibits tumour growth and/or metastasis by modulating tumour stromal function.

Definitions

Antibody

This term describes an immunoglobulin whether natural or partly or wholly synthetically produced. The term also covers any polypeptide or protein comprising an antibody antigen-binding domain. Antibody fragments which comprise an antibody antigen-binding domain include whole antibodies (for example an IgG antibody comprising VH, CH1, CH2, CH3, VL, and CL domains in the canonical arrangement), or fragments of whole antibodies which retain their binding activity for a target antigen. Such fragments include Fv (fragment variable), Fab (fragment antibody binding) and F(ab')$_2$ fragments, as well as single-chain Fv antibodies (scFv), dsFv, minibodies, diabodies, single-chain diabodies, tandem scFv, TandAb, bi-body, tri-body, kappa (lambda) body, BiTE, DVD-Ig, SIP, SMIP, or DART. Furthermore, the antibodies and fragments thereof may be humanised antibodies, for example as described in EP239400A. For example: monoclonal and polyclonal antibodies, recombinant antibodies, proteolytic and recombinant fragments of antibodies (Fab, Fv, scFv, diabodies), single-domain antibodies (VHH, sdAb, nanobodies, IgNAR, VNAR), and proteins unrelated to antibodies, which have been engineered to have antibody-like specific binding (antibody mimetics), such as the following, but not limited to:

| Name | Based on: |
|---|---|
| Adnectins/Monobodies | 10th type III domain of human fibronectin (10Fn3), 10 kDa |
| Affibodies | Protein A, Z domain, 6 kDa |
| Affilins | Human γ-crystallin/human ubiquitin (10-20 kDa) |
| Affitins | Sac7d (from *Sulfolobus acidocaldarius*), 7 kDa |
| Anticalins | Lipocalins, 20 kDa |
| Avimers | Domains of various membrane receptors, 9-18 kDa |
| DARPins | Ankyrin repeat motif, 14 kDa |
| Evibody | Cytotoxic T-Lymphocyte Antigen 4 (CTLA-4), 15 kDa |
| Fynomers | Fyn, SH3 domain, 7 kDa |
| Kunitz domain peptides | Various protease inhibitors, 6 kDa |

An antibody may comprise all or apportion of an antibody heavy chain constant region and/or an antibody light chain constant region.

It is possible to take monoclonal and other antibodies and use techniques of recombinant DNA technology to produce engineered antibodies or chimeric molecules, which retain the specificity of the original antibody. Such techniques may involve ligation of DNA fragments encoding the immunoglobulin variable regions, or the complementarity determining regions (CDRs), of an antibody with genes coding for the immunoglobulin constant regions, or the constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody molecule" should be construed as covering any polypeptide or other molecule having an antibody-derived antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90, 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

The antibody may be bispecific or multispecific. Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the side effects, such as those due to the antibody effector functions, or human-anti-mouse antibody (HAMA) response in case of using antibodies of murine origin.

Bispecific diabodies, as opposed to bispecific whole antibodies, may also be particularly useful because they can be readily constructed and expressed in bacteria (e.g. Escherichia coli). Diabodies (and many other polypeptides such as antibody fragments) of appropriate binding specificities can be readily selected using phage display (WO94/13804) from the antibody libraries. If one arm of the diabody is to be kept constant, for instance, with a specificity directed against Axl, then a library can be made where the other arm is varied and an antibody of appropriate specificity selected. Bispecific whole antibodies may be made by "knobs-into-holes" engineering (J. B. B. Ridgeway et al, Protein Eng., 9, 616-621, 1996).

Antigen Binding Domain

This describes the part of an antibody molecule which comprises the area which recognizes and specifically binds to and is complementary part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific Proteins

Human Axl

As used herein, 'human Axl' refers to the Axl member of the human TAM family of receptor tyrosine kinases. In some embodiments, the human Axl polypeptide corresponds to Genbank accession no. AAH32229, version no. AAH32229.1 GI:21619004, record update date: Mar. 6, 2012 01:18 PM (SEQ ID NO.19). In one embodiment, the nucleic acid encoding the human Axl polypeptide corresponds to Genbank accession no. M76125, version no. M76125.1 GI:292869, record update date: Jun 23, 2010 08:53 AM.

Murine Axl

As used herein, 'murine Axl' refers to the Axl member of the murine TAM family of receptor tyrosine kinases. In some embodiments, the murine Axl polypeptide corresponds to Genbank accession no. AAH46618, version no. AAH46618.1 GI:55777082, record update date: Mar. 6, 2012 01:36 PM (SEQ ID NO.20). In one embodiment, the nucleic acid encoding the murine Axl polypeptide corresponds to Genbank accession no. NM_009465, version no. NM_009465.4 GI:300794836, record update date: Mar. 12, 2014 03:52 PM.

Human Tyro3

As used herein, 'human Tyro3' refers to the Tyro3 member of the human TAM family of receptor tyrosine kinases. In some embodiments, the human Tyro3 polypeptide corresponds to Genbank accession no. Q06418, version no. Q06418.1 GI:1717829, record update date: Apr. 22, 2014 12:07 PM (SEQ ID NO.21). In one embodiment, the nucleic acid encoding the human Tyro3 polypeptide corresponds to Genbank accession no. BC051756, version no. BC051756.1 GI:30704372, record update date: Mar. 6, 2012 01:43 PM.

Human Mer

As used herein, 'human Mer' refers to the Mer member of the human TAM family of receptor tyrosine kinases (official name=MERTK, Uniprot ID=Q12866). In some embodiments, the human Mer polypeptide corresponds to Genbank accession no. AAI14918, version no. AAI14918.1 GI:109732052, record update date: Mar. 6, 2012 04:21 PM (SEQ ID NO.22). In one embodiment, the nucleic acid encoding the human Mer polypeptide corresponds to Genbank accession no. NM_006343, version no. NM_006343.2 GI:66932917, record update date: Mar. 16, 2014 08:52 PM.

BSA

As used herein, 'BSA' refers to Bovine Serum Albumin. In some embodiments BSA corresponds to Genbank accession no. CAA76847, version no. CAA76847.1 GI:3336842, record update date: Jan. 7, 2011 02:30 PM.

Comprise

This is generally used in the sense of "include", that is to say permitting the presence of one or more features or components.

Isolated

This refers to the state in which antibodies of the invention, or nucleic acid encoding such antibody, will generally be in accordance with the present invention. Antibody and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Antibodies and nucleic acid may be formulated with diluents or adjuvants and still for practical purposes be isolated—for example the antibody will normally be mixed with gelatin or other carriers if used to coat microtitre plates for use in immunoassays, or will be mixed with pharmaceutically acceptable carriers or diluents when used in diagnosis or therapy. Antibodies may be glycosylated, either naturally or by systems of heterologous eukaryotic cells (e.g. CHO or NSO (ECACC 85110503) cells), or they may be (for example, if produced by expression in a prokaryotic cell) non-glycosylated.

Substantially as Set Out

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

Frameworks Supporting CDRs

The structure for carrying a CDR of the invention will generally be of an antibody heavy or light chain sequence or substantial portion thereof in which the CDR is located at a location corresponding to the CDR of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (immuno.bme.nwu.edu or find "Kabat" using any search engine).

Variable domains employed in the invention may be obtained from any germ-line or rearranged mouse or human variable domain, or may be a synthetic variable domain based on consensus sequences of known mouse or human variable domains. A CDR sequence of the invention (e.g. CDR3) may be introduced into a repertoire of variable domains lacking a CDR (e.g. CDR3), using recombinant DNA technology.

For example, Marks et al (Bio/Technology, 1992, 10:779-783) describe methods of producing repertoires of antibody variable domains in which consensus primers directed at or adjacent to the 5'-end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide antibodies of the invention. The repertoire may then be displayed in a suitable host system such as the phage display system of WO92/01047 so that suitable antibodies may be selected. A repertoire may consist of from anything from $10^4$ individual antibody upwards, for example from $10^6$ to $10^8$ or $10^{10}$ antibodies.

Analogous shuffling or combinatorial techniques are also disclosed by Stemmer (Nature, 1994, 370:389-391), who describes the technique of DNA shuffling in relation to a β-lactamase gene but observes that the approach may be used for the generation of antibodies.

A further alternative is to generate novel VH or VL regions carrying a CDR-derived sequences of the invention using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR.

Another method which may be used is to direct mutagenesis to CDR regions of VH or VL genes. Such techniques are disclosed by Barbas et al. (1994, Proc. Natl. Acad. Sci., USA, 91:3809-3813) and Schier et al. (1996, J. Mol. Biol. 263:551-567).

All the above-described techniques are known as such in the art and in themselves do not form part of the present invention. The skilled person will be able to use such techniques to provide antibodies of the invention using routine methodology in the art.

Epitope-Specific Antibodies

A further aspect of the invention provides a method for obtaining an antibody specific for an Axl epitope, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations for to identify a antibody or an antibody antigen binding domain specific for Axl. Said VL domain may have an amino acid sequence, which is substantially as set out herein.

An analogous method may be employed in which one or more sequence variants of a VL domain disclosed herein are combined with one or more VH domains.

A further aspect of the invention provides a method of preparing an antibody specific for Axl, which method comprises:
 (a) providing a starting repertoire of nucleic acids encoding a VH domain which either include a CDR3 to be replaced or lack a CDR3 encoding region;
 (b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
 (c) expressing the nucleic acids of said product repertoire;
 (d) selecting an antibody specific for Axl; and
 (e) recovering said antibody or nucleic acid encoding it.

Again, an analogous method may be employed in which a VL CDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for an antibody or antibodies specific for Axl.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibodies of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more details below.

Although in a preferred aspect of the invention antibodies comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either single binding domains, these domains may be used to screen for complementary domains capable of forming a two-domain antibody able to bind Axl.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain antibody is selected in accordance with phage display techniques such as those described in that reference. This technique is also disclosed in Marks et al., ibid.

Antibodies of the present invention may further comprise antibody constant regions or parts thereof. For example, an antibody of the present invention may comprise a CL, CH1, CH2, and/or a CH3 domain (or any combination thereof). A VL domain may be attached at its C-terminal end to antibody light chain constant domains including human Cκ or Cλ chains, preferably Cκ chains. Similarly, an antibody based on a VH domain may be attached at its C-terminal end to all or part of an immunoglobulin heavy chain derived from any antibody isotype, e.g. IgG, IgA, IgE and IgM and any of the isotype sub-classes. Fc regions such as Δnab and Δnac as disclosed in WO99/58572 may be employed.

Chimeric, Humanised and CDR-Grafted Antibodies

As used herein "chimeric" antibodies or "humanised" antibodies or "CDR-grafted" include any combination of the herein described anti-Axl antibodies, or any CDR derived therefrom combined with one or more proteins or peptides derived from a non-murine, preferably, human antibody.

Chimeric or humanised antibodies include those wherein the CDR's are derived from one or more of the herein described anti-Axl antibodies and at least a portion, or the remainder of the antibody is derived from one or more human antibodies. Thus, the human part of the antibody may include the frameworks, CL (e.g. Cκ or Cλ), CH domains (e.g., CH1, CH2, CH3), hinge regions which are substantially non-immunogenic in humans.

The regions of the antibody that are derived from human antibodies need not have 100% identity with human antibodies. In a preferred embodiment, as few of the mouse amino acid residues as possible are retained in order for the immunogenicity to be negligible, but the mouse residues may be retained as necessary to support the antigen binding site formed by the CDR's while simultaneously maximizing the humanization of the antibody. Such changes or variations optionally and preferably retain or reduce the immunogenicity in humans or other species relative to non-modified antibodies.

It should be noted that a humanised antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an scFv can comprise a linker peptide, such as two to about twenty glycine or other amino acid residues (preferably glycine and serine residues (e.g., Gly$_4$Ser or Gly$_2$Ser repeats)), which connects the variable region of the heavy chain and the variable region of the light chain. Such linker peptides are considered to be non-immunogenic in humans. In some embodiments the linker is of at least 12 amino acids in length.

Antibody humanisation can be performed by, for example, synthesizing a combinatorial library comprising all six CDRs of a non-human target monoclonal antibody fused in frame to a pool of individual human frameworks. A human framework library that contains genes representative of all known heavy and light chain human germline sequences can be utilized. The resulting combinatorial libraries can then be screened for binding to antigens of interest. This approach can allow for the selection of the most favourable combinations of fully human frameworks in terms of maintaining the binding activity to the parental antibody. Humanised antibodies can then be further optimized by a variety of techniques.

For full-length antibody molecules, the immunoglobulin genes can be obtained from genomic DNA or mRNA of hybridoma cell lines. The antibody heavy and light chains are cloned in a mammalian vector system. Assembly is confirmed by sequencing using methods known in the art. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

Human genes which encode the constant (C) regions of the humanized antibodies, fragments and regions can be derived from a human fetal liver library by known methods. Human C region genes can be derived from any human cell including those which express and produce human immunoglobulins. The human CH region can be derived from any of the known classes or isotypes of human heavy chains, including γ, μ, α, δ, ε, and subclasses thereof, such as G1, G2, G3 and G4. Since the heavy chain isotype is responsible for the various effector functions of an antibody, the choice of CH domain will be guided by the desired effector functions, such as complement fixation, or activity in antibody-dependent cellular cytotoxicity (ADCC). Preferably, the CH domain are derived from the gamma 1 (IgG1).

The human CL region can be derived from either human L chain isotype, kappa or lambda, preferably kappa.

Genes encoding human immunoglobulin C regions are obtained from human cells by standard cloning techniques (Sambrook, et al. Molecular Cloning: A Laboratory Manual, 2nd Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two types of light chains, the five classes of heavy chains and subclasses thereof.

Chimeric antibody fragments, such as Fab and F(ab')$_2$, can be prepared by designing a chimeric heavy chain gene which is appropriately truncated. For example, a chimeric gene encoding a heavy chain portion of an F(ab')$_2$ fragment would include DNA sequences encoding the CH1 domain and hinge region of the heavy chain, followed by a translational stop codon to yield the truncated molecule.

Methods for engineering or humanizing non-human or human antibodies can be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html; www.sciquest-.com/; www.abcam.com/; www.antibodyresource.com/onlinecomp.html; www.public.iastate.edu/.about.pedro/research_tools.html; www. mgen.uni-heidelberg.de/SD/IT/IT.html; www.whfreeman.com/immunology/CH05/kuby05.htm; www.library.thinkquest.org/12429/Immune/Antibody.html; www.hhmi.org/grants/lectures/1996/vlab/; www.path.cam.ac.uk/.about.mrc7/mikeimages.html; www.antibodyresource.com/; mcb.harvard.edu/BioLinks/Immunology.html. www.immunologylink.com/; path-box.wustl.edu/.about.hcenter/index.html; www.biotech.u-fl.edu/.about.hcl/; www.pebio.com/pa/340913/340913.html; www.nal.usda.gov/awic/pubs/antibody/; www.m.ehime-u.ac.jp/.about.yasuhito/Elisa.html; www.biodesign.com/table.asp; www.icnet.uk/axp/facs/davies/links.html; www.biotech.ufl.edu/.about.fccl/protocol.html; www. isac-net.org/sites_geo.html; aximt1.imt.uni-marburg.de/.about.rek/AEPStart.html; baserv.uci.kun.n/.about.jraats/links1.html; www.recab.uni-hd.de/immuno.bme.nwvu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.bio-sci.missouri.edu/smithgp/index.html; www.cryst.bioc.ca-m.ac.uk/.about.fmolina/Web-pages/Pept/spottech.html; www.jerini.de/fr_products.htm; www.patents.ibm.con/ibm.html. Kabat et al. Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally, part or all of the non-human or human CDR sequences are maintained while the non-human sequences of the variable and constant regions are replaced with human or other amino acids.

Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved.

In general, the CDR residues are directly and most substantially involved in influencing antigen binding. Humanization or engineering the antibody can be performed using any known method, such as but not limited to those described in Winter et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814, 476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246.

The human constant region of the humanized antibody can be of any class or isotype (IgG, IgA, IgM, IgE, IgD, etc.) and can comprise a kappa or lambda light chain. In one embodiment, the human constant region comprises an IgG heavy chain or defined fragment, for example, at least one of the IgG subclasses, IgG1, IgG2, IgG3 or IgG4.

Labelled Antibodies

Antibodies of the invention may be labelled with a detectable or functional label. Detectable labels include radiolabels such as [$^{131}$I] or [$^{99}$Tc], which may be attached to antibodies of the invention using conventional chemistry known in the art of radioimmunoconjugates. Labels also include enzyme labels such as horseradish peroxidase. Labels further include chemical moieties, such as biotin, which may be detected via binding to a specific cognate detectable moiety, e.g. labelled avidin or streptavidin. Preferably, the labels include fluorescent labels such as FITC.

Organic Moiety

The modified antibodies and antigen-binding fragments can comprise one or more organic moieties that are covalently bonded, directly or indirectly, to the antibody. Each organic moiety that is bonded to an antibody or antigen-binding fragment described herein can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, poly-lysine is more soluble in water than in octane. Thus, an antibody modified by the covalent attachment of poly-lysine is encompassed by the present disclosure. Hydrophilic polymers suitable for modifying antibodies described herein can be linear or branched and include, for example, poly-alkane glycols,e.g., polyethylene glycol (PEG), monomethoxy-polyethylene glycol (mPEG), PPG and the like, carbohydrates (e.g., dextran, cellulose, oligosaccharides, polysaccharides and the like), polymers of hydrophilic amino acids (e.g., poly-lysine, poly-arginine, poly-aspartate and the like), poly-alkane oxides (e.g., polyethylene oxide, polypropylene oxide and the like) and polyvinyl pyrolidone. Preferably, the hydrophilic polymer that modifies the antibody described herein has a molecular weight of about 800 to about 150,000 Daltons as a separate molecular entity. For example PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl di-imidazole) on a fatty acid or fatty acid ester can be coupled to a hydroxyl group on a polymer.

Fatty acids and fatty acid esters suitable for modifying antibodies described herein can be saturated or can contain one or more units of unsaturation. Fatty acids that are suitable for modifying antibodies described herein include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-δ9-octadecanoate (C18, oleate), all cis-δ5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetra-ethylene glycol, —(CH$_2$)$_3$—, —NH—(CH$_2$)$_6$—NH—, —(CH$_2$)$_2$—NH— and —CH$_2$)—O—CH$_2$—CH$_2$—O—CH$_2$—CH$_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221).

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody described herein. Modified human antibodies and antigen-binding fragments comprising an organic moiety that is bonded to specific sites of an antibody described herein can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Immunoconiuqates

The invention also provides immunoconjugates comprising an anti-Axl antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof(see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chern. 13:477-523 (2006); Jeffrey et al., Bioorganic & Med. Chern. Letters 16:358-362 (2006); Torgov et al., Bioconj. Chern. 16:717-721 (2005); Nagy et al., Proc. Natl. Acad. Sci. USA 97:829-834 (2000); Dubowchik et al., Bioorg. & Med. Chern. Letters 12:1529-1532 (2002); King et al., J. Med. Chern. 45:4336-4343 (2002); and U.S. Pat. No. 6,630, 579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria toxin A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (P API, P APII, and PAP-S), momordica charantia inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioimmunoconjugate. A variety of radioactive isotopes are available for the production of radioimmunoconjugates. Examples include [$^{211}$At], [$^{131}$I], [$^{125}$I], [$^{90}$Y], [$^{186}$Re], [$^{188}$Re], [$^{153}$Sm], [$^{212}$Bi], [$^{32}$P], [$^{212}$Pb] and radioactive isotopes of Lu. When the radioimmunoconjugate is used for detection, it may comprise a radioactive atom for scintigraphic studies, for example [$^{99}$Tc] or [$^{123}$I], or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N -maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MXDTPA) is an exemplary chelating agent for conjugation ofradionucleotide to the antibody. See WO94/11026. The linker may be a "cleavable linker" facilitating release of a cytotoxic drug in the cell. For example, an acid-labile linker, peptidase-sensitive linker, photo-labile linker, dimethyl linker or disulfide-containing linker (Chari et al., Cancer Res. 52: 127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Haklw Kogyo Co., Ltd). Examples of publications related to "defucosylated" or "fucose-deficient" antibody variants include: US2003/01571; WO2000/61739; WO2001/29246; US2003/0115614; US2002/0164328; US2004/0093621; US2004/0132140; US2004/0110704; US2004/0110282; US2004/0109865; WO2003/085119; WO2003/084570; WO2005/035586; WO2005/035778; WO2005/053742; WO2002/031140; Okazaki et al. J. Mol. Biol. 336:1239-1249 (2004); Yamane-Ohnuki et al. Biotech. Bioeng. 87: 614 (2004).

Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US2005/0123546 (Umana et al.). Antibody variants with at least one galactose residue in the oligosaccharide attached to the Fe region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement fixation and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fcγ binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166: 1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks complement-dependent cytotoxicity (CDC) activity. See, e.g., C1q and C3c binding ELISA in WO2006/029879 and WO2005/100402. To assess complement activation, a CDC assay may be performed (see, for example, Gazzano-Santoro et al., J. Immunol. Methods 202:163 (1996); Cragg, M.S. et al., Blood 101:1045-1052 (2003); and Cragg, M. S. and M. J. Glennie, Blood 103:2738-2743 (2004)). FcRn binding and in vivo clearance/half-life Fc determinations can also be performed using methods known in the art (see, e.g., Petkova, S. B. et al., Int'l. Immunol. 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (US Pat. No. 7,332,581).

Certain antibody variants with improved or diminished binding to FcRs are described (see, e.g., U.S. Pat. No. 6,737,056; WO 2004/056312, and Shields et al., J. Biol. Chem. 9(2): 6591-6604 (2001)).

In certain embodiments, an antibody variant comprises an Fc region with one or more amino acid substitutions, which improve ADCC activity, e.g., substitutions at positions 298, 333, and/or of the Fc region (EU numbering of residues).

In some embodiments, alterations are made in the Fc region that result in altered (i.e., either improved or diminished) C1q binding and/or CDC activity, e.g., as described in U.S. Pat. No. 6,194,551, WO 99/51642, and Idusogie et al. J. Immunol. 164: 4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol.

24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues.

In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Methods of Diagnosis and Treatment

Antibodies of the present invention are designed to be used in methods of diagnosis or treatment in human or animal subjects, preferably human.

Accordingly, further aspects of the invention provide methods of diagnosis comprising administration of an antibody as provided, with one or more reagents e.g. conjugated to a detectable label such as FITC. The antibody as provided may be used in the development of a rapid and reliable test for cancer cells derived from biopsied tissue. For example, the antibody may be used as a test for metastatic cancer cells, such as circulating tumour cells, which may be found circulating in body fluids such as blood or lymph. Other cancers of interest include breast, lung, gastric, head and neck, colorectal, renal, pancreatic, uterine, hepatic, bladder, endometrial and prostate cancers as well as lymphomas (e.g., non-Hodgkin's lymphoma, NHL) and leukemia (particularly acute myeloid leukemia, AML).

Further aspects of the invention provide methods of treatment comprising administration of an antibody as provided, pharmaceutical compositions comprising such an antibody, the antibody as described herein for use in a method of treatment, the antibody as described herein for use in a method of treatment of particular clinical indications described herein, and use of such an antibody in the manufacture of a medicament for administration, for example in a method of making a medicament or pharmaceutical composition comprising formulating the antibody with a pharmaceutically acceptable excipient.

Clinical Indications

Clinical indications in which an antibody with high specificity for human Axl may be used to provide therapeutic benefit include any condition in which Axl is overexpressed, or wherein Axl antagonism will provide a clinical benefit. These include immune disorders, cardiovascular disorders, thrombosis, diabetes, immune checkpoint disorders, or proliferative diseases such as cancer, particularly metastatic cancer. Furthermore, Axl is known to play a role in many cancers of epithelial origin.

Immune checkpoint disorders of interest include: Chronic viral infections, Melanoma, Colorectal cancer, Breast cancer, Ovarian cancer, Non-small cell lung cancer (NSCLC), Prostate cancer, Renal cell cancer, Pancreatic cancer, Esophagus cancer, Bladder cancer, Myeloma, Kidney cancer, Bladder cancer, Brain tumor, and Lymphoma Cancers of interest include: leukaemias such as but not limited to, acute leukemia, acute lymphocytic leukemia, acute myelocytic leukaemias such as myeloblastic, promyelocytic, myelomonocytic, monocytic, erythroleukaemia leukaemias and myelodysplastic syndrome, chronic leukaemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, glioblastoma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer (NSCLC), squamous cell carcinoma (epidermoid carcinoma), adenocarcinoma, large-cell carcinoma and small-cell lung cancer (SCLC); testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; genital cancers such as penile cancer; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. Preferably, the cancer is selected from breast, melanoma, prostate, ovarian, colorectal, lung or glioma cancer. More preferably, the cancer is metastatic breast or lung cancer. The targeting and treatment of circulating tumour cells is envisaged.

The treatment of metastatic cancer depends on where the primary tumour is located. When breast cancer spreads to the lungs, for example, it remains a breast cancer and the treatment is determined by the metastatic cancer origin within the breast, not by the fact that it is now in the lung. About 5 percent of the time, metastatic cancer is discovered but the primary tumour cannot be identified. The treatment of these metastatic cancers is dictated by their location rather than their origin. Metastatic cancers are named by the tissue of the original tumour (if known). For example, a breast cancer that has spread to the brain is called metastatic breast cancer to the brain.

Anti-Axl treatment in accordance with the present invention may be used to provide clear benefit for patients with conditions where Axl is overexpressed, or wherein Axl antagonism will provide a clinical benefit. Treatment may be given by injection (e.g. intravenously) or by local delivery methods. The antibody as provided may be used to direct the delivery of pharmaceutical compositions to the target tissue, or systemically in order to target, for example, Circulating Tumour Cells (CTCs) or other metastatic cells.

In a further aspect of the invention, there is provided a method of inhibiting Cancer Stem Cells in a subject, the method comprising of contacting the subject with an antibody (or conjugate thereof) as described herein. Antibodies and conjugates for use in such a method are also envisaged.

EGFR Antagonism

The invention also provides methods of inhibiting constitutive Axl activation comprising administering to the individual an effective amount of any of the anti-Axl antibodies disclosed herein to inhibit constitutive Axl.

In one aspect, the invention provides methods for treating a subject suffering from a cancer associated with an EGFR activating mutation or an EGFR gene amplification, wherein the subject has developed a resistance to treatment with an EGFR antagonist, comprising determining whether the subject has Axl expression, an Axl activating mutation or an Axl gene amplification, and administering to those subjects having an Axl activating mutation or an Axl gene amplification an EGFR antagonist and any of the anti-Axl antibodies described herein.

In one aspect, the invention provides methods for treating a subject suffering from a cancer associated with an EGFR activating mutation or an EGFR gene amplification, comprising: (i) monitoring a subject being treated with an EGFR antagonist to determine if the subject develops Axl expression, an Axl activating mutation or an Axl gene amplification, and (ii) modifying the treatment regimen of the subject to include any of the anti-Axl antibodies described herein in addition to the EGFR antagonist where the subject has developed an Axl activating mutation or an Axl gene amplification.

In one aspect, the invention provides methods for treating a subject suffering from a cancer associated with an EGFR activating mutation or an EGFR gene amplification, comprising: (i) monitoring a subject being treated with EGFR antagonist to determine if the subject develops a resistance to the inhibitor, (ii) testing the subject to determine whether the subject has Axl expression, an Axl activating mutation or an Axl gene amplification, and (iii) modifying the treatment regimen of the subject to include any of the anti-Axl antibodies described herein in addition to the EGFR antagonist where the subject has an Axl activating mutation or an Axl gene amplification.

In one aspect, the invention provides methods for evaluating an EGFR antagonist, comprising: (i) monitoring a population of subjects being treated with an EGFR antagonist to identify those subjects that develop a resistance to the therapeutic, (ii) testing the resistant subjects to determine whether the subjects have Axl expression, an Axl activating mutation or an Axl gene amplification, and (iii) modifying the treatment regimen of the subjects to include any of the anti-Axl antibodies described herein in addition to the EGFR antagonist where the subjects have Axl expression, an Axl activating mutation or an Axl gene amplification.

In one aspect, the invention provides methods for reducing EGFR phosphorylation in a cancer cell, wherein said cancer cell has acquired resistance to an EGFR antagonist, and wherein said cell comprises an Axl activating mutation or an Axl gene amplification, comprising the step of contacting the cell with any of the anti-Axl antibodies described herein and an EGFR antagonist.

In one aspect, the invention provides methods for reducing PBK mediated signaling in a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for reducing EGFR-mediated signaling in a cancer cell, wherein said cancer cell has acquired resistance to an EGFR antagonist, and wherein said cell comprises Axl expression, an Axl activating mutation or an Axl gene amplification, comprising contacting the cell with any of the anti-Axl antibodies described herein and an EGFR antagonist.

In one aspect, the invention provides methods for restoring sensitivity of a cancer cell to an EGFR antagonist, wherein said cancer cell has acquired resistance to an EGFR antagonist, and wherein said cell comprises Axl expression, an Axl activating mutation or an Axl gene amplification, comprising contacting the cell with any of the anti-Axl antibodies described herein and an EGFR antagonist.

In one aspect, the invention provides methods for reducing growth or proliferation of a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for increasing apoptosis of a cancer cell, wherein said cancer cell has acquired resistance to an EGFR antagonist, and wherein said cell comprises Axl expression, an Axl activating mutation or an Axl gene amplification, comprising the step of contacting the cell with any of the anti-Axl antibodies described herein and an EGFR antagonist.

In one aspect, the invention provides methods for reducing resistance of a cancer cell to an EGFR antagonist, wherein said cancer cell has acquired resistance to an EGFR antagonist, and wherein said cell comprises an Axl activating mutation or an Axl gene amplification, comprising the step of contacting the cell with any of the anti-Axl antibodies described herein and an EGFR antagonist.

In one aspect, the invention provides methods for treating acquired EGFR antagonist resistance in a cancer cell, wherein said cell comprises an Axl activating mutation or an Axl gene amplification, comprising contacting the cell with any of the anti-Axl antibodies described herein and an EGFR antagonist.

In some embodiments, the cancer cell is any EGFR-driven cancer. In some embodiments, the cancer cell comprises an EGFR activating mutation. In some embodiments, the cancer cell comprises an EGFR gene amplification. In some embodiments, the EGFR gene amplification is at least 2-fold. In some embodiments, the Axl amplification is at least 2-fold. In some embodiments, the cancer cell comprises an EGFR gene mutation associated with increased resistance to an EGFR antagonist. In some embodiments, the EGFR gene mutation associated with increased resistance to an EGFR antagonist is a T790M mutation of EGFR.

In some embodiments, the EGFR antagonist is a small molecule therapeutic, a nucleic acid therapeutic, or a protein therapeutic. In some embodiments, the EGFR antagonist is an antibody, an antisense molecule, or a small molecule kinase inhibitor. In some embodiments, the EGFR antagonist is an EGFR kinase inhibitor selected from the group consisting of: gefitinib, erlotinib, cetuximab, pantinumumab. In some embodiments, the EGFR antagonist is an anti-EGFR antibody selected from the group consisting of: cetuximab, panitumumab. In some embodiments, the nucleic acid therapeutic is a siRNA molecule.

In one aspect, the invention provides methods for identifying a subject as a candidate for treatment with an EGFR antagonist and any of the anti-Axl antibodies described herein, wherein said subject has been treated with an EGFR antagonist and suffers from cancer that has acquired resistance to said EGFR antagonist, comprising detecting Axl expression, an Axl activating mutation or Axl gene amplification in a cancer cell from said subject.

In one aspect, the invention provides methods for identifying a subject who is being treated with an EGFR antagonist and who is at risk for acquiring resistance to said EGFR antagonist, comprising detecting the presence of Axl expression, an Axl activating mutation or an Axl gene amplification in a cancer cell from said subject, wherein the presence of said Axl expression, Axl activating mutation or Axl gene amplification indicates a risk for acquiring said resistance.

In one aspect, the invention provides methods for treating a subject suffering from a cancer that is resistant to treatment with an EGFR antagonist, comprising administering to the subject an EGFR antagonist and any of the anti-Axl antibodies described herein.

In one aspect, the invention provides methods for treating a subject suffering from a cancer associated with an EGFR activating mutation or an EGFR gene amplification, wherein the subject has developed a resistance to treatment with an EGFR antagonist, comprising determining whether the subject has Axl expression, such as elevated Axl levels and/or activity, and administering to those subjects having Axl expression, such as elevated Axl activity an EGFR antagonist and any of the anti-Axl antibodies described herein.

In one aspect, the invention provides methods for treating a subject suffering from a cancer associated with an EGFR activating mutation or an EGFR gene amplification, comprising: (i) monitoring a subject being treated with an EGFR antagonist to determine if the subject develops Axl expression, such as elevated levels and/or Axl activity, and (ii) modifying the treatment regimen of the subject to include any of the anti-Axl antibodies described herein in addition to the EGFR antagonist where the subject has developed Axl expression, such as elevated Axl levels and/or activity.

In one aspect, the invention provides methods for treating a subject suffering from a cancer associated with an EGFR activating mutation or an EGFR gene amplification, comprising: (i) monitoring a subject being treated with EGFR antagonist to determine if the subject develops a resistance to the inhibitor, (ii) testing the subject to determine whether the subject has Axl expression, such as elevated Axl levels and/or activity, and (iii) modifying the treatment regimen of the subject to include any of the anti-Axl antibodies described herein in addition to the EGFR antagonist where the subject has elevated Axl levels and/or activity.

In another aspect, the invention provides a method for (i) restoring the sensitivity of a cancer cell to an EGFR antagonist, (ii) reducing resistance of a cancer cell to an EGFR antagonist, and/or (iii) treating acquired EGFR antagonist resistance in a cancer cell, by contacting the cell with an EGFR antagonist and any of the anti-Axl antibodies described herein.

In exemplary embodiments, the cancer cell has acquired a resistance to an EGFR antagonist and comprises elevated levels of Axl activity and/or expression, e.g., associated with an activating mutation in the Axl gene, an Axl gene amplification, or Gas6 mediated Axl activation. The methods disclosed herein may be used to restore the sensitivity, reduce the resistance, and/or treat an acquired resistance, of a cancer cell.

In another aspect, the invention provides a method for reducing growth and/or proliferation of a cancer cell, or increasing apoptosis of a cancer cell, by contacting the cell with an EGFR antagonist and any of the anti-Axl antibodies described herein. In exemplary embodiments, the cancer cell has acquired a resistance to an EGFR antagonist and comprises elevated Axl activity and/or expression, e.g., associated with an activating mutation in the Axl gene, an Axl gene amplification, or Gas6 mediated Axl activation.

Pharmaceutical Compositions

Antibodies of the present invention will usually be administered in the form of a pharmaceutical composition, which may comprise at least one component in addition to the antibody.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous. The pharmaceutical compositions may be for human or animal usage in human and veterinary medicine.

Examples of such suitable excipients for the various different forms of pharmaceutical compositions described herein may be found in the "Handbook of Pharmaceutical Excipients", 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methylcellulose, magnesium stearate, mannitol, sorbitol and the like. Examples of suitable diluents include ethanol, glycerol, water and buffered saline.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like. Preservatives, stabilizers, dyes and even flavoring agents may be provided in the pharmaceutical composition. Examples of preservatives include sodium benzoate, sorbic acid and esters of p hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration, e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation. Pharmaceutical formulations suitable for oral administration wherein the carrier is a solid are most preferably presented as unit dose formulations such as boluses, capsules or tablets each containing a predetermined amount of active agent. A tablet may be made by compression or moulding, optionally with one or more accessory ingredients. Compressed tablets may be prepared by compressing in a suitable machine an active agent in a free-flowing form such as a powder or granules optionally mixed with a binder, lubricant, inert diluent, lubricating agent, surface-active agent or dispersing agent. Moulded tablets may be made by moulding an active agent with an inert liquid diluent. Tablets may be optionally coated and, if uncoated, may optionally be scored. Capsules may be prepared by filling an active agent, either alone or in admixture with one or more accessory ingredients, into the capsule shells and then sealing them in the usual manner. Cachets are analogous to capsules wherein an active agent together with any accessory ingredient(s) is sealed in a rice paper envelope. An active agent may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active agent is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active agent with the softened or melted carrier(s) followed by chilling and shaping in moulds.

Pharmaceutical formulations suitable for parenteral administration include sterile solutions or suspensions of an active agent in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active agent may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient. As one possibility such formulations are in the form of finely comminuted powders which may conveniently be presented either in a pierceable capsule, suitably of, for example, gelatin, for use in an inhalation device, or alternatively as a self-propelling formulation comprising an active agent, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active agent is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility, an active agent may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active agent in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing an agent into association with a pharmaceutically or veterinary acceptable carrier or vehicle.

Administration

The pharmaceutical compositions of the present invention may be adapted for oral, rectal, nasal, intrabronchial, topical (including buccal and sublingual), vaginal or parenteral (including subcutaneous, intramuscular, intravenous, intra-arterial and intradermal), intraperitoneal or intrathecal administration. Preferably, the formulation is an intravenously or subcutaneously administered formulation.

The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Alternative formulation strategies may provide preparations suitable for oral or suppository route. The route of administration may be determined by the physicochemical characteristics of the treatment, by special considerations for the disease, to optimise efficacy or to minimise side-effects.

A further mode of administration employs pre-coating of, or otherwise incorporation into, indwelling devices, for which the optimal amount of antibody will be determined by means of appropriate experiments.

An antibody molecule in some preferred embodiments of the invention is a monomeric fragment, such as Fab or scFv. Such antibody fragments may have the feature of a relatively short half-life.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy.

In accordance with the present invention, compositions provided may be administered to individual patients. Administration is preferably in a "therapeutically effective amount", this being sufficient to show benefit to a patient. Such benefit may be at least amelioration of at least one symptom. The actual amount administered, and the rate and time-course of administration, will depend on the nature and severity of what is being treated. Prescription of treatment, e.g., decisions on dosage etc., is within the responsibility of general practitioners and other medical doctors. Appropriate doses of antibody are well known in the art; see Ledermann J. A. et al. (1991) Int. J. Cancer 47: 659-664; Bagshawe, K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, antibody fragment or diabody), and the nature of any detectable label or other molecule attached to the antibody. A typical antibody dose may be administered as a bolus intravenously. Other modes of administration include intravenous infusion over several hours, to achieve a similar total cumulative dose. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

The dosages disclosed herein are exemplary of the average case. There can of course be individual instances where higher or lower dosage ranges are merited, and such are within the scope of this invention.

In accordance with this invention, an effective amount of agent may be administered to inhibit Axl. Of course, this dosage amount will further be modified according to the type of administration of the agent. For example, to achieve an "effective amount" for acute therapy, parenteral administration is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase or saturate the target receptor. The agents may be administered one to four times daily at a level to achieve a total daily dose of about 0.4 to about 400 mg/kg/day. The precise amount of an active agent which is therapeutically effective, and the route by which such agent is best administered, is readily determined by one of ordinary skill in the art by comparing the blood level of the agent to the concentration required to have a therapeutic effect.

The agents of this invention may also be administered orally to the patient, in a manner such that the concentration of drug is sufficient to achieve one or more of the therapeutic indications disclosed herein. Typically, a pharmaceutical composition containing the agent is administered at an oral dose of between about 0.1 to about 50 mg/kg in a manner consistent with the condition of the patient. Preferably the oral dose would be about 0.5 to about 20 mg/kg.

The agents of this invention may be tested in one of several biological assays to determine the concentration of an agent which is required to have a given pharmacological effect.

Combination Therapy

A composition may be administered alone or in combination with other treatments, either simultaneously or sequentially dependent upon the condition to be treated. For example, the antibodies of the invention or conjugates thereof may be used as an anti-cancer monotherapy or in combination therapy with other cancer treatments as mentioned below. Other treatments may include the administration of suitable doses of pain relief drugs such as non-steroidal anti-inflammatory drugs (e.g. aspirin, ibuprofen or ketoprofen) or opiates such as morphine, or anti-emetics.

In a preferred aspect the antibodies of the invention (or conjugates thereof) are administered in combination with an immune checkpoint modulator (ICM), such as an immune checkpoint inhibitor (ICI). Typically, an ICM is an agent, such as an aptamer or an antibody, which binds the targeted receptor.

The ICM used in combination with an antibody of the invention (or conjugate thereof) may be any suitable ICM known in the art. In particular, suitable immune checkpoint modulating agents include:

CTLA-4 targeting agents, including Ipilimumab and Tremelimumab. PD-1 targeting agents, including Pembrolizumab, Mivolumab and AMP-514/MED10680.

BD-L1 targeting agents, including MPDL3280A, MED14736, MSB0010718C and BMS-936559.

4-1BB targeting agents, including Urelumab and PF-05082566.

OX-40 targeting agents, including MED16469, MED16383 (rOX40L) and MOXR0916.

GITR targeting agents, including TRX518.
CD27 targeting agents, including CDX-1127.
CD40 targeting agents, including CP-870,893.
LAG3 targeting agents, including BMS-986016.

Immune checkpoints, which are inhibitory pathways in the immune system, may be co-opted by tumours to induce immune resistance. The use of agents to block or modulate immune checkpoints, including T-cell stimulatory and inhibitory receptors and dendritic cell stimulatory receptors, and thus to reduce or reverse the immune resistance of the cancer, is an important avenue in cancer research.

T-cell stimulatory receptors which may be modulated through the use of ICMs include CD28, ICOS, 4-1BB, OX40, GITR, CD27, TWEAKR, HVEM and TIM-1. T-cell inhibitory receptors which maybe modulated through the use of ICMs include PD-L1, CTLA-4, PD-1, BTLA, TIM-3, VISTA, LAG-3 and TIGIT. Dendritic cell stimulatory receptors which may be modulated through the use of ICMs include CD40 and 4-1BB.

Where a combination of ICMs are used in conjunction with an antibody of the invention (or conjugate thereof), all of the ICMs may target inhibitory receptors, all of the ICMs used may target stimulatory receptors, or a combination of inhibitory receptor and stimulatory receptor targeting ICMs may be used.

Thus, there is thus provided an antibody of the invention (or conjugate thereof) for use a method of treating of cancer, wherein the treatment further comprises administering one or more ICM. Similarly, there is provided the use of an antibody of the invention (or conjugate thereof) in the manufacture of a medicament for the treatment of cancer, wherein the treatment further comprises administering one or more immune checkpoint modulating agents.

There is also provided an antibody of the invention (or conjugate thereof) for use in a method of treating cancer, or the use of such an antibody (or conjugate thereof) in the manufacture of a medicament for the treatment of cancer, wherein the treatment further comprises one or more immune checkpoint modulating agents selected from Ipilimumab, Tremelimumab, Pembrolizumab, Mivolumab, AMP-514/MED10680, MPDL3280A, MEDI4736, MSB0010718C, BMS-936559, Urelumab, PF-05082566, MEDI6469, MEDI6383 (rOX4OL), MOXR0916, TRX518, CDX-1127, CP-870,893 and BMS-986016.

The antibody of the invention (or conjugate thereof) may be administered before the one or more ICM, simultaneously with the one or more ICM, or after the one or more ICM.

There is also provided an antibody of the invention (or conjugate thereof) for use in the treatment of cancer, or the use of such an antibody (or conjugate thereof) in the manufacture of a medicament for the treatment of cancer, wherein the treatment further comprises one or more ICM, and wherein the cancer is selected from lung cancer, melanoma, breast cancer, ovarian cancer or carcinoma.

Suitable Agents for use in Combination Therapy
  These include alkylating agents, e.g., alkyl sulfonates such as busulfan; nitrogen mustards such as chlorambucil, cyclophosphamide, estramustine, ifosfamide, mechlorethamine, melphalan, and uramustine, ethyleneimine derivatives such as thiotepa;
  nitrosoureas such as carmustine, lomustine, and streptozocin, triazenes such as dacarbazine, procarbazine, and temozolamide;
  platinum compounds such as cisplatin, carboplatin, oxaliplatin, satraplatin, and picoplatin onnaplatin, tetraplatin, sprioplatin, iproplatin, chloro(diethylenediamino)-platinum (II) chloride, dichloro(ethylenediamino)-platinum (II), diamino(2-ethylmalonato)platinum (II), (1,2-diaminocyclohexane)malonatoplatinum (II), (4-carboxyphthalo)-(1,2-diaminocyclohexane)platinum (II), (1,2-diaminocyclohexane)-(isocitrato)platinum (II), and (1,2-diaminocyclohexane)-cis-(pyruvato) platinum (II);
  anti-metabolites, including antifolates such as methotrexate, permetrexed, raltitrexed, and trimetrexate;
  pyrimidine analogs such as azacitidine, capecitabine, cytarabine, edatrexate, floxuridine, fluorouracil, gemcitabine, and troxacitabine;
  purine analogs such as cladribine, chlorodeoxyadenosine, clofarabine, fludarabine, mercaptopurine, pentostatin, and thioguanine;
  natural products, including antitumor antibiotics such as bleomycin, dactinomycin, mithramycin, mitomycin, mitoxantrone, porfiromycin, and anthracyclines such as daunorubicin, doxorubicin, epirubicin, idarubicin, and valrubicin;
  mitotic inhibitors such as the vinca alkaloids vinblastine, vinvesir, vincristine, vindesine, and vinorelbine;
  enzymes such as L-asparaginase and PEG-L-asparaginase;
  microtubule polymer stabilizers such as the taxanes paclitaxel and docetaxel;
  topoisomerase I inhibitors such as the camptothecins irinotecan and topotecan;topoisomerase II inhibitors such as podophyllotoxin, amsacrine, etoposide, teniposide, losoxantrone and actinomycin;
  hormones and hormone antagonists, including androgens such as fluoxymesterone and testolactone,
  anti-androgens such as bicalutamide, cyproterone, flutamide, and nilutamide;
  corticosteroids such as dexamethasone and prednisone;
  aromatase inhibitors such as aminoglutethimide, anastrozole, exemestane, formestane, and letrozole;
  estrogens such as diethylstilbestrol;
  anti-estrogens such as fulvestrant, raloxifene, tamoxifen, and toremifine;
  luteinising hormone-releasing hormone (LHRH) agonists and antagonists such as abarelix, buserelin, goserelin, leuprolide, histrelin, desorelin, nafarelin acetate and triptorelin;
  progestins such as medroxyprogesterone acetate and megestrol acetate, and thyroid hormones such as levothyroxine and liothyronine;
  PKB pathway inhibitors, including perifosine, enzastaurin hydrochloride, and triciribine;
  PI3K inhibitors such as semaphore and SF1126;
  mTOR inhibitors such as rapamycin and analogues;
  CDK inhibitors, including seliciclib, alvocidib, and 7-hydroxystaurosporine;
  COX-2 inhibitors, including celecoxib;
  HDAC inhibitors, including trichostatin A, suberoylanilide hydroxamic acid, and chlamydocin;
  DNA methylase inhibitors, including temozolomide; and
  miscellaneous agents, including altretamine, arsenic trioxide, thalidomide, lenalidomide, gallium nitrate, levamisole, mitotane, hydroxyurea, octreotide, procarbazine, suramin, photodynamic compounds such as methoxsalen and sodium porfimer, and proteasome inhibitors such as bortezomib.

Molecular Targeted Therapy Agents Including:
functional therapeutic agents, e.g., gene therapy agents;
antisense therapy agents;

tyrosine kinase inhibitors such as erlotinib hydrochloride, gefitinib, imatinib mesylate, and semaxanib;
RAF inhibitors such as sorafenib;
gene expression modulators such as the retinoids and rexinoids, for example adapalene, bexarotene, trans-retinoic acid, 9-cis-retinoic acid, and N-(4-hydroxyphenyl)retinamide;
phenotype-directed therapy agents, including monoclonal antibodies such as alemtuzumab, bevacizumab, cetuximab, ibritumomab tiuxetan, rituximab, and trastuzumab;
immunotoxins such as emtansine, radioimmunoconjugates such as I-tositumobab, binding agents, such as aptamers, targeting any one of the molecular targets herein described,
and
cancer vaccines.
Biologic therapy agents including:
interferons such as interferon-[alpha]2a and interferon-[alpha]2b, and interleukins such as aldesleukin, denileukin diftitox, and oprelvekin. Axl inhibiting agents including 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine (BGB324/R428), CH5451098 (Roche) and Axl inhibitors described in PCT/US07/089177, PCT/US2010/021275 and PCT/EP2011/004451, incorporated herein by reference.

In addition to these agents intended to act against cancer cells, anticancer therapies include the use of protective or adjunctive agents, including:
cytoprotective agents such as amifostine, and dexrazoxane;
phosphonates such as pamidronate and zoledronic acid; and
stimulating factors such as epoetin, darbeopetin, filgrastim, PEG-filgrastim, and sargramostim.

Many combination chemotherapeutic regimens are known to the art, such as combinations of carboplatin/paclitaxel, capecitabine/docetaxel, fluorauracil/levamisole, fluorauracil/leucovorin, methotrexate/leucovorin, and trastuzumab/paclitaxel, alone or in further combination with carboplatin, and the like.

Throughout the specification, preferably the methods described herein are performed in vitro or ex vivo.

The present invention provides a method comprising causing or allowing binding of an antibody as provided herein to Axl. As noted, such binding may take place in vivo, e.g. following administration of an antibody, or nucleic acid encoding an antibody, or it may take place in vitro, for example in ELISA, Western blot analysis, immunocytochemistry, immunohistochemistry, immunoprecipitation or affinity chromatography.

The amount of antibody bound to Axl receptor may be determined. Quantitation may be related to the amount of the antigen in a test sample, which may be of diagnostic interest.

The reactivity of antibody in a sample may be determined by any appropriate means. Radioimmunoassay (RIA) is one possibility. Radioactively labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

Further reporters include DNA tags. These tags may be readily quantified by, for example, qPCR.

The signals generated by individual antibody-reporter conjugates may be used to derive quantifiable absolute or relative data of the relevant antibody binding in samples (normal and test).

The present invention also provides the use of an antibody as above for measuring antigen levels in a competition assay, that is to say a method of measuring the level of antigen in a sample by employing an antibody as provided by the present invention in a competition assay. This may be where the physical separation of bound from unbound antigen is not required. Linking a reporter molecule to the antibody so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing an antibody according to the invention for example in a biosensor system.

The mode of determining binding is not a feature of the present invention and those skilled in the art are able to choose a suitable mode according to their preference and general knowledge.

The present invention further extends to an antibody which competes for binding to Axl with any antibody which both binds the antigen and comprises an antibody variable domain (either VH or VL or both) including a CDR with amino acid substantially as set out herein or a variable domain with amino acid sequence substantially as set out herein. Competition between the antibodies may be assayed easily in vitro, for example by tagging a specific reporter molecule to one binding member which can be detected in the presence of other untagged binding member(s), to enable identification of antibodies which bind the same epitope or an overlapping epitope. Competition may be determined for example using ELISA or flow cytometry. Alternatively, competing antibodies may be identified via surface plasmon resonance (SPR) technique using Biacore instrument, as described in Example 5.

In testing for competition, a peptide fragment of the antigen may be employed, especially a peptide including an epitope of interest. A peptide having the epitope sequence plus one or more amino acids at either end may be used.

Such a peptide may be said to "consist essentially" of the specified sequence. Antibodies according to the present invention may be such that their binding for antigen is inhibited by a peptide with or including the sequence given. In testing for this, a peptide with either sequence plus one or more amino acids may be used.

Antibodies which bind a specific peptide may be isolated for example from a phage display library by panning with the peptide(s).

The present invention further provides an isolated nucleic acid encoding an antibody of the present invention. Nucleic acid includes DNA and RNA. In a preferred aspect, the present invention provides a nucleic acid which codes for a CDR, VH or VL domain of the invention as defined above.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR, VH or VL domain, or antibody as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression, a VH or VL domain, or antibody may be isolated and/or purified using any suitable technique known in the art.

Antibodies, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of an origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast, baculovirus, and insect cell systems. Mammalian cell lines available in the art for expression of a heterologous polypeptide include Chinese hamster ovary cells (CHO), HeLa cells, baby hamster kidney (BHK) cells, NS0 and SP2/0 mouse myeloma cells, YB2/0 rat myeloma cells, human cell lines HEK-293 and PER.C6 and many others. A common, preferred bacterial host is E. coli.

The expression of antibodies and antibody fragments in prokaryotic cells such as E. coli is well established in the art. For a review, see for example Plückthun, A. Bio/Technology 9: 545-551 (1991). Expression in eukaryotic cells in culture is also available to those skilled in the art as an option for production of an antibody, see for reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate (Sambrook and Russell, 2001, Molecular Cloning: a Laboratory Manual: $3^{rd}$d edition, Cold Spring Harbor Laboratory Press). Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express an antibody or polypeptide as above.

Aspects and embodiments of the present invention will now be illustrated by way of example with reference to the following experimentation.

All documents cited anywhere in this specification are incorporated by reference.

STATEMENTS OF INVENTION

The following paragraphs describe a number of specifically envisioned embodiments and combinations of the present invention.

1 An antibody that binds Axl and which comprises:
an antibody VH domain selected from the group consisting of the 1H12 VH domain (SEQ ID NO.3) and a VH domain comprising a VH CDR3 with the amino acid sequence of SEQ ID NO.7 and optionally one or more VH CDR's with an amino acid sequence selected from SEQ ID NO.6 and SEQ ID NO.5; and/or
an antibody VL domain selected from the group consisting of the 1H12 VL domain (SEQ ID NO. 4) and a VL domain comprising one or more VL CDR's with an amino acid sequence selected from SEQ ID NO.8, SEQ ID NO.9 and SEQ ID NO.10.

2. An antibody according to paragraph 1 comprising an antibody VH domain comprising the VH CDR's with the amino acid sequences of SEQ ID NO.5, SEQ ID NO.6 and SEQ ID NO.7, which antibody competes for binding to Axl with an Axl binding domain of an antibody comprising the 1H12 VH domain (SEQ ID NO. 3) and the 1H12 VL domain (SEQ ID NO. 4).

3. An antibody according to paragraph 1 or paragraph 2 comprising the 1H12 VH domain (SEQ ID NO. 3).

4. An antibody according to paragraph 3 comprising the 1H12 VL domain (SEQ ID NO. 4)

5. A variant of an antibody according to any one of paragraphs 1 to 4, wherein the variant comprises one or more amino acid sequence alterations in one or more framework regions and/or one or more CDRs.

6. An antibody according to any one of paragraphs 1 to 5 that binds Axl with affinity equal to or better than the affinity of an Axl antigen-binding site formed by the 1H12 VH domain (SEQ ID NO. 3) and the 1H12 VL domain (SEQ ID NO. 4), the affinity of the antibody and the affinity of the antigen-binding site being as determined under the same conditions.

7. An antibody according to any one of paragraphs 1 to 6 that comprises an scFv antibody molecule.

8. An antibody according to any one of paragraphs 1 to 6 that comprises an antibody constant region.

9. An antibody according to paragraph 8 that comprises a whole antibody.

10. An antibody according to any one of paragraphs 1 to 6 wherein the antibody is an antigen-binding antibody fragment, such as a single domain antibody, Fv, scFv, dsFv, Fd, Fab, F(ab')2, minibody, diabody, single-chain diabody, tandem scFv, TandAb, bi-body, tri-body, kappa(lambda)-body, BiTE, DVD-Ig, SIP, SMIP, or DART.

11. An antibody according to any one of paragraphs 1 to 10 which comprises additional amino acids providing a further functional characteristic in addition to the ability to bind antigen.

12. An antibody according to any one of paragraphs 1 to 11 which binds Axl with a $K_D$ no greater than $5 \times 10^{-11}$ M.

13. An antibody according to any one of paragraphs 1 to 11 which binds Axl with a $K_D$ no greater than $1.5 \times 10^{-11}$ M.

14. An antibody according to any one of paragraphs 1 to 13 which binds Axl with a $k_{off}$ no greater than $2 \times 10^{-5}$ s$^{-1}$.

15. An antibody according to any one of paragraphs 1 to 14 which binds Axl with a $k_{off}$ no greater than $3 \times 10^{-6}$ s$^{-1}$.

16. An antibody according to any one of paragraphs 1 to 15 wherein the Axl is human Axl.

17. An antibody according to any one of paragraphs 1 to 16 which specifically binds primate Axl.

18. An antibody according to any one of paragraphs 1 to 17 which:
(i) binds murine Axl with a $K_D$ greater than $10^{-3}$ M;
(ii) binds human Mer with a $K_D$ greater than $10^{-3}$ M; and/or
(iii) binds human Tyro3 with a $K_D$ greater than $10^{-3}$ M.

19. An antibody according to any one of paragraphs 1 to 18 wherein the antibody is an Axl agonist.

20. An antibody according to paragraph 19 wherein Axl signalling is at least 10% greater.

21. An antibody according to any one of paragraphs 1 to 20 wherein the antibody is a chimeric antibody.

22. An antibody according to any one of paragraphs 1 to 20 wherein the antibody is a humanised antibody.

23. An antibody according to any one of paragraphs 1 to 22 wherein the antibody binds:
(i) the same epitope as the 1H12 antibody, or
(ii) an epitope which overlaps with the epitope bound by the 1H12 antibody.

24. An antibody according to any one of paragraphs 1 to 23 wherein the antibody is internalised following binding to Axl present on a cell surface.

25. An antibody according to any one of paragraphs 1 to 24 which is conjugated to a detectable label, enzyme, or toxin, optionally via a peptidyl bond or linker.

26. An antibody according to paragraph 25 wherein the toxin is selected from the group comprising MMAE and MMAF.

27. An antibody according to paragraph 25 wherein the detectable label is FITC.

28. An isolated nucleic acid which comprises a nucleotide sequence encoding an antibody or antibody VH or VL domain of an antibody according to any one of paragraphs 1 to 24.

29. A host cell transformed with nucleic acid according to paragraph 28.

30. A method of producing a antibody or antibody VH or VL domain, the method comprising culturing host cells according to paragraph 29 under conditions for production of said antibody or antibody VH or VL domain.

31. A method according to paragraph 30 further comprising isolating and/or purifying said antibody or antibody VH or VL variable domain.

32. A method according to paragraph 30 or paragraph 31 further comprising formulating the antibody or antibody VH or VL variable domain into a composition including at least one additional component.

33. A method of obtaining an antibody that binds Axl, the method comprising
providing by way of addition, deletion, substitution or insertion of one or more amino acids in the amino acid sequence of the 1H12 VH domain (SEQ ID NO. 3) one or more VH domains each of which is an amino acid sequence variant of the 1H12 VH domain, optionally combining one or more VH domain amino acid sequence variants thus provided with one or more VL domains to provide one or more VH/VL combinations; and/or
providing by way of addition, deletion, substitution or insertion of one or more amino acids in the amino acid sequence of the 1H12 VL domain (SEQ ID NO. 4) a VL domain which is an amino acid sequence variant of the 1H12 VL domain, and combining one or more VL domain amino acid sequence variants thus provided with one or more VH domains to provide one or more VH/VL domain combinations;
and
testing the VH domain amino acid sequence variants or VH/VL combination or combinations for to identify a antibody that binds Axl.

34. A method of obtaining an antibody that binds Axl, which method comprises:
providing starting nucleic acids encoding one or more VH domains which either comprise a CDR3 to be replaced or lack a CDR3 encoding region, and combining said starting nucleic acid with a donor nucleic acid encoding the VH CDR3 amino acid sequence of SEQ ID NO.7 such that said donor nucleic acid is inserted into the CDR3 region in the starting nucleic acid, so as to provide product nucleic acids encoding VH domains; or
providing starting nucleic acids encoding one or more VL domains which either comprise a CDR3 to be replaced or lack a CDR3 encoding region, and combining said starting nucleic acid with a donor nucleic acid encoding the VL CDR3 amino acid sequence of SEQ ID NO.10 such that said donor nucleic acid is inserted into the CDR3 region in the starting nucleic acid, so as to provide product nucleic acids encoding VL domains;
expressing the nucleic acids of said product nucleic acids encoding VH domains and optionally combining the VH domains thus produced with one or more VL domains to provide VH/VL combinations, and/or expressing the nucleic acids of said product nucleic acids encoding VL domains and combining the VL domains thus produced with one or more VH domains to provide VH/VL combinations;

selecting an antibody comprising a VH domain or a VH/VL combination that binds Axl; and recovering said antibody that binds Axl and/or nucleic acid encoding the antibody that binds Axl.

35. A method according to paragraph 33 or paragraph 34 wherein the antibody that binds Axl is an antibody fragment comprising a VH domain and a VL domain.

36. A method according to paragraph 35 wherein the antibody fragment is an scFv antibody molecule.

37. A method according to paragraph 35 wherein the antibody fragment is an Fab antibody molecule.

38. A method according to paragraph 36 or paragraph 37 further comprising providing the VH domain and/or the VL domain of the antibody fragment in a whole antibody.

39. A method according to any one of paragraphs 33 to 38 further comprising formulating the antibody that binds Axl or an antibody VH or VL variable domain of the antibody that binds Axl into a composition including at least one additional component.

40. A method according to any one of paragraphs 30 to 39 further comprising binding a antibody that binds Axl to Axl or a fragment of Axl.

41. A method comprising binding an antibody that binds Axl according to any one of paragraphs 1 to 27 to Axl or a fragment of Axl.

42. A method according to paragraph 40 or paragraph 41 wherein said binding takes place in vitro.

43. A method according to any one of paragraphs 40 to 42 comprising determining the amount of binding of antibody to Axl or a fragment of Axl.

44. A method according to any one of paragraphs 30 to 39 further comprising use of the antibody in the manufacture of a medicament for treatment of a disease or disorder characterised by overexpression of Axl.

45. An antibody according to any one of paragraphs 1 to 27, or an immunoconjugate thereof, in combination with another therapeutic agent.

46. A composition comprising an antibody according to any one of paragraphs 1 to 27, or an immunoconjugate thereof, in conjunction with a pharmaceutically acceptable excipient.

47. A composition according to paragraph 46 further comprising another therapeutic agent.

48. An antibody according to paragraph 45 or a composition according to paragraph 47 wherein the other therapeutic agent is an immune checkpoint modulator (ICM), such as an immune checkpoint inhibitor (ICI).

49. An antibody according to any one of paragraphs 1 to 27, 45, or 48, or the composition according to any one of paragraphs 46 to 48, for use in a method of treatment.

50. An antibody or composition according to paragraph 49 for use in a method of treating a proliferative disease.

51. An antibody or composition according to paragraph 40 where the proliferative disease is cancer, such as AML.

52. An antibody or composition according to paragraph 51 where the cancer is metastatic cancer.

53. Use of an antibody according to any one of paragraphs 1 to 27, 45, or 48, or the composition according to any one of paragraphs 46 to 48, in the manufacture of a medicament for treatment of a disease or disorder characterised by overexpression of Axl.

54. A method of treatment of a disease or disorder characterised by overexpression of Axl, the method comprising administering an antibody according to any one of paragraphs 1 to 27, 45, or 48, or the composition according to any one of paragraphs 46 to 48, to a patient with the disease or disorder or at risk of developing the disease or disorder.

55. A method according to paragraph 50 wherein the antibody directs the delivery of a pharmaceutical composition to target metastatic cancer cells.

56. Use of an antibody according to any one of paragraphs 1 to 27, 45, or 48 and one or more reagents that allow determination of the binding of said antibody to metastatic cancer cells, in the manufacture of a diagnostic agent for the detection of a disease or disorder characterised by overexpression of Axl.

57. A method of diagnosis of a disease or disorder characterised by overexpression of Axl, the method comprising administering an antibody according to any one of paragraphs 1 to 27, 45, or 48, or the composition according to any one of paragraphs 46 to 48, and one or more reagents that allow determination of the binding of said antibody to metastatic cancer cells, to a patient with the disease or disorder or at risk of developing the disease or disorder.

58. A diagnostic kit comprising an antibody according to any one of paragraphs 1 to 27, 45, or 48 and one or more reagents that allow determination of the binding of said member to metastatic cancer cells.

59. A kit comprising an antibody according to any one of paragraphs 1 to 27, 45, or 48, or the composition according to any one of paragraphs 46 to 48.

60. A pharmaceutical composition comprising as active principle an antibody according to paragraphs 1 to 27 in an effective amount, in conjunction with a pharmaceutically acceptable excipient.

EXAMPLES

Example 1

Generation of Mouse Anti-Axl Monoclonal Antibody

Monoclonal antibodies (MAb) against human Axl receptor were generated by immunization of immunocompetent OF1 mice (Charles River) with a recombinant antigen comprising an extracellular domain of human Axl fused to human IgG1 Fc domain (rhAxl-Fc; R&D Systems).

Spleen cells from mice showing presence of rhAxl-specific antibodies in the blood were used for fusion with mouse myeloma cells according to standard protocols. The cells were cultured in plates ($10^5$ cells per well) with hypoxanthine-aminopterin-thymidine (HAT) medium for hybridoma selection. After twelve days of selection, the supernatants were harvested and tested for Axl binding in enzyme-linked immunosorbent assay (ELISA) and flow cytometry. Five positive clones, showing the highest antigen-binding activity after the second round of subcloning by limited dilution, were expanded for large scale antibody production in vitro. The MAbs were purified from the cell culture supernatants by Protein G affinity chromatography.

The antibody clone 1H12 showing specific binding to Axl$^+$ cells in flow cytometry (FIG. 1) was selected for further characterization.

For flow cytometry, the adherent cells in culture were washed with PBS, detached by trypsin (0.25%) treatment for 1 min and hitting culture dish for full detachment. Trypsin was quenched by adding into the tissue flask the complete medium followed by washing the cells with PBS. During the washing steps, the cells were collected by centrifugation at 200g for 5 min. The antibody was diluted for total concentration in PBS containing 0.02% bovine serum albumin (BSA). Cell staining was performed using 200 µL of cell suspension comprising $10^5$ cells for 20 min at room temperature. After two washing steps with PBS 0.02% BSA, the cells were resuspended in 200 µL and kept on ice before analysis on Accuri C6 flow cytometer (BD Biosciences).

Example 2

Mouse Monoclonal Antibody 1H12 does not Cross-React with Other Members of Human TAM Receptor Family All binding experiments were performed using Biacore 3000 instrument (GE Healthcare) at 25° C. The soluble recombinant antigens corresponding to the members of human TAM receptor family, Axl (rhAxl-Fc chimera; R&D Systems, Cat. no. 154-AL), Mer (rhMer-Fc chimera; R&D Systems, Cat. no. 891-MR) and Tyro3 (rhTyro3/Dtk-Fc chimera; R&D Systems, Cat. no. 859-DK) were immobilized on the surface of CM5 sensor chip using amine coupling at the surface density of 393.0, 303.6 and 364.0 resonance units (RU), respectively. The Biacore run was performed in an automatic mode using Binding analysis wizard. The sample containing MAb 1H12 at concentration 10 µg/mL in HBS-EP buffer (GE Healthcare) was injected over the surfaces with immobilized antigens at flow rate of 30 µL/min for 3 min (association) followed by 5 min dissociation.

Figure 2:
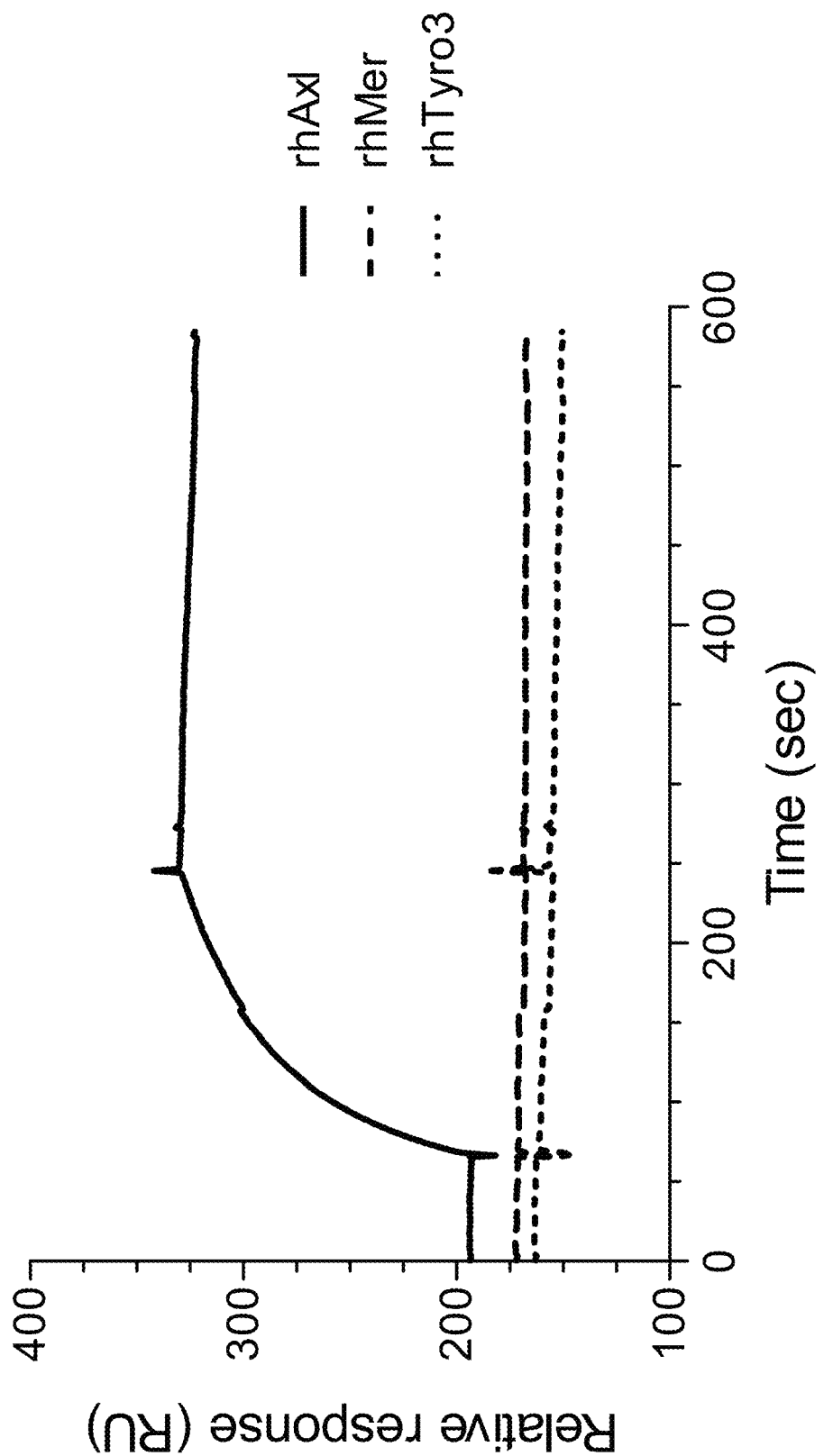

The results shown in FIG. 2 demonstrate specific interaction with human Axl and no binding to recombinant human Mer and Tyro3 antigens.

Example 3

Mouse Monoclonal Antibody 1H12 does not Cross-React with Mouse AXL

The binding experiments were performed using Biacore 3000 instrument (GE Healthcare) at 25° C. The soluble recombinant antigens corresponding to human Axl (rhAxl-Fc chimera; R&D Systems, Cat. no. 154-AL), mouse Axl (rmAxl-Fc chimera; R&D Systems, R&D Systems; Cat. no. 854-AX) and human Tyro3 (rhTyro3/Dtk-Fc chimera; R&D Systems, Cat. no. 859-DK) were immobilized on the surface of CM5 sensor chip using amine coupling at the surface density of 1,308.0, 2,115.9 and 1,429.0 RU, respectively. The Biacore run was performed in an automatic mode using Binding Analysis wizard.

The sample containing either MAb 1H12 or recombinant mouse (rm) Axl-ligand Gas6 (R&D Systems, Cat. no. 986-GS/CF) at concentration 10 µg/mL in HBS-EP buffer (GE Healthcare) was injected over the surfaces with immobilized antigens at flow rate of 30 µL/min for 3 min (association) followed by 5 min dissociation.

Figure 3:
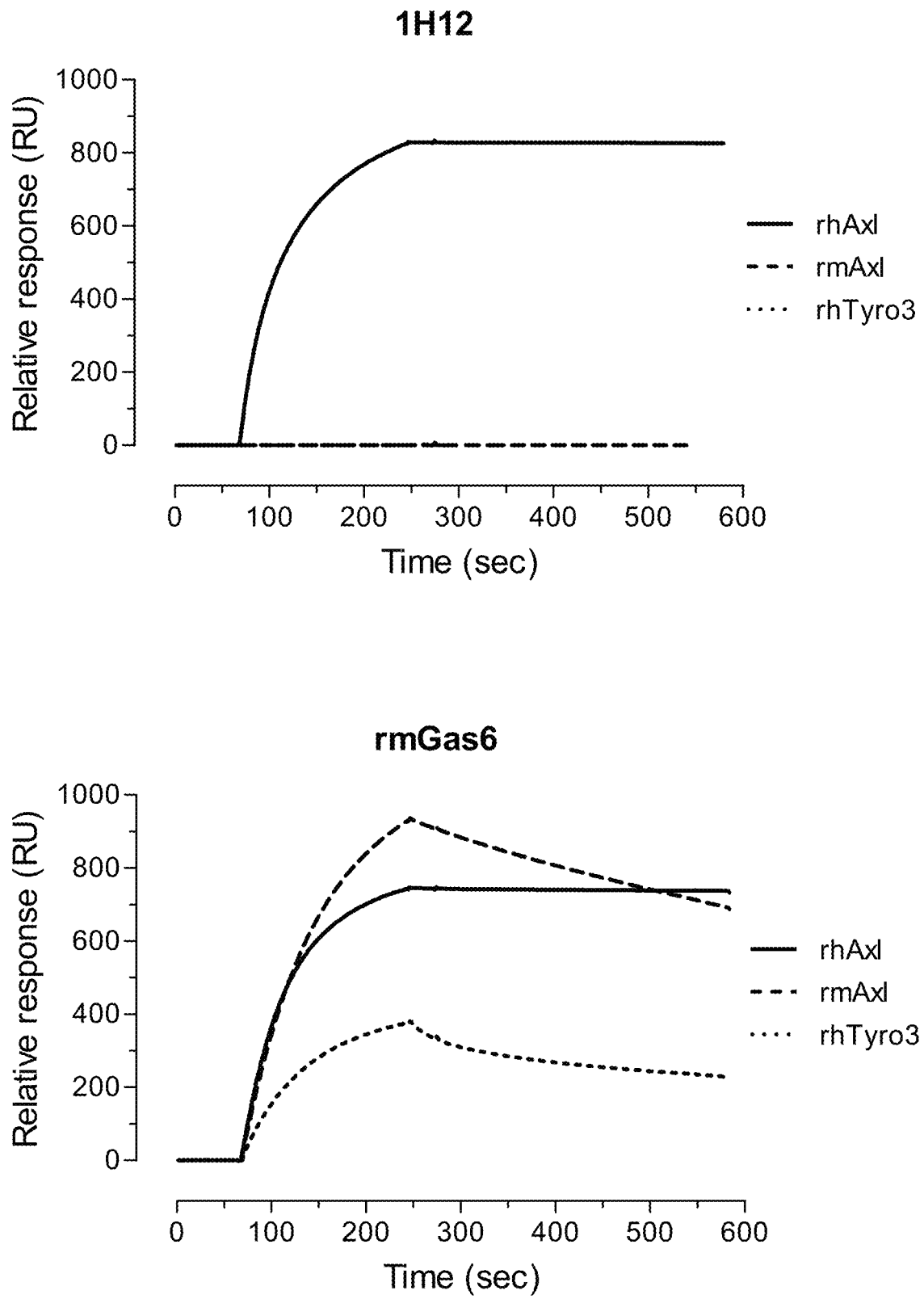

The results shown in FIG. 3 demonstrate specific interaction of MAb 1H12 with human Axl and no binding to recombinant mouse Axl and human Mer antigens (FIG. 3, upper panel). In contrast, mouse Gas6, used as a control, demonstrated strong binding to both human and mouse Axl and somewhat weaker binding to human Tyro3 (FIG. 3, lower panel).

Example 4

Affinity Determination of Mouse Monoclonal Antibody 1H12

Affinity determination of anti-Axl antibody 1H12 was performed at 25° C. by surface plasmon resonance measurements using Biacore 3000 instrument (GE Healthcare). As a solid antigen-coated surface, the sensor chip CM5 with immobilized rhAxl-Fc chimera (R&D Systems, Cat. no. 154-AL) at density 190 RU was used.

For the kinetics measurements, different concentrations of anti-Axl MAb 1H12 (from 1.3 to 666.7 nM) in HBS-EP buffer (Biacore, Cat. no. BR-1001-88) were injected at flow rate of 30 µL/min with 3 min injection time followed by 5 min dissociation (buffer alone). After each cycle, the surface was regenerated by 30 sec injection of a regeneration solution (10 mM HCl, 1 M NaCl) at flow rate 50 µL/min.

The mass transfer control experiments demonstrated absence of significant mass transfer limitations for MAb 1H12. An additional, linked reactions control experiment did not reveal linked reactions for MAb 1H12, since the dissociation phases were practically identical after injection for 1, 3 or 20 min or one analyte concentration (1.8 µM or 270 µg/mL). The kinetic association (on-rate, $k_{on}$) and dissociation (off-rate, $k_{off}$) rates were calculated using BIAevaluation software and 1:1 Langmuir binding model. The equilibrium dissociation constant ($K_D$) was calculated as the $k_{off}/k_{on}$ ratio. The half-life ($t_{1/2}$) of the formed antibody-antigen complexes was calculated as the $\ln2/k_{off}$ ratio.

Figure 4:
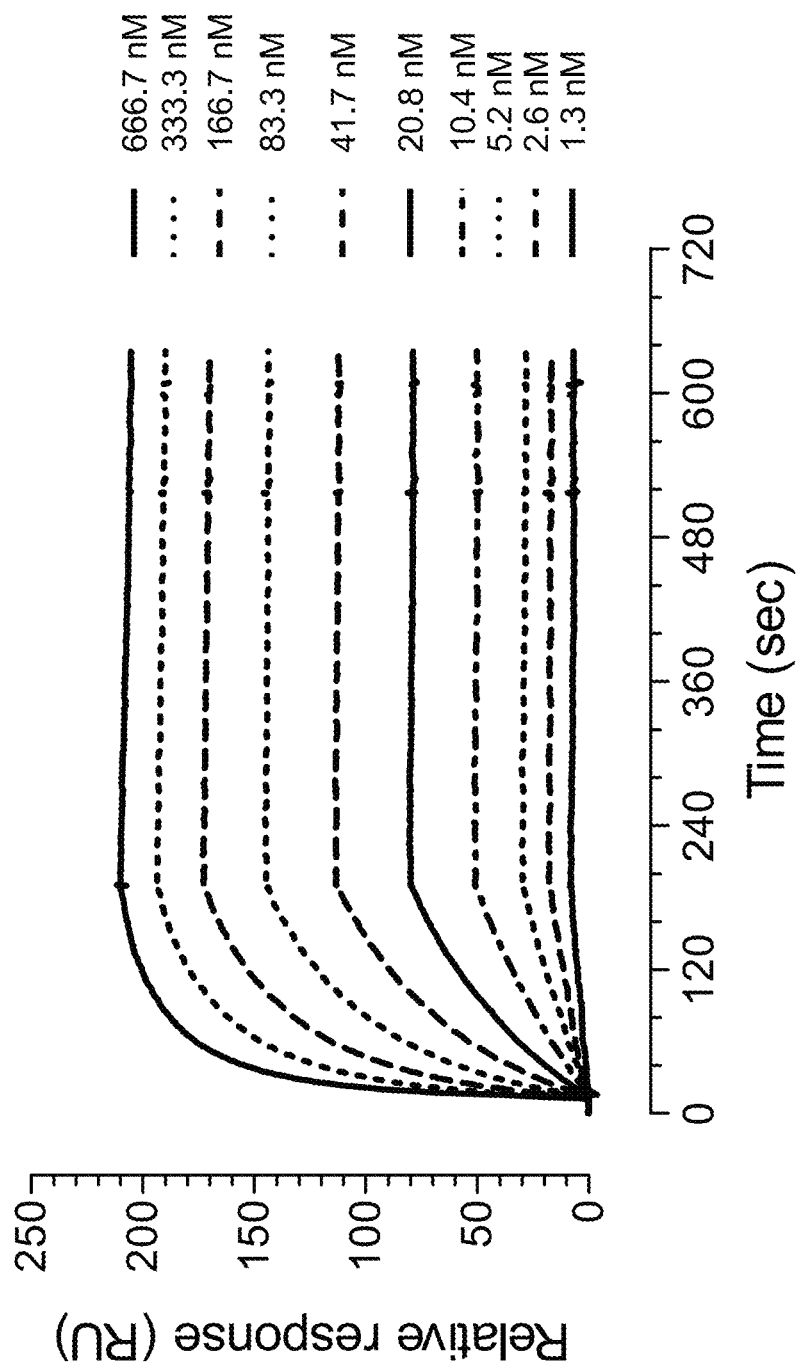

As shown in FIG. 4, the mouse MAb 1H12 demonstrated very high affinity ($K_D=4.98\times10^{-11}$ M) mainly due to a very slow dissociation rate ($k_{off}=1.07\times10^{-5}$ 1/s) which resulted in 18 hr half-life of the 1H12/Axl complex.

Example 5

Mouse Monoclonal Antibody 1H12 does not Block Binding of Gas6 to Axl

The competitive binding study was performed using Biacore 3000 instrument (GE Healthcare) and Binding Analysis wizard with several cycles of two samples injection. As a first sample, a saturating concentration of MAb 1H12 (1.8 µM or 270 µg/mL) was injected over the surface of the CM5 sensor chip coated with rhAxl-Fc (using amine coupling) for 3 min at flow rate of 30 µl/min followed by 2.5 min stabilization (HBS-EP buffer alone) before the injection of the second sample. The following second samples were used: recombinant human (rh) Gas6 (R&D Systems, Cat. no. 885-GS), recombinant mouse (rm) Gas6 (R&D Systems, Cat. no. 986-GS/CF) and a panel of anti-Axl antibodies (MAb1,2,3); all at concentration 25 µg/mL. As a control, MAb 1H12 was used as a second sample under the same conditions (25 µg/mL). The second sample was injected for 3 min, followed by 2.5 min stabilization (buffer alone) and regeneration of the surface by 30 sec injection of a regeneration solution (10 mM HCl, 1 M NaCl) at flow rate 50 µL/min.

Figure 5:
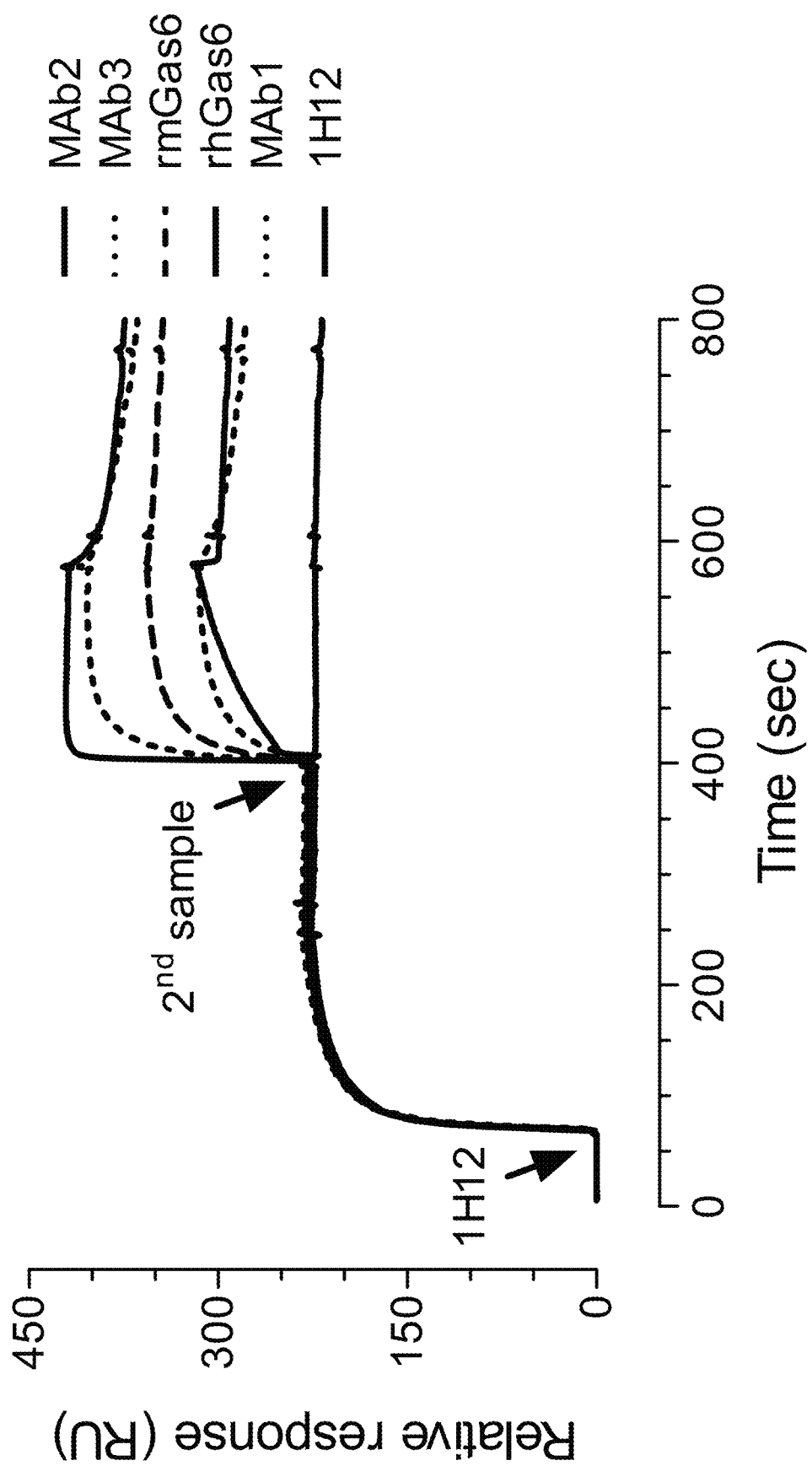

The results shown in FIG. 5 demonstrated that the MAb 1H12 did not compete for Axl binding with Gas6 (both human and mouse) and any other anti-Axl antibody used in the experiment.

Example 6

Mouse Monoclonal Antibody 1H12 Binds to Denatured Both Reduced and Non-Reduced Axl in Western Blot Analysis For Western blot analysis, the recombinant human (rh) Axl-Fc chimera (R&D Systems, Cat. no. 154-AL) with a predicted molecular mass of 71.7 kDa (corresponds to 100-110 kDa in SDS-PAGE under reducing conditions) and rhMer-Fc (R&D Systems, Cat. no. 891-MR) with a predicted mol. mass of 78.9 kDa (corresponds to 100-110 kDa in SDS-PAGE under reducing conditions) were used as antigens. The samples containing the antigens were denatured in presence or absence of the reducing agent (Life Technologies) and loaded into the wells of NuPAGE 3-8% Tris-Acetate polyacrylamide (PAA) gel, 1.0 mm×12 well (Invitrogen). As the molecular weight markers, SeeBlue Plus2 Prestained MW markers (Novex LC5925) were used.

The electrophoresis was performed using Tris-Acetate SDS running buffer under the recommended conditions (Life Technologies) and the proteins were transfer on nitrocellulose membrane, as described for 2 gels in a manual for XCell II™ Blot Module (Invitrogen) using the transfer buffer with 20% methanol. The membrane was incubated in 10 mL of blocking buffer, TBS/0.1% Tween20 (TBST) with 5% skimmed milk, for 1 hr at room temperature followed by overnight incubation in 5 mL of incubation buffer (TBST with 3% skimmed milk) containing 1 µg/mL MAb 1H12 at 4° C. The membrane was washed three times for 5 min each with 10 mL of TBST followed by 1 hr incubation with goat-anti mouse IgG (H+L) HRP-conjugated secondary antibody (1:3000) in 5 mL of incubation buffer with gentle rolling at room temperature. Afterwards, the membrane was washed three times for 5 min in 10 mL of TBST and twice with 10 mL of TBS buffer. The membrane was incubated with 1 mL ECL substrate for 1 min at room temperature. The excess of substrate solution was aspirated the blot was developed using ChemiDoc™ XRS+ imager (Bio Rad) and Image lab software.

Figure 6:
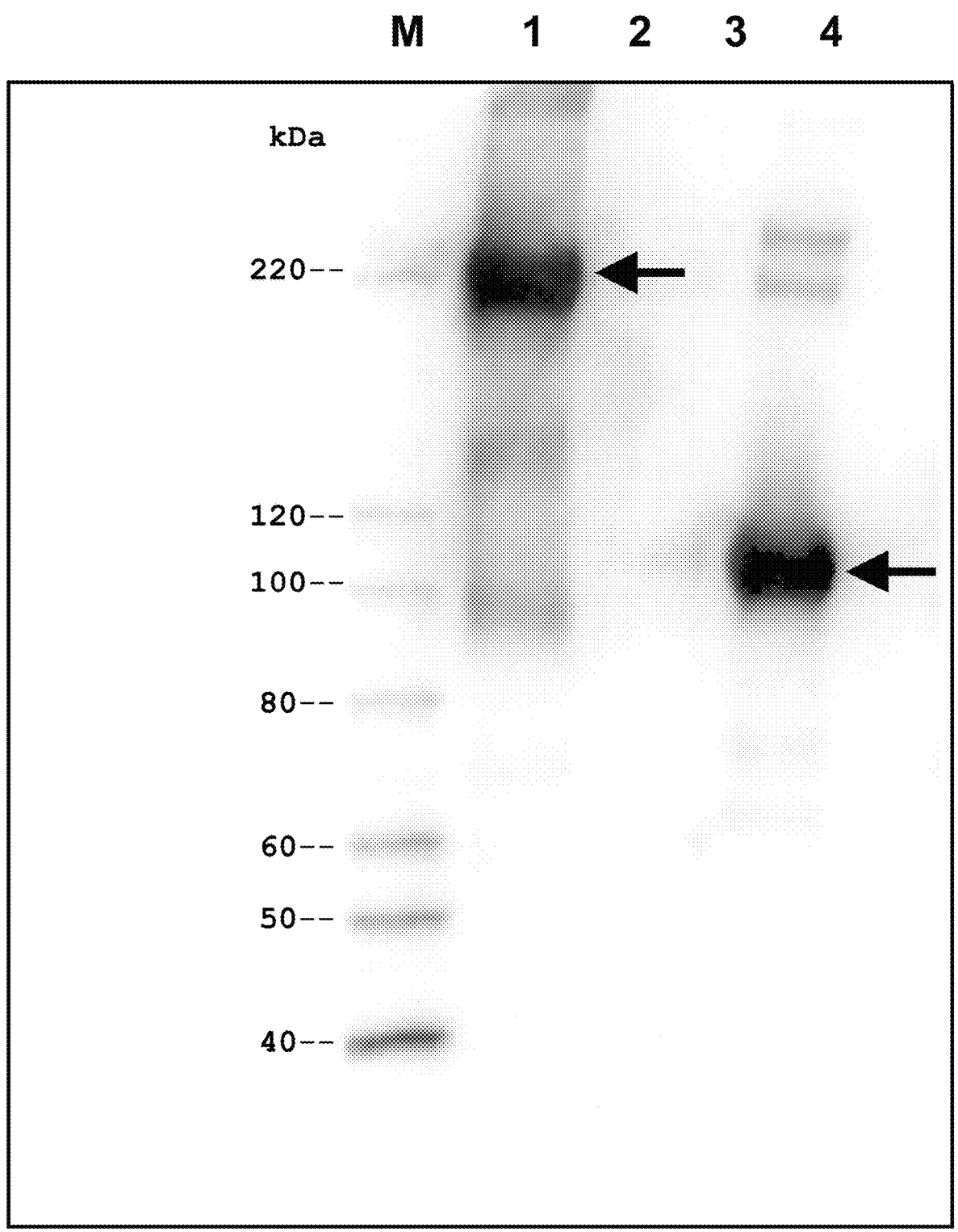

The results shown in FIG. 6 demonstrated that the antibody 1H12 specifically interacts with both reduced and non-reduced denatured Axl antigen. No binding to rhMer-Fc was detected. The results indicate the MAb 1H12 recognizes linear epitope on extracellular part of Axl receptor.

Example 7

Mouse Monoclonal Antibody 1H12 Binds To Denatured Both Reduced and Non-Reduced Axl Receptor Expressed on Cell Surface in its Natural Environment Cell lysates from both Axl$^+$ and Axl$^-$ cell lines, NCl—H1299 (non-small cell lung carcinoma, NSCLC) and LNCaP (prostatic adenocarcinoma), respectively, were prepared according to the standard protocols. The cell lysate aliquots were denatured in presence or absence of the reducing agent (Life Technologies) and loaded into the wells of NuPAGE 3-8% Tris-Acetate polyacrylamide (PAA) gel, 1.0 mm×12 well (Invitrogen). The SDS-PAGE and Western blot analysis were performed essentially as described in EXAMPLE 6.

Figure 7:
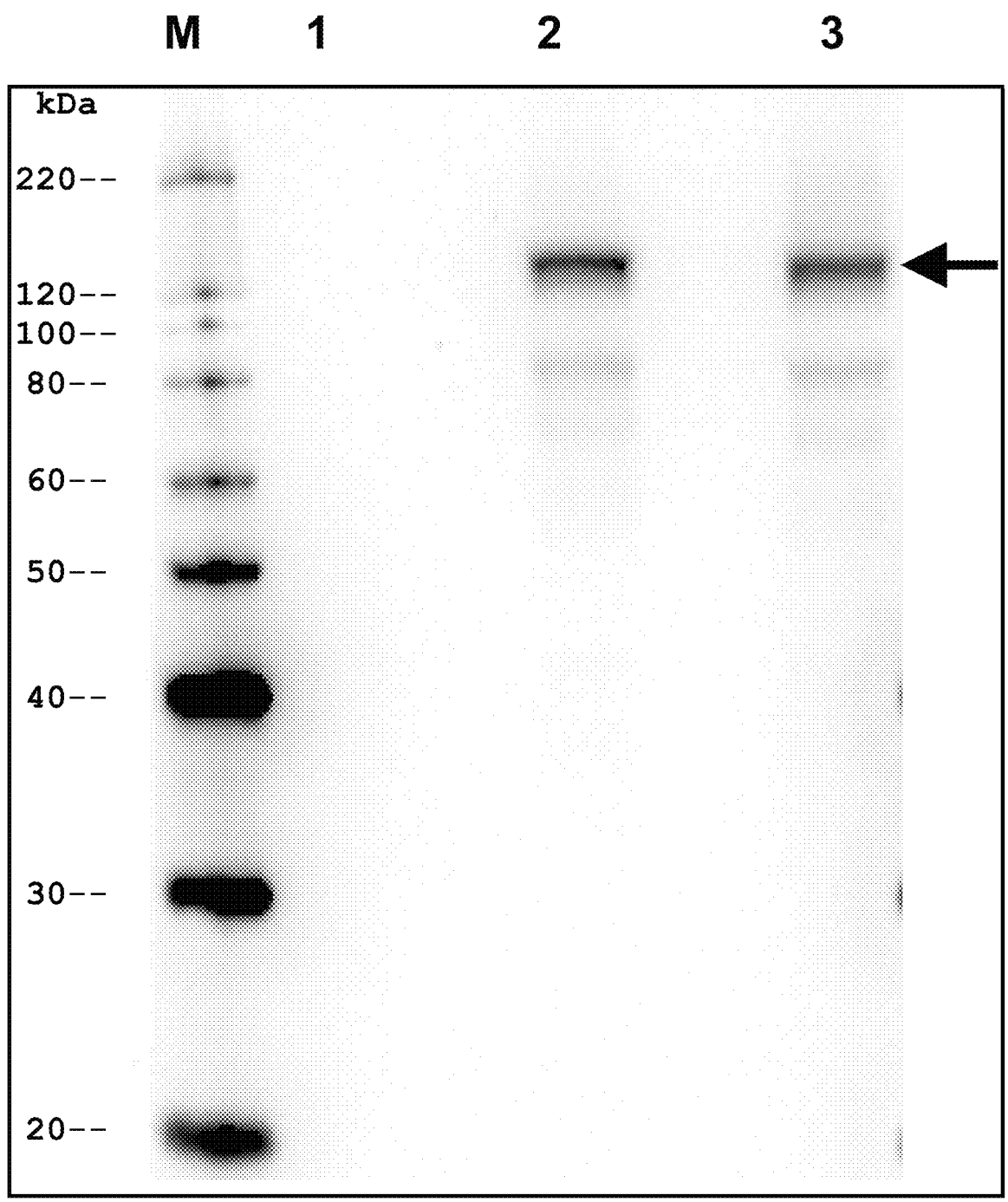

The results shown in FIG. 7 demonstrated specific interaction of MAb 1H12 with Axl receptor (both reduced and non-reduced) present in Axl$^+$ NCl—H1299 cells. No interaction with other cellular proteins present in either Axl$^+$ or Axl$^-$ cells was observed.

Example 8

Sequencing of Mouse Monoclonal Antibody 1H12

The hybridoma 1H12 cells were propagated under the standard conditions. 5×10$^6$ cells were used for mRNA isolation and cDNA synthesis according to the standard protocols. For PCR amplification of the genes encoding heavy and light chain variable regions (VH and VL, respectively), Mouse IgG Library Primer Set (Progen, Heidelberg, Germany, Cat. no. F2010) was used. PCR amplification using different primer combinations resulted in 14 sequences from PCR using 7 different primer combinations for the VH gene and in 7 sequences from PCR using 4 different primer combinations for the VL gene. The sequences of the clones VH5 C9-3 and Vκ4 G4-1 were selected for further work on the basis of highest homology with the corresponding germline sequences, as determined by nucleotide alignment with IMGT database.

The amino acid sequences of the 1H12 VH and VL domains are shown in FIG. 8.

Example 9

Anti-Axl Mouse Monoclonal Antibody 1H12 Showed Weak or no Reaction with Normal Human Tissues in Immunohistochemistry In a validation experiment, the optimal protocol and concentration for the antibody 1H12 was determined. For this work, frozen pellets of Axl$^+$ and Axl$^-$ cells were used. The antibody was tested at concentrations from 0.05 µg/mL to 16.0 µg/mL (16, 8, 4, 2, 1, 0.5, 0.1, and 0.05 µg/mL). The MAb 1H12 showed moderate to strong reaction in the Axl$^+$ cells from 8 down to 1 µg/mL; at 0.5 µg/mL the reaction was moderate. The optimal concentration of 1 µg/mL was, therefore, set to be used in the tissue cross-reactivity (TCR) study. At this concentration, no reaction was seen in the Axl-negative cells.

The TCR study was performed using commercial frozen tissue microarrays (TMA) purchased from BioChain (prod. no. T6234701-2). All tissues were delivered from BioChain as cryo-sectioned, acetone-fixed frozen TMA. Experiments were performed as follows: the cryo-sectioning (8 µm) was air-dried at room temperature overnight, and fixed in acetone for 10 min before they were blocked in 5% goat normal serum (Jackson ImmunoResearch, 005-000-121) for 30 min. The sections were then stained with a primary antibody (1H12) in PBS with 5% goat normal serum for 1 hr, before they were washed three times in PBS. Subsequently, the sections were stained with EnVision mouse (Dako, K4001) for 30 min. Finally, the sections were washed three times in Tris-HCl, before they were stained with 3,3'-Diaminobenzidine (DAB) stain for 5 min. Images were taken using HTX imaging. Staining intensity was judged as: negative (0), weak reaction (1+), moderate reaction (2+), or strong reaction (3+). The results of normal human TCR are shown in TABLE 2.

The antibody 1H12 demonstrated weak-to-moderate or moderate reaction in cells of lymph node and spleen (membrane staining). The local moderate reaction was also seen in live—possibly in Kuppfer cells (membrane staining). Some local moderate or strong intracellular reaction was seen in epithelial cells of pancreas. The following tissues showed no specific positive staining: adrenal, bone marrow, various brain tissues and spinal cord, colon, endothelium/aorta, esophagus, fallopian tube, heart, kidney, lung, ovary, placenta, prostate, skin, spinal cord, striated muscle, stomach, testis, thymus, thyroid, ureter and uterus.

TABLE 2

| Tissue | Binding of MAb 1H12 |
|---|---|
| Adrenal (1) | Negative |
| Adrenal (2) | Negative |
| Adrenal (3) | Negative |
| Bone marrow (1) | 1-2+ background in some cell type |
| Bone marrow (2) | 1-2+ background in some cell type |
| Bone marrow (3) | 1-2+ background in some cell type |
| Breast (1) | Negative |
| Breast (2) | Negative |
| Breast (3) | Negative |
| Brain cerebellum (1) | Negative |
| Brain cerebellum (2) | Negative |
| Brain cerebellum (3) | Negative |
| Brain cortex (1) | Negative |
| Brain cortex (2) | Negative |
| Brain cortex (3) | Negative |
| Brain pituitary (1) | Negative |
| Brain pituitary (2) | Negative |
| Brain pituitary (3) | Negative |
| Colon (1) | 2-3+ in mucin of epithelial cells (unspecific) |
| Colon (2) | Negative (no epithelium in section) |
| Colon (3) | Negative (no epithelium in section) |
| Endothelium, aorta (1) | Negative |
| Endothelium, aorta (2) | Negative |
| Endothelium, aorta (3) | Negative |
| Esophagus (1) | Negative |
| Esophagus (2) | Negative |
| Esophagus (3) | Negative |
| Fallopian tube (1) | Negative |
| Fallopian tube (2) | Negative |
| Fallopian tube (3) | Negative |
| Heart (1) | Negative (some local unspecific background) |
| Heart (2) | Negative (some local unspecific background) |
| Heart (3) | Negative (some local unspecific background) |
| Kidney (1) | Negative (some unspecific background) |
| Kidney (2) | Negative (some unspecific background) |
| Kidney (3) | Negative (some unspecific background) |
| Liver (1) | 2+, possibly in Kuppfer macrophages |
| Liver (2) | 2+, possibly in Kuppfer macrophages |
| Liver (3) | 2+, possibly in Kuppfer macrophages |
| Lung (1) | 2-3+ local, probably unspecific |
| Lung (2) | 2-3+ local, probably unspecific |
| Lung (3) | 2-3+ local, probably unspecific |
| Lymph node (1) | 1-2+ in many cells |
| Lymph node (2) | 1-2+ in many cells |
| Lymph node (3) | 1-2+ in many cells |
| Ovary (1) | Negative |
| Ovary (2) | Negative |
| Ovary (3) | Negative |
| Pancreas (1) | 2+ local in epithelial cells |
| Pancreas (2) | Negative |
| Pancreas (3) | 3+ local |
| Placenta (1) | Negative |
| Placenta (2) | Negative |
| Placenta (3) | Negative |
| Prostate (1) | Negative |
| Prostate (2) | Negative |
| Prostate (3) | Negative |
| Skin (1) | Negative |
| Skin (2) | Negative |
| Skin (3) | Negative |
| Spinal cord (1) | Negative |
| Spinal cord (2) | Negative |
| Spinal cord (3) | Negative |
| Spleen (1) | 2+ in many cells |
| Spleen (2) | 2+ in many cells |
| Spleen (3) | 2+ in many cells |
| Striated muscle (1) | Negative |
| Striated muscle (2) | Negative |
| Striated muscle (3) | Negative |
| Stomach (1) | Negative |
| Stomach (2) | Negative |
| Stomach (3) | Negative |
| Testis (1) | Negative |
| Testis (2) | Negative |
| Testis (3) | Negative |
| Thymus (1) | Negative |
| Thymus (2) | Negative |
| Thymus (3) | Negative |
| Thyroid (1) | Negative |
| Thyroid (2) | Negative |
| Thyroid, (3) | Negative |
| Ureter (1) | Negative |
| Ureter (2) | Negative |
| Ureter (3) | Negative |
| Uterus, endometrium (1) | Negative |
| Uterus, endometrium (2) | Negative |
| Uterus, endometrium (3) | Negative |
| Uterus, cervix (1) | Negative |
| Uterus, cervix (2) | Negative |
| Uterus, cervix (3) | Negative |

Example 10

Generation and Testing Chimeric Monoclonal Antibody 1H12

Figure 9:
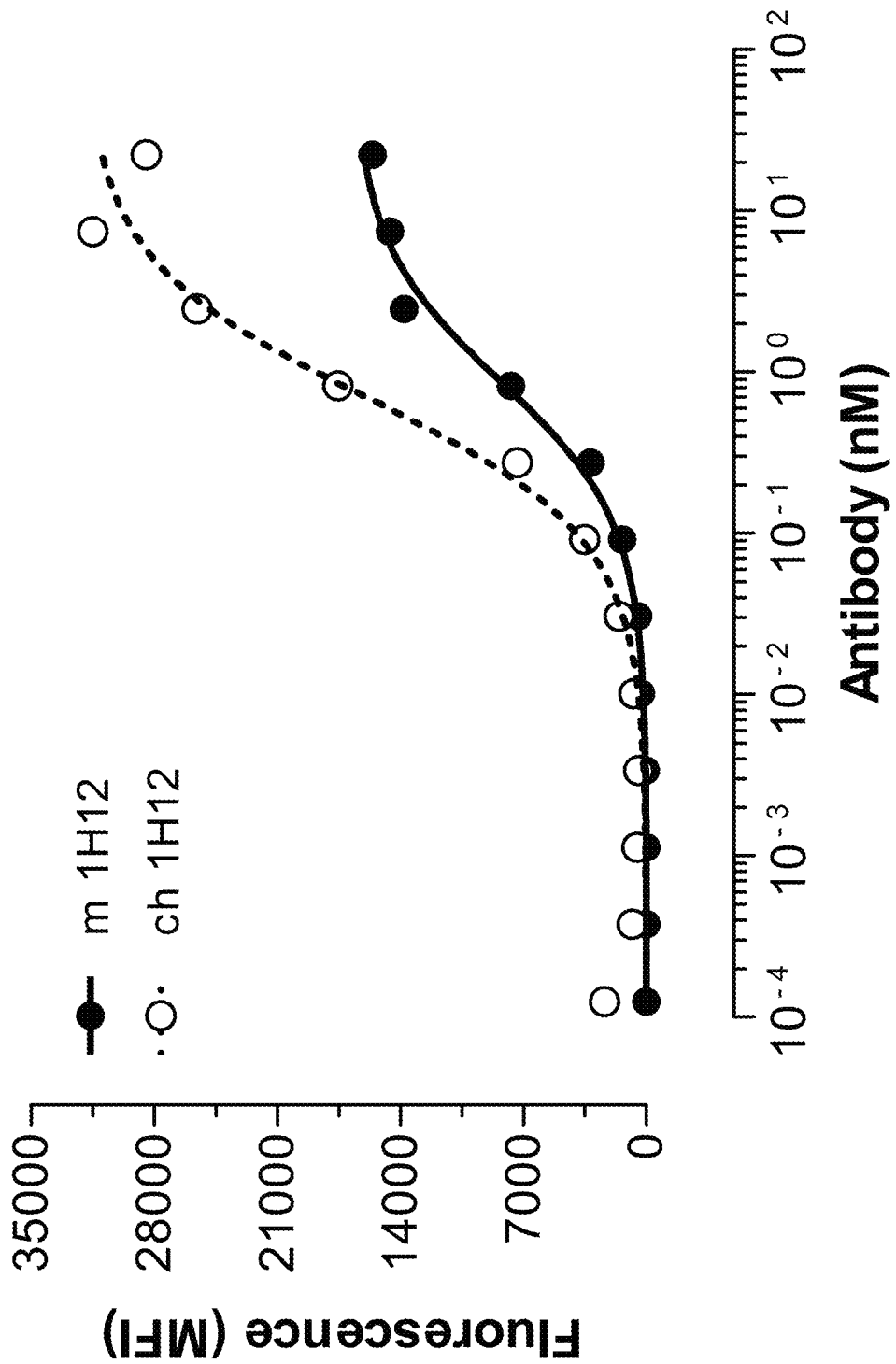

The VH and VL sequences retrieved from the murine hybridoma 1H12 were used for generation of the synthetic genes with codon optimization for expression in mammalian cells (GeneArt). These mouse VH and VL genes were ligated in frame with the genetic elements encoding constant domains of the human IgG1 heavy and light (C-kappa) chains, respectively, in an expression vector suitable for antibody production in mammalian cells. Production of the chimeric (mouse variable/human constant) IgG1 antibodies was achieved by transient expression in Chinese Hamster Ovary (CHO) cells followed by purification using Protein A affinity chromatography. The purified chimeric antibody (>95% purity) was analyzed for binding to Axl-positive breast cancer cell line MDA-MB-231 in flow cytometry. For comparison, the parental mouse MAb 1H12 was used. For flow cytometry, the adherent cells in culture were washed with PBS, detached by treatment with trypsin (0.25%) for 1 min and hitting culture dish for full detachment. Trypsin was quenched by adding into the tissue flask the complete medium followed by washing the cells with PBS. During the washing steps, the cells were collected by centrifugation at 200g for 5 min. The antibody was diluted for total concentration in PBS containing 0.02% bovine serum albumin (BSA). Cell staining was performed using 200 μL of cell suspension comprising $10^5$ cells for 20 min at room temperature. The cell-bound antibodies were detected with APC-conjugated donkey anti-human or anti-mouse, respectively, IgG (H+L) F(ab')$_2$ fragments (Jackson ImmunoResearch). After two washing steps with PBS/0.02% BSA, the cells were resuspended in 200 μL and kept on ice before analysis on Accuri C6 flow cytometer (BD Biosciences). The results shown in FIG. 9 demonstrated strong binding of the chimeric antibody to the MDA-MB-231 cells.

Example 11

Affinity Determination of Chimeric Monoclonal Antibody ch1H12

Affinity determination of anti-Axl chimeric (mouse variable/human constant IgG1) antibody ch1H12 was performed at 25° C. by surface plasmon resonance measurements using Biacore 3000 instrument (GE Healthcare). As a solid antigen-coated surface, the sensor chip CM5 with immobilized rhAxl-Fc chimera (R&D Systems, Cat. no. 154-AL) at density 190 RU was used.

For the kinetics measurements, different concentrations of anti-Axl chimeric MAb ch1H12 (from 1.3 to 666.7 nM) in HBS-EP buffer (Biacore, Cat. no. BR-1001-88) were injected at flow rate of 30 µL/min with 3 min injection time followed by 5 min dissociation (buffer alone). After each cycle, the surface was regenerated by 30 sec injection of a regeneration solution (10 mM HCl, 1 M NaCl) at flow rate 50 µL/min.

The mass transfer control experiments demonstrated absence of significant mass transfer limitations for MAb ch1H12. The kinetic association (on-rate, $k_{on}$) and dissociation (off-rate, $k_{off}$) rates were calculated using BIAevaluation software and 1:1 Langmuir binding model. The equilibrium dissociation constant ($K_D$) was calculated as the $k_{off}/k_{on}$ ratio. The half-life ($t_{1/2}$) of the formed antibody-antigen complexes was calculated as the $ln2/k_{off}$ ratio.

Figure 10:
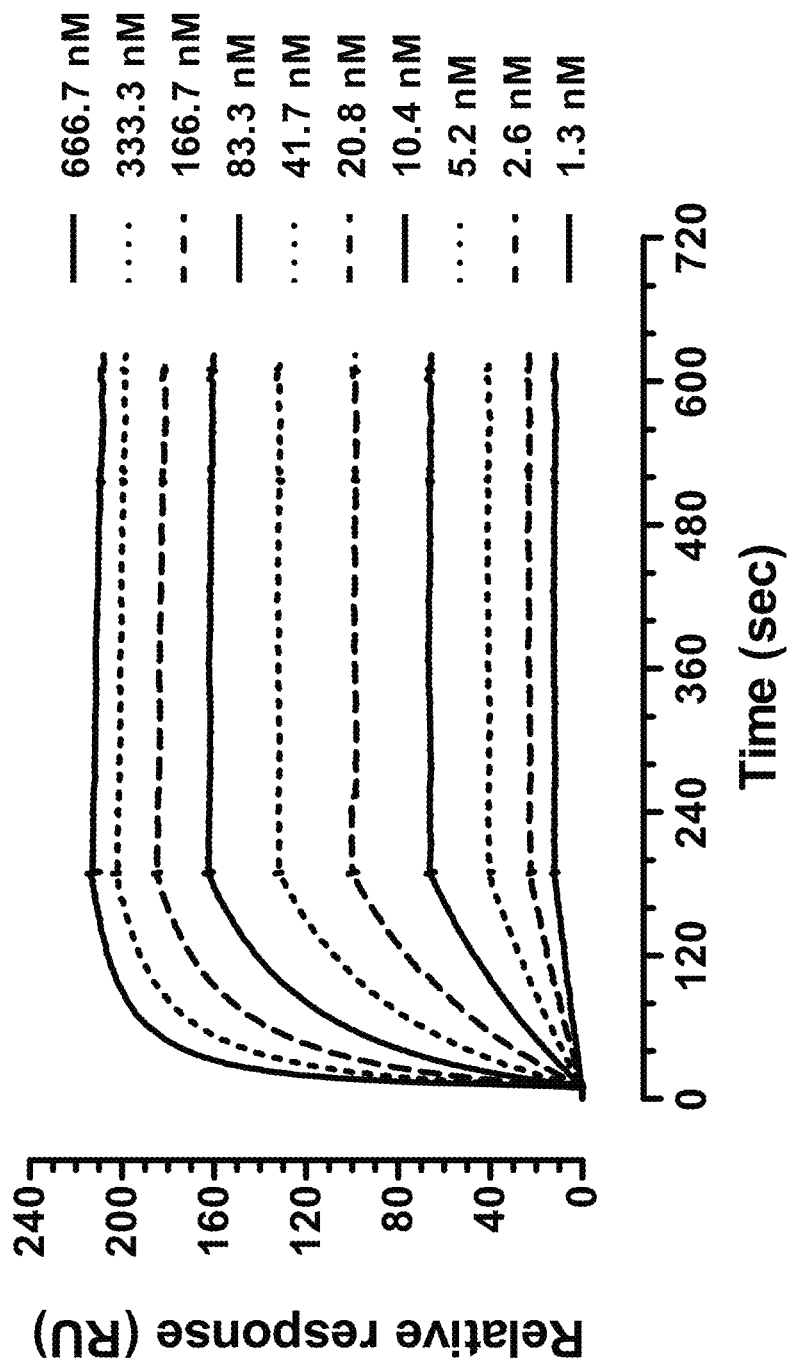

As shown in FIG. 10, the chimeric MAb ch1H12 demonstrated very high affinity ($K_D=1.10\times10^{-11}$ M) mainly due to a very slow dissociation rate ($k_{off}=2.99\times10^{-6}$ 1/s) which resulted in 64.4 hr half-life of the ch1H12/Axl complex. The found affinity value was superior in comparison with the parental murine antibody 1H12 (4.5-fold lower $K_D$), which may indicate better orientation of the $V_H$ and $V_L$ domains when mounted on a human constant domain scaffold.

Example 12

Mouse Monoclonal Antibody 1H12 Cross-Reacts with Axl from Non-Human Primates

The recombinant Axl-Fc chimeric proteins comprising extracellular portions of Axl receptor from cynomolgus and rhesus monkeys (cyno-Axl and rhe-Axl, respectively) were generated by transient expression in CHO cells. The recombinant cyno-Axl and rhe-Axl antigens were immobilized on the surface of CM5 sensor chip using amine coupling at the surface density of 1,345.0 and 1,515.9 RU, respectively. As a positive control, hu-Axl-Fc chimera produced under the same conditions was immobilized at the same chip at density of 1,234.9 RU.

The binding experiments were performed using Biacore 3000 instrument (GE Healthcare) at 25° C. The Biacore runs were performed in an automatic mode using Binding Analysis wizard.

The sample containing MAb 1H12 at concentration 10 µg/mL in HBS-EP buffer (GE Healthcare) was injected over the surfaces with immobilized antigens at flow rate of 30 µL/min for 3 min (association) followed by 5 min dissociation.

Figure 11:
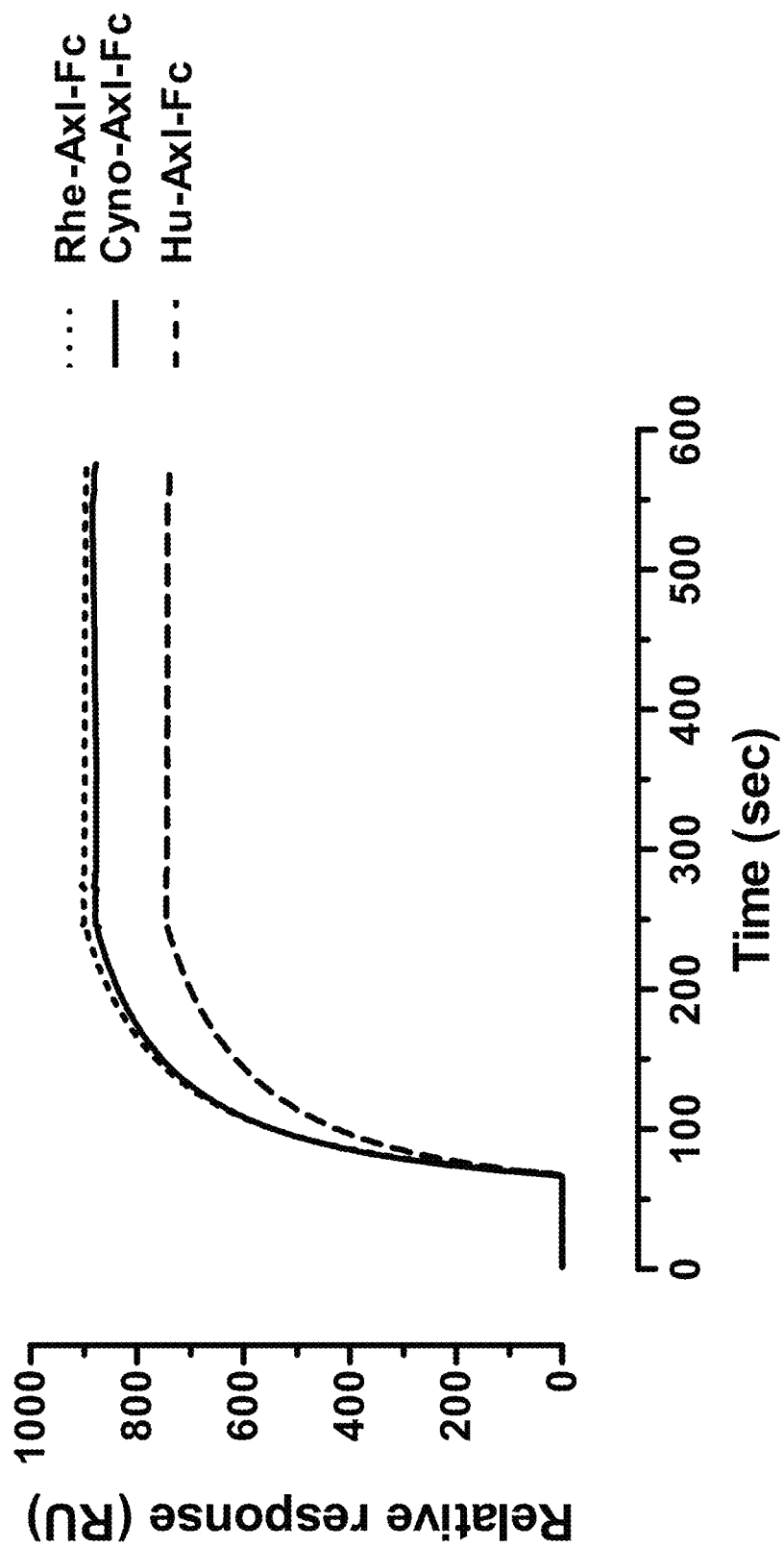

The results shown in FIG. 11 demonstrate strong and specific binding of MAb 1H12 to all Axl variants on human origin and from cynomolgus and rhesus monkeys.

Example 13

Killing of Tumor Cells using Chimeric Monoclonal Antibody ch1H12 Coupled to Saporin For generation of immunotoxin, the chimeric MAb ch1H12 was non-covalently coupled to a plant toxin Saporin using FabFc-ZAP human conjugate (4.5 nM final concentration) (Advanced Targeting Systems, Cat. no. IT-65). The effect of ch1H12-Saporin internalization on tumour cell viability was tested using Axl-positive tumour cell line MDA-MB-231 (human triple negative breast carcinoma). Eight hundred cells were seeded per well in 96-well plates in DMEM/F-12 media supplied with 10% FBS, L-glutamine (4 mM), streptomycin (5 µg/ml) and penicillin (5 U/ml) and allowed to attach for 16 hrs. The cells were incubated with different dilutions of immunotoxin ch1H12-Saporin for 72 hrs. The viability of the cells was determined by performing an XTT/PMS assay using a CLARIOstar® microplate reader (BMG LABTECH).

Figure 12:
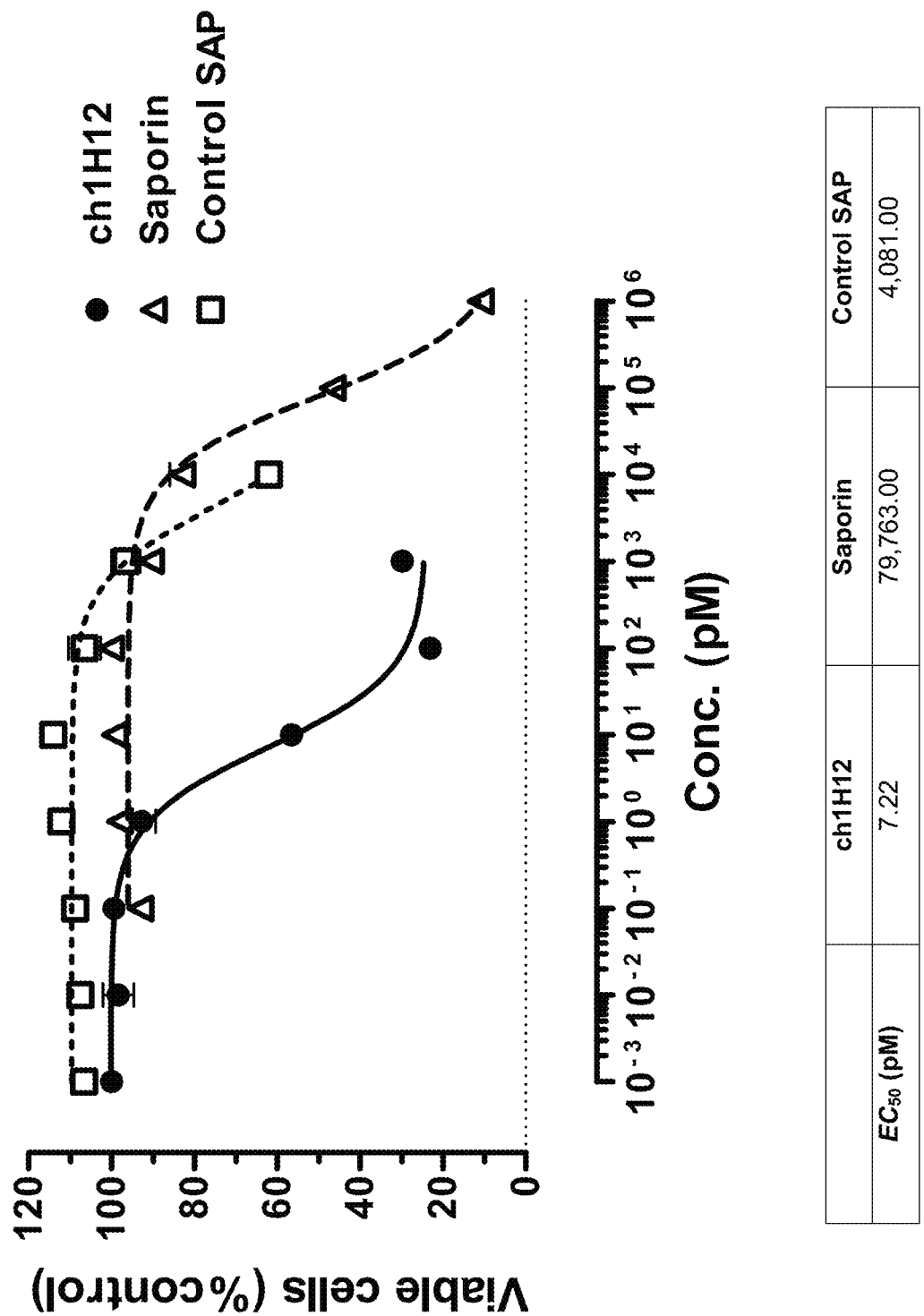

The results shown in FIG. 12 demonstrate good internalization and strong cell killing potency of ch1H12-based immunotoxin with $EC_{50}$ value (effective concentration leading to killing of 50% cells) in picomolar range.

Example 14

Antibody 1H12 Induces Axl Downstream Signaling

The experiments were performed using human cervical cancer derived cell line HeLa (ATCC® CCL-2™). The cells were grown in T175 flasks to 80% confluency in MEM culture medium (Sigma) supplemented with 10% FBS, penicillin-streptomycin and L-glutamine. The cells were washed with PBS and detached by treatment with 0.25% Trypsin/EDTA (Sigma) followed by centrifugation and resuspension in fresh medium (MEM/0.5% FBS). The cells were seeded in Petri dishes ($3\times10^6$ cells per dish) in MEM medium supplemented with 10% FBS. After 7 hrs incubation at 37° C., the cells were washed with PBS and kept in starvation medium (MEM/0.5% FBS) supplemented with 500 ng/ml of Axl-Fc (R&D Systems) to deplete endogenous Gas6. After 24 hrs incubation, the culture medium was aspirated and fresh MEM/0.5% FBS medium comprising either anti-Axl antibody 1H12 alone at concentration 7.5 µg/mL or 1H12 premixed with biotin-SP-conjugated AffiniPure goat anti-mouse IgG (H+L) #2.22 (ab crosslink mixture) was added. After 10-30 min incubation at 37° C., the cells were collected by centrifugation and resuspended in NP40-lysis buffer followed by 30 min incubation on ice. The cell lysates were cleared by centrifugation (12,000 rpm, 4° C., 5 min) and the protein concentrations were determined using BCA protein assay. The cell lysate samples comprising 35 µg of total protein were denatured in the presence of the reducing agent (Life Technologies) and loaded into the wells of NuPAGE 10% Bis-Tris polyacrylamide (PAA) gel, 1.0 mm×12 well (Invitrogen). The electrophoresis was performed using Bis-Tris SDS running buffer under the recommended conditions (Life Technologies) and the proteins were transfer on PVDF membrane, as described for 2 gels in a manual for XCell II™ Blot Module (Invitrogen) using the transfer buffer with 20% methanol. The membrane was incubated in 10 mL of blocking buffer, TBS/0.1% Tween20 (TBST) with 5% skimmed milk, for 1 hr at room temperature followed by overnight incubation in 5 mL of incubation buffer (TBST with 3% skimmed milk) containing 1:1000 dilution of anti-phospho-Akt (Ser$^{473}$) antibody (Cell Signaling) at 4° C. The membrane was washed three times for 5 min each with 10 mL of TBST followed by 1 hr incubation with goat anti-rabbit HRP-conjugated secondary antibody with gentle rolling at room temperature. Afterwards, the membrane was washed three times for 5 min in 10 mL of TBST and twice with 10 mL of TBS buffer. The membrane was incubated with 1 mL ECL substrate for 1 min at room temperature. Excess substrate solution was aspirated and the blot was visualised using a ChemiDoc™ XRS+ imager (Bio Rad) and Image lab software. As loading control, detection using anti-mouse actin antibody (1:10,000; Sigma) was used under the same conditions. The anti-phospho-Akt does not distinguish between AKT1, AKT2, and AKT3, hence the total level of 'phospho-Akt' is shown in the blot. Detection with anti-GAPDH antibody (Millipore) was used as loading control.

Figure 13:
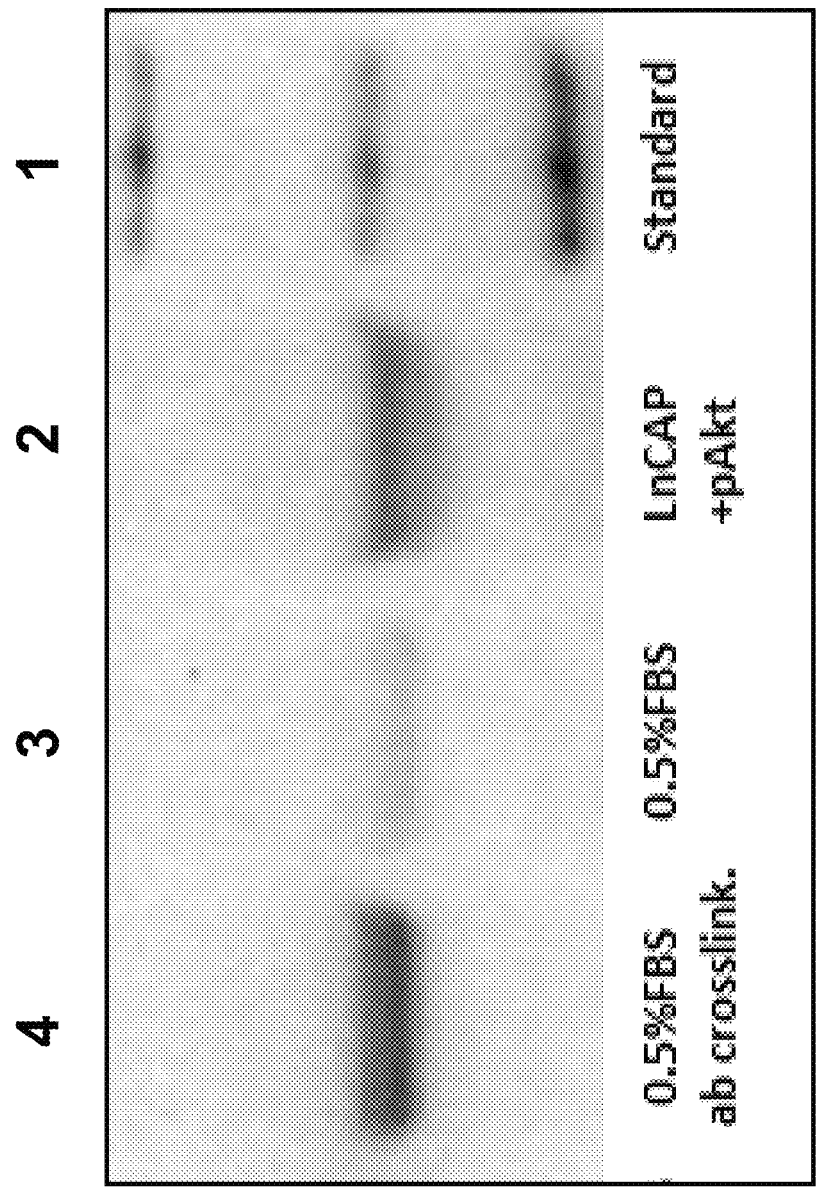
Figure 14:
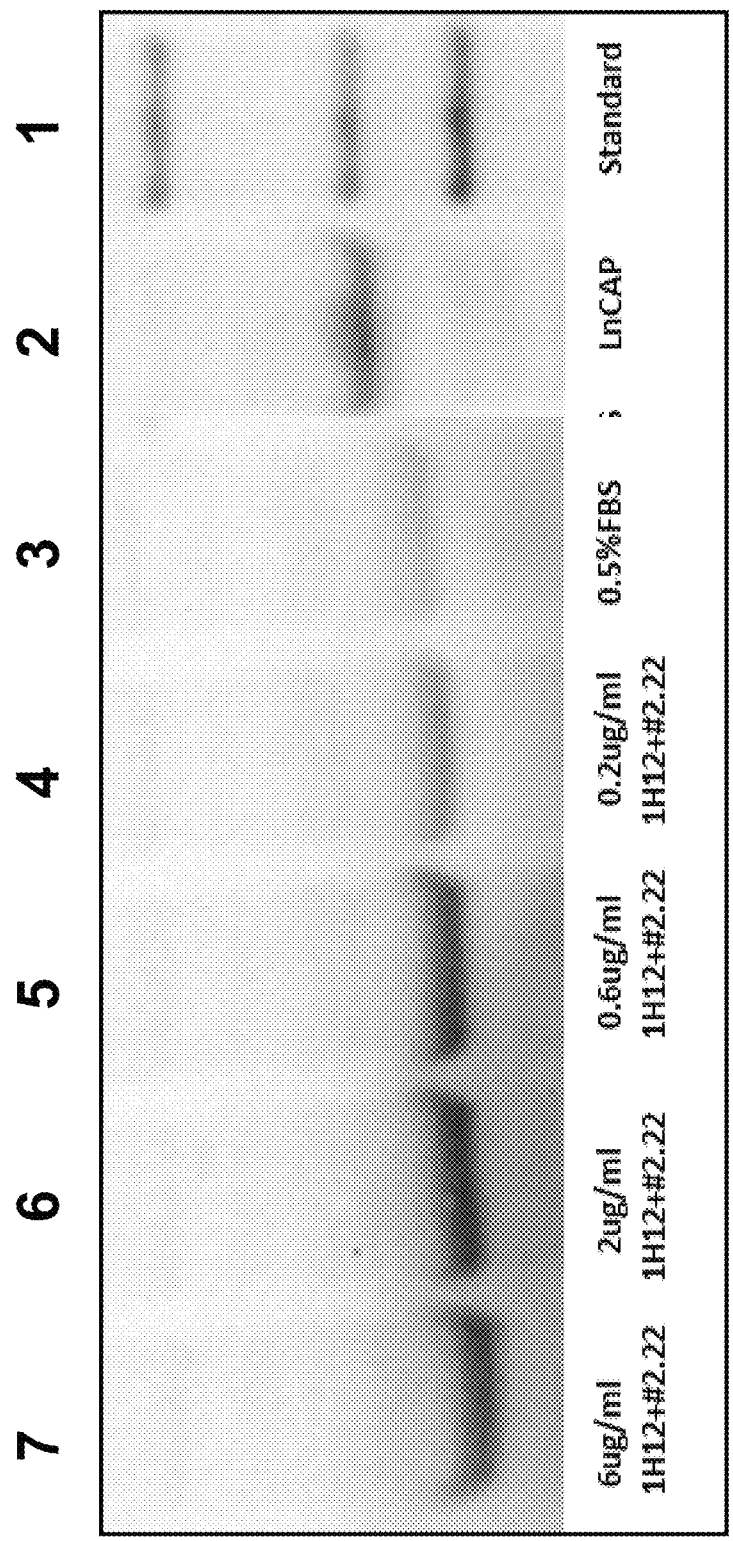
Figure 15:
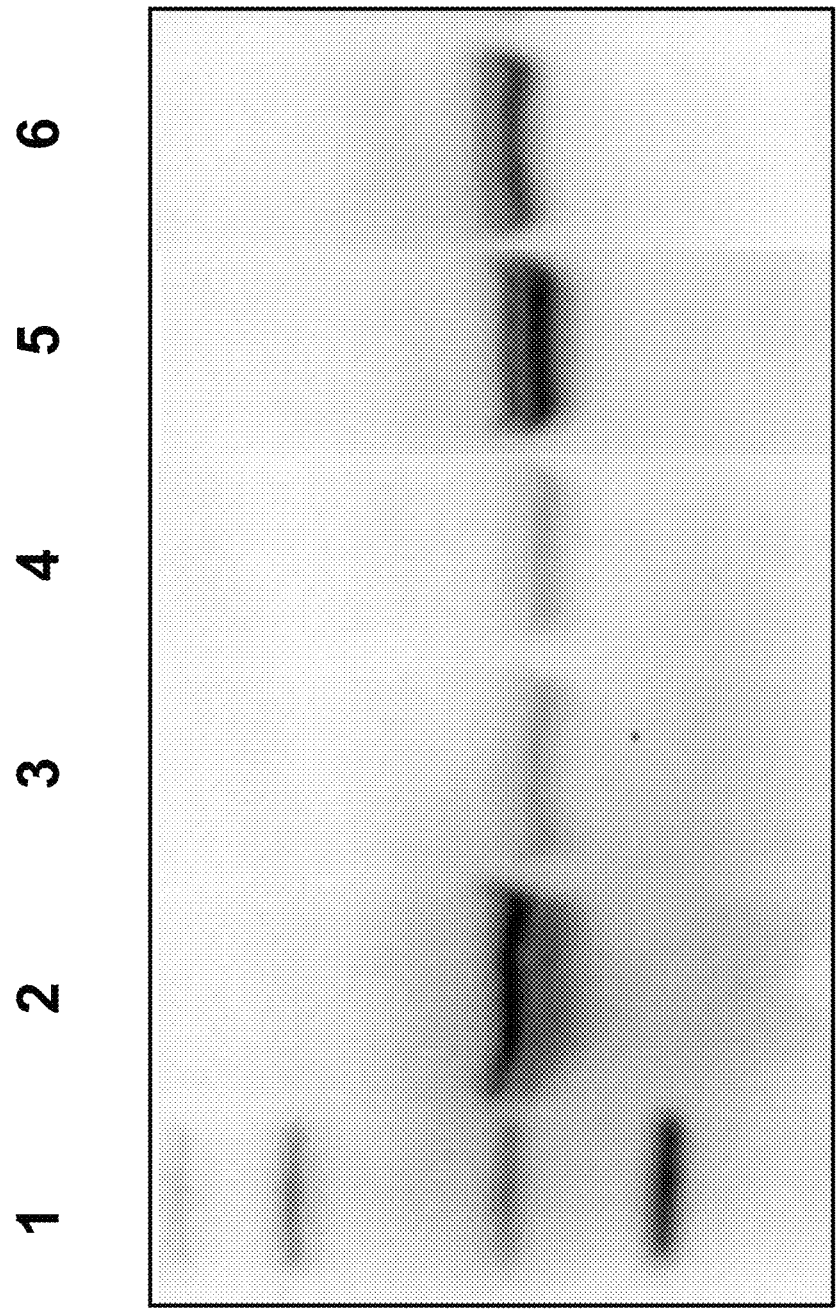

The results shown in FIG. 13 demonstrated that anti-Axl antibody 1H12 cross-linked with the secondary anti-mouse antibody induced strong Axl signalling in HeLa cells that used downstream phosphorylation of Akt on $Ser^{473}$ as the readout. The effect proved to be dose-dependent, higher amounts of cross-linked 1H12 caused stronger receptor signalling (FIG. 14). Furthermore, the data shown in FIG. 15 demonstrate that 1H12 antibody can cause Axl receptor activation and downstream signalling alone without cross-linking with secondary antibody. The results indicate that 1H12 antibody possesses strong agonistic activity.

Example 15

Mouse Monoclonal Antibody 1H12 Competes for Axl Binding with Commercial Antibody MAB154

The competitive binding study was performed using Biacore 3000 instrument (GE Healthcare) and Binding Analysis wizard with several cycles of two samples injection. As a first sample, a saturating concentration of MAb 1H12 (1.8 µM or 270 µg/mL) was injected over the surface of the CM5 sensor chip coated with rhAxl-Fc (using amine coupling) for 3 min at flow rate of 30 µL/min followed by 2.5 min stabilization (HBS-EP buffer alone) before the injection of the second sample. The following second samples were used: recombinant mouse (rm) Gas6 (R&D Systems, Cat. no. 986-GS/CF) and a commercial anti-Axl monoclonal antibody MAB154 (mouse IgG1, Clone # 108724; R&D Systems, Cat. No. MAB154); both at concentration 25 µg/mL. As a control, MAb 1H12 was used as a second sample under the same conditions (25 µg/mL). The second sample was injected for 3 min, followed by 2.5 min stabilization (buffer alone) and regeneration of the surface by 30 sec injection of a regeneration solution (10 mM HCl, 1 M NaCl) at flow rate 50 µL/min.

Figure 16:
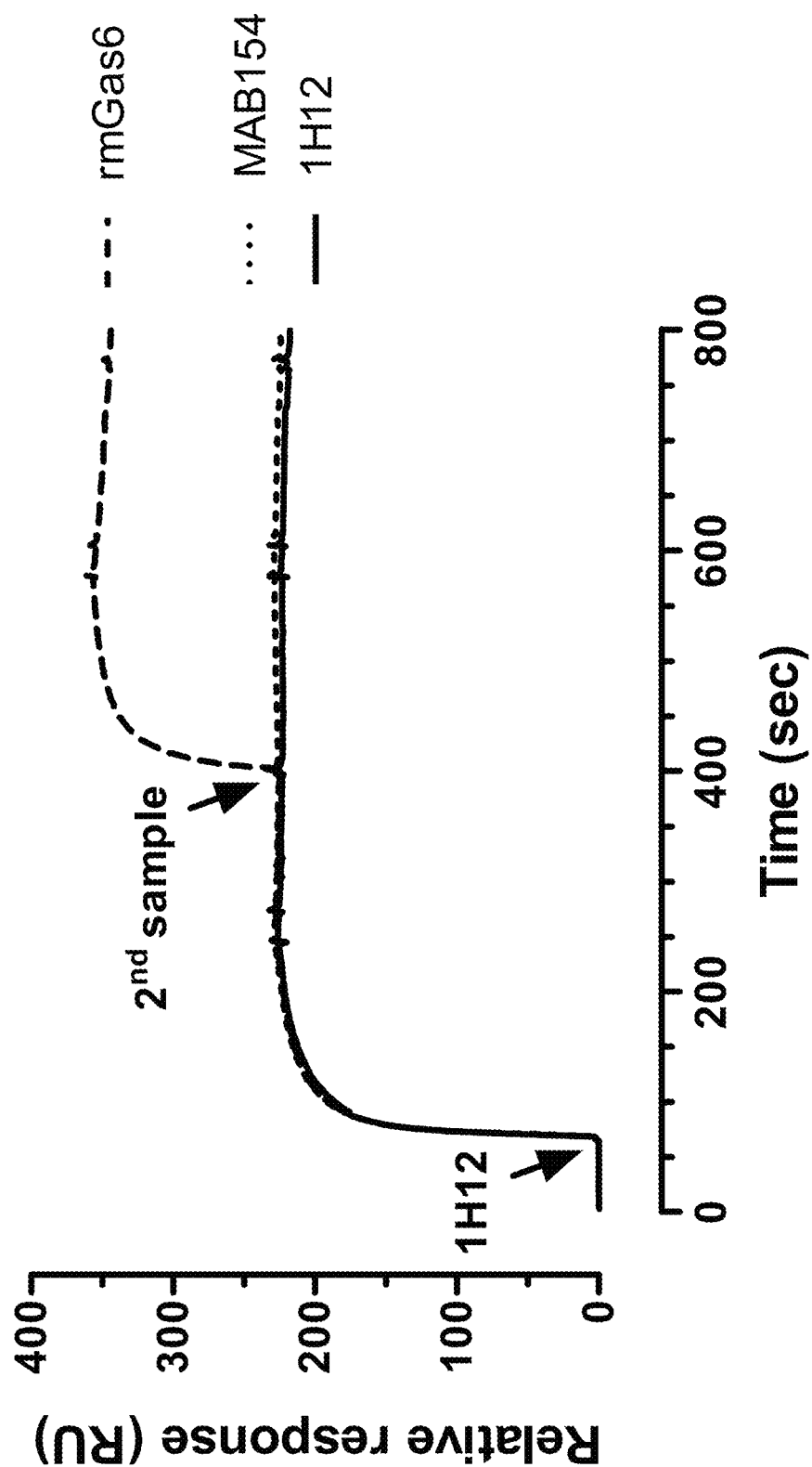
Figure 17:
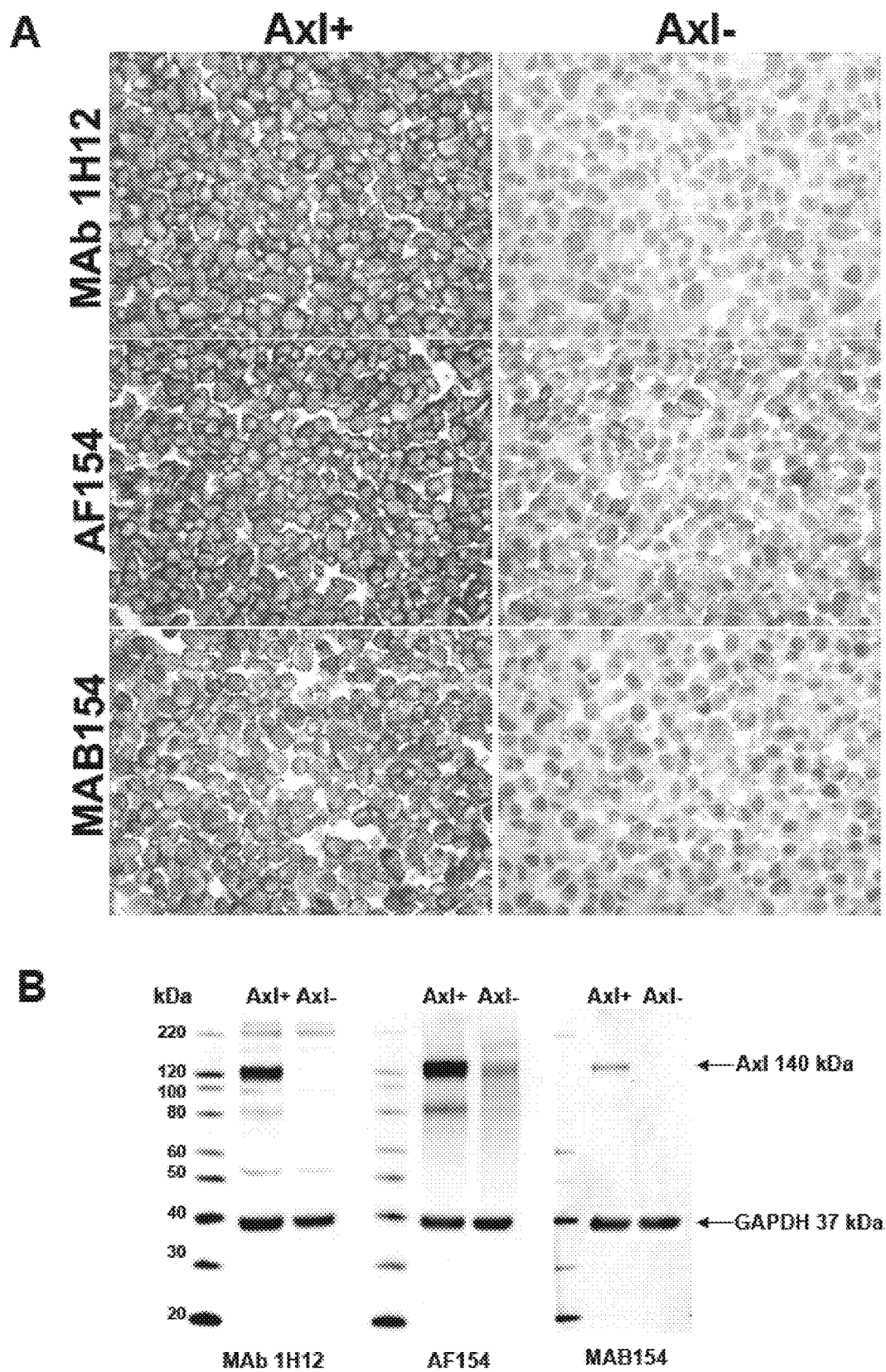

The results shown in FIG. 16 demonstrated that the MAb 1H12 inhibited binding of MAB154 to Axl and did not compete with mouse Gas6.

Example 16

Comparison of Axl Detection Using 1H12 and Commercial Antibodies

Immunohistochemistry and western blot analysis were performed for detection of Axl, using MAb 1H12.

On FFPE sections from cell pellets prepared using either Axl+ parental MDA-MB-231 cells or Axl− MDA-MB-231shAxl2 cells were stained using the MAb 1H12, polyclonal AF154 and monoclonal MAB154 (FIG. 17A). The MDA-MB-231 shAxl2 cell line has Axl expression knocked down using a retroviral construct expressing an Axl-targeting shRNA; this gives a mixed population, where ~10% of cells remain Axl+.

The best staining of Axl+ cells with MAb 1H12 was achieved with a concentration of 1 µg/ml (high-score positive staining of cell membranes and weak or no cytoplasmic staining), while the Axl− cells showed predominantly negative staining with some expression in scattered single cells. The presence of isolated Axl-expressing cells was consistent with the observed purity of the MDA-MB-231shAxl2, since-flow cytometry indicated that approximately 90% of the cells carried the retroviral shRNA construct. Comparative staining using AF154 at dilution 1:6400 (0.03125 µg/ml03125 µg/mL) and demonstrated somewhat strong membrane staining. However, strong staining was also observed in the Axl− cells in the scattered population with some weaker expression in most cells.

Staining with MAB154 demonstrated weaker performance than MAb 1H12 on Axl+ cells at similar concentration. However, fewer cells in the Axl− population were weakly stained compared to both MAb 1H12 and AF154. This indicates that 1H12 gives improved results as compared to AF154 and MAB154 on IHC.

Similar comparisons were done by Western blot analysis of Axl+ and Axl− cell lysates using the MAb 1H12, AF154 and MAB154 (FIG. 17B). All three antibodies were used at concentration of 1 µg/ml for the purpose of recommendation and visibility. All demonstrated a protein band of Axl at 140 kDa in the Axl+ cell lysate. However, this band was nearly undetectable in Axl− lysates with AF154, although some weak background staining was detected, which indicates its reaction against other protein at low level as noted in previous study Ahmed et al., 2015 . The blot with MAb 1H12 was consistently stronger than that seen with MAB154. From these results we concluded that MAb 1H12 performs significantly better than AF154 and MAB154 in western blot.

---

SEQUENCES

SEQ ID NO. 1 [VH domain (nt)]
GAGGTGAAGCTGGTGGAATCTGGGGGAGACTTAGTGAAGCCTGGAGGGTCCCTGAAA
CTCTCCTGTGCAGCCTCTGGATTCACTTTCAGTAGCTATGGCATGTCTTGGGTTCGCCA
GACTCCAGACAAGAGGCTGGAGTGGGTCGCAACCATTAGTAGTGGTGGTAGTTACACC
TACTATCCAGACAGTGTGAAGGGGCGATTCACCATCTCCAGAGACAATGCCAAGAACA
CCCTGTACCTGCAAATGAGCAGTCTGAAGTCTGAGGACACAGCCATGTATTACTGTGCA
AGACATCCCATCTACTATACTTACGACGATACTATGGACTACTGGGGTCAAGGAACCTC
AGTCACCGTCTCCTCAGCCAAAACGACACCC SEQ ID NO. 2 [VL domain (nt)]
GACATTGTGCTGACCCAATCTCCAGCAATCATGGCTGCATCTCCAGGGGAGAAGGTCA
CCATGACCTGCAGTGCCAGCTCAAGTGTAAGTTCTGGTAACTTTCACTGGTACCAGCAG
AAGCCAGGCACTTCTCCCAAACTCTGGATTTATAGGACATCCAACCTGGCTTCTGGAGT
CCCCGCTCGCTTCAGTGGCAGTGGGTCTGGGACCTCTTACTCTCTTACAATCAGCAGC
ATGGAGGCCGAAGATGCTGCCACTTATTACTGCCAGCAGTGGAGTGGTTACCCGTGGA
CGTTCGGTGGAGGCACCAAGCTGGAAATCAAACGGGCTGATGCTGCACCAACTGTATC
C

| SEQUENCES |
| --- |

SEQ ID NO. 3 [VH domain (aa)]
EVKLVESGGDLVKPGGSLKLSCAASGFTFSSYGMSWVRQTPDKRLEWVATISSGGSYTYY
PDSVKGRFTISRDNAKNTLYLQMSSLKSEDTAMYYCARHPIYYTYDDTMDYWGQGTSVTV
SS SEQ ID NO. 4 [VL domain (aa)]
DIVLTQSPAIMAASPGEKVTMTCSASSSVSSGNFHWYQQKPGTSPKLWIYRTSNLASGVPA
RFSGSGSGTSYSLTISSMEAEDAATYYCQQWSGYPWTFGGGTKLEIK SEQ ID NO. 5 [Heavy CDR1]
GFTFSSYGMS SEQ ID NO. 6 [Heavy CDR2]
TISSGGSYTYYPDSVKGRFTISRDNA SEQ ID NO. 7 [Heavy CDR3]
HPIYYTYDDTMDY SEQ ID NO. 8 [Light CDR1]
SASSSVSSGNFH SEQ ID NO. 9 [Light CDR2]
RTSNLAS SEQ ID NO. 10 [Light CDR3]
QQWSGYPWT SEQ ID NO. 11 [Heavy FR1]
EVKLVESGGDLVKPGGSLKLSCAAS SEQ ID NO. 12 [Heavy FR2]
WVRQTPDKRLEWVA SEQ ID NO. 13 [Heavy FR3]
KNTLYLQMSSLKSEDTAMYYCAR SEQ ID NO. 14 [Heavy FR4]
WGQGTSVTVSS SEQ ID NO. 15 [Light FR1]
DIVLTQSPAIMAASPGEKVTMTC SEQ ID NO. 16 [Light FR2]
VVYQQKPGTSPKLWIY SEQ ID NO. 17 [Light FR3]
GVPARFSGSGSGTSYSLTISSMEAEDAATYYC SEQ ID NO. 18 [Light FR4]
FGGGTKLEIK SEQ ID NO. 19 [Human Axl]
MAWRCPRMGRVPLAWCLALCGWACMAPRGTQAEESPFVGNPGNITGARGLTGTLRCQL
QVQGEPPEVHWLRDGQILELADSTQTQVPLGEDEQDDWIVVSQLRITSLQLSDTGQYQCL
VFLGHQTFVSQPGYVGLEGLPYFLEEPEDRTVAANTPFNLSCQAQGPPEPVDLLWLQDAV
PLATAPGHGPQRSLHVPGLNKTSSFSCEAHNAKGVTTSRTATITVLPQQPRNLHLVSRQPT
ELEVAWTPGLSGIYPLTHCTLQAVLSDDGMGIQAGEPDPPEEPLTSQASVPPHQLRLGSLH
PHTPYHIRVACTSSQGPSSWTHWLPVETPEGVPLGPPENISATRNGSQAFVHWQEPRAPL
QGTLLGYRLAYQGQDTPEVLMDIGLRQEVTLELQGDGSVSNLTVCVAAYTAAGDGPWSLP
VPLEAWRPGQAQPVHQLVKEPSTPAFSWPWWYVLLGAVVAAACVLILALFLVHRRKKETR
YGEVFEPTVERGELVVRYRVRKSYSRRTTEATLNSLGISEELKEKLRDVMVDRHKVALGKT
LGEGEFGAVMEGQLNQDDSILKVAVKTMKIAICTRSELEDFLSEAVCMKEFDHPNVMRLIGV
CFQGSERESFPAPVVILPFMKHGDLHSFLLYSRLGDQPVYLPTQMLVKFMADIASGMEYLS
TKRFIHRDLAARNCMLNENMSVCVADFGLSKKIYNGDYYRQGRIAKMPVKWIAIESLADRVY
TSKSDVWSFGVTMWEIATRGQTPYPGVENSEIYDYLRRGNRLKQPADCLDGLYALMSRC
WELNPQDRPSFTELREDLENTLKALPPAQEPDEILYVNMDEGGGYPEPPGAAGGADPPTQ
PDPKDSCSCLTAAEVHPAGRYVLCPSTTPSPAQPADRGSPAAPGQEDGA SEQ ID NO. 20 [Murine Axl]
MGRVPLAWWLALCCWGCAAHKDTQTEAGSPFVGNPGNITGARGLTGTLRCELQVQGEPP
EVVWLRDGQILELADNTQTQVPLGEDWQDEWKVVSQLRISALQLSDAGEYQCMVHLEGRT
FVSQPGFVGLEGLPYFLEEPEDKAVPANTPFNLSCQAQGPPEPVTLLWLQDAVPLAPVTGH
SSQHSLQTPGLNKTSSFSCEAHNAKGVTTSRTATITVLPQRPHHLHVVSRQPTELEVAWTP
GLSGIYPLTHCNLQAVLSDDGVGIWLGKSDPPEDPLTLQVSPPHQLRLEKLLPHTPYHIRIS
CSSSQGPSPWTHWLPVETTEGVPLGPPENVSAMRNGSQVLVRWQEPRVPLQGTLLGYRL
AYRGQDTPEVLMDIGLTREVTLELRGDRPVANLTVSVTAYTSAGDGPWSLPVPLEPWRPG
QGQPLHHLVSEPPPRAFSWPWWYVLLGALVAAACVLILALFLVHRRKKETRYGEVFEPTVE

SEQUENCES

RGELVVRYRVRKSYSRRTTEATLNSLGISEELKEKLRDVMVDRHKVALGKTLGEGEFGAVM
EGQLNQDDSILKVAVKTMKIAICTRSELEDFLSEAVCMKEFDHPNVMRLIGVCFQGSDREGF
PEPVVILPFMKHGDLHSFLLYSRLGDQPVFLPTQMLVKFMADIASGMEYLSTKRFIHRDLAA
RNCMLNENMSVCVADFGLSKKIYNGDYYRQGRIAKMPVKWIAIESLADRVYTSKSDVWSFG
VTMWEIATRGQTPYPGVENSEIYDYLRQGNRLKQPVDCLDGLYALMSRCWELNPRDRPSF
AELREDLENTLKALPPAQEPDEILYVNMDEGGSHLEPRGAAGGADPPTQPDPKDSCSCLTA
ADVHSAGRYVLCPSTAPGPTLSADRGCPAPPGQEDGA

SEQ ID NO. 21 [Human Tyro3]
MALRRSMGRPGLPPLPLPPPPRLGLLLAALASLLLPESAAAGLKLMGAPVKLTVSQGQPVK
LNCSVEGMEEPDIQWVKDGAVVQNLDQLYIPVSEQHWIGFLSLKSVERSDAGRYWCQVED
GGETEISQPVWLTVEGVPFFTVEPKDLAVPPNAPFQLSCEAVGPPEPVTIVWWVRGTTKIGG
PAPSPSVLNVTGVTQSTMFSCEAHNLKGLASSRTATVHLQALPAAPFNITVTKLSSSNASVA
WMPGADGRALLQSCTVQVTQAPGGWEVLAVVVPVPPFTCLLRDLVPATNYSLRVRCANAL
GPSPYADWVPFQTKGLAPASAPQNLHAIRTDSGLILEWEEVIPEAPLEGPLGPYKLSWVQD
NGTQDELTVEGTRANLTGWDPQKDLIVRVCVSNAVGCGPWSQPLVVSSHDRAGQQGPPH
SRTSWVPVVLGVLTALVTAAALALILLRKRRKETRFGQAFDSVMARGEPAVHFRAARSFNR
ERPERIEATLDSLGISDELKEKLEDVLIPEQQFTLGRMLGKGEFGSVREAQLKQEDGSFVKV
AVKMLKADIIASSDIEEFLREAACMKEFDHPHVAKLVGVSLRSRAKGRLPIPMVILPFMKHGD
LHAFLLASRIGENPFNLPLQTLIRFMVDIACGMEYLSSRNFIHRDLAARNCMLAEDMTVCVA
DFGLSRKIYSGDYYRQGCASKLPVKWLALESLADNLYTVQSDVWAFGVTMWEIMTRGQTP
YAGIENAEIYNYLIGGNRLKQPPECMEDVYDLMYQCWSADPKQRPSFTCLRMELENILGQL
SVLSASQDPLYINIERAEEPTAGGSLELPGRDQPYSGAGDGSGMGAVGGTPSDCRYILTPG
GLAEQPGQAEHQPESPLNETQRLLLLQQGLLPHSSC SEQ ID NO. 22 [Human Mer]
MKINNEEIVSDPIYIEVQGLPHFTKQPESMNVTRNTAFNLTCQAVGPPEPVNIFWVQNSSRV
NEQPEKSPSVLTVPGLTEMAVFSCEAHNDKGLTVSKGVQINIKAIPSPPTEVSIRNSTAHSILI
SWVPGFDGYSPFRNCSIQVKEADPLSNGSVMIFNTSALPHLYQIKQLQALANYSIGVSCMN
EIGWSAVSPWILASTTEGAPSVAPLNVTVFLNESSDNVDIRWMKPPTKQQDGELVGYRISH
VWQSAGISKELLEEVGQNGSRARISVQVHNATCTVRIAAVTKGGVGPFSDPVKIFIPAHGW
VDYAPSSTPAPGNADPVLIIFGCFCGFILIGLVLYISLAIRKRVQETKFGNAFTEEDSELVVNYI
AKKSFCRRAIELTLHSLGVSEELQNKLEDVVIDRNLLILGKILGEGEFGSVMEGNLKQEDGTS
LKVAVKTMKLDNSSQREIEEFLSEAACMKDFSHPNVIRLLGVCIEMSSQGIPKPMVILPFMKY
GDLHTYLLYSRLETGPKHIPLQTLLLKFMVDIALGMEYLSNRNFLHRDLAARNCMLRDDMTVC
VADFGLSKKIYSGDYYRQGRIAKMPVKWIAIESLADRVYTSKSDVWAFGVTMWEIATRGMT
PYPGVQNHEMYDYLLHGHRLKQPEDCLDELYEIMYSCWRTDPLDRPTFSVLRLQLEKLLES
LPDVRNQADVIYVNTQLLESSEGLAQGSTLAPLDLNIDPDSIIASCTPRAAISVVTAEVHDSKP
HEGRYILNGGSEEWEDLTSAPSAAVTAEKNSVLPGERLVRNGVSWSHSSMLPLGSSLPDE
LLFADDSSEGSEVLM

The invention claimed is:

1. An antibody that binds Axl and which comprises:
   a heavy chain variable region (VH) domain comprising a VH complementarity determining region (VH CDR) 1, a VH CDR2, and a VH CDR3 of SEQ ID NO: 3 as determined by Kabat; and
   a light chain variable region (VL) domain comprising a VL complementarity determining region (VL CDR) 1, a VL CDR2, and a VL CDR3 of SEQ ID NO: 4 as determined by Kabat.

2. The antibody according to claim 1, wherein the antibody competes for binding to Axl with an Axl binding domain of an antibody comprising the 1H12 VH domain (SEQ ID NO: 3) and the 1H12 VL domain (SEQ ID NO: 4).

3. The antibody according to claim 1 comprising the 1H12 VH domain (SEQ ID NO: 3).

4. The antibody according to claim 1 comprising the 1H12 VL domain (SEQ ID NO: 4).

5. The antibody according to claim 1 that binds Axl with affinity equal to or better than the affinity of an Axl antigen-binding site formed by the 1H12 VH domain (SEQ ID NO:

3) and the 1H12 VL domain (SEQ ID NO: 4), wherein the affinity of the antibody and the affinity of the antigen-binding site are determined under the same conditions.

6. The antibody according to claim 1, wherein the antibody is a whole antibody or an antigen-binding fragment selected from a Fv, scFv, dsFv, Fd, Fab, F(ab')$_2$, minibody, diabody, single-chain diabody, tandem scFv, bi-body, tri-body, and kappa(lambda)-body.

7. The antibody according to claim 1 wherein the antibody is a humanised antibody.

8. The antibody according to claim 1 wherein the antibody binds:
  (i) the same epitope as the 1H12 antibody, or
  (ii) an epitope which overlaps with the epitope bound by the 1H12 antibody.

9. The antibody according to claim 1 wherein the antibody is internalised following binding to Axl present on a cell surface.

10. The antibody according to claim 1 wherein the antibody is conjugated to a detectable label, enzyme, or toxin via a peptidyl bond or linker.

11. An isolated nucleic acid which comprises a nucleotide sequence encoding the antibody, antibody VH domain, or antibody VH and VL domains of the antibody according to claim 1.

12. A host cell transformed with the nucleic acid according to claim 11.

13. A method of obtaining an antibody that binds Axl, comprising:
  providing by way of addition, deletion, substitution or insertion of one or more amino acids in the amino acid sequence of the 1H12 heavy chain variable region (VH) domain (SEQ ID NO: 3) one or more VH domains each of which is an amino acid sequence variant of the 1H12 VH domain, and combining one or more VH domain amino acid sequence variants thus provided with one or more light chain variable region (VL) domains to provide one or more VH/VL combinations; and/or
  providing by way of addition, deletion, substitution or insertion of one or more amino acids in the amino acid sequence of the 1H12 VL domain (SEQ ID NO: 4) a VL domain which is an amino acid sequence variant of the 1H12 VL domain, and combining one or more VL domain amino acid sequence variants thus provided with one or more VH domains to provide one or more VH/VL domain combinations;
  and
  testing the VH domain amino acid sequence variants or VH/VL combination or combinations to identify an antibody that binds Axl.

14. A method of obtaining an antibody that binds Axl, comprising:
  (a) providing starting nucleic acids encoding one or more heavy chain variable region (VH) domains which either comprise a complementarity determining region 3 (CDR3) to be replaced or lack a CDR3 encoding region, and combining said starting nucleic acid with a donor nucleic acid encoding the VH CDR3 amino acid sequence of SEQ ID NO:7 such that said donor nucleic acid is inserted into the CDR3 region in the starting nucleic acid, so as to provide product nucleic acids encoding VH domains; or
  providing starting nucleic acids encoding one or more light chain variable region (VL) domains which either comprise a CDR3 to be replaced or lack a CDR3 encoding region, and combining said starting nucleic acid with a donor nucleic acid encoding the VL CDR3 amino acid sequence of SEQ ID NO: 10 such that said donor nucleic acid is inserted into the CDR3 region in the starting nucleic acid, so as to provide product nucleic acids encoding VL domains;
  (b) expressing the nucleic acids of said product nucleic acids encoding VH domains and combining the VH domains thus produced with one or more VL domains to provide VH/VL combinations, and/or expressing the nucleic acids of said product nucleic acids encoding VL domains and combining the VL domains thus produced with one or more VH domains to provide VH/VL combinations;
  (c) selecting an antibody comprising a VH domain or a VH/VL combination that binds Axl; and
  (d) recovering said antibody that binds Axl and/or nucleic acid encoding the antibody that binds Axl.

15. A composition comprising an antibody according to claim 1, or an immunoconjugate thereof, and a pharmaceutically acceptable excipient.

16. The composition according to claim 15 further comprising an immune checkpoint modulator (ICM).

* * * * *

UNITED STATES PATENT AND TRADEMARK OFFICE
CERTIFICATE OF CORRECTION

PATENT NO. : 11,186,643 B2
APPLICATION NO. : 15/958076
DATED : November 30, 2021
INVENTOR(S) : David Robert Micklem et al.

Page 1 of 1

It is certified that error appears in the above-identified patent and that said Letters Patent is hereby corrected as shown below:

In the Claims

In Claim 11, Column 85, Line 22, "nucleicacid" should read --nucleic acid--

In Claim 11, Column 85, Line 23, "encodingthe" should read --encoding the--

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 22

<210> SEQ ID NO 1
<211> LENGTH: 381
<212> TYPE: DNA
<213> ORGANISM: Mus musculus

<400> SEQUENCE: 1

```
gaggtgaagc tggtggaatc tgggggagac ttagtgaagc ctggagggtc cctgaaactc      60
tcctgtgcag cctctggatt cactttcagt agctatggca tgtcttgggt tcgccagact     120
ccagacaaga ggctggagtg ggtcgcaacc attagtagtg gtggtagtta cacctactat     180
ccagacagtg tgaaggggcg attcaccatc tccagagaca tgccaagaa caccctgtac      240
ctgcaaatga gcagtctgaa gtctgaggac acagccatgt attactgtgc aagacatccc     300
atctactata cttacgacga tactatggac tactggggtc aaggaacctc agtcaccgtc     360
tcctcagcca aaacgacacc c                                               381
```

<210> SEQ ID NO 2
<211> LENGTH: 351
<212> TYPE: DNA
<213> ORGANISM: Mus musculus

<400> SEQUENCE: 2

```
gacattgtgc tgacccaatc tccagcaatc atggctgcat ctccagggga gaaggtcacc      60
atgacctgca gtgccagctc aagtgtaagt tctggtaact ttcactggta ccagcagaag     120
ccaggcactt ctcccaaact ctggatttat aggacatcca acctggcttc tggagtcccc     180
gctcgcttca gtggcagtgg gtctgggacc tcttactctc ttacaatcag cagcatggag     240
gccgaagatg ctgccactta ttactgccag cagtggagtg gttacccgtg acgttcggt      300 ggaggcacca agctggaaat caaacgggct gatgctgcac caactgtatc c              351
```

<210> SEQ ID NO 3
<211> LENGTH: 122
<212> TYPE: PRT
<213> ORGANISM: Mus musculus

<400> SEQUENCE: 3

```
Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Pro Ile Tyr Tyr Thr Tyr Asp Asp Thr Met Asp Tyr Trp
            100                 105                 110

Gly Gln Gly Thr Ser Val Thr Val Ser Ser
        115                 120
```

<210> SEQ ID NO 4
<211> LENGTH: 108
<212> TYPE: PRT
<213> ORGANISM: Mus musculus

<400> SEQUENCE: 4

```
Asp Ile Val Leu Thr Gln Ser Pro Ala Ile Met Ala Ala Ser Pro Gly
1               5                   10                  15

Glu Lys Val Thr Met Thr Cys Ser Ala Ser Ser Ser Val Ser Ser Gly
            20                  25                  30

Asn Phe His Trp Tyr Gln Gln Lys Pro Gly Thr Ser Pro Lys Leu Trp
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Gly Tyr Pro
                85                  90                  95

Trp Thr Phe Gly Gly Gly Thr Lys Leu Glu Ile Lys
            100                 105
```

<210> SEQ ID NO 5
<211> LENGTH: 10
<212> TYPE: PRT
<213> ORGANISM: Mus musculus

```
<400> SEQUENCE: 5

Gly Phe Thr Phe Ser Ser Tyr Gly Met Ser
1               5                   10

<210> SEQ ID NO 6
<211> LENGTH: 26
<212> TYPE: PRT
<213> ORGANISM: Mus musculus

<400> SEQUENCE: 6

Thr Ile Ser Ser Gly Gly Ser Tyr Thr Tyr Tyr Pro Asp Ser Val Lys
1               5                   10                  15

Gly Arg Phe Thr Ile Ser Arg Asp Asn Ala
            20                  25

<210> SEQ ID NO 7
<211> LENGTH: 13
<212> TYPE: PRT
<213> ORGANISM: Mus musculus

<400> SEQUENCE: 7

His Pro Ile Tyr Tyr Thr Tyr Asp Asp Thr Met Asp Tyr
1               5                   10

<210> SEQ ID NO 8
<211> LENGTH: 12
<212> TYPE: PRT
<213> ORGANISM: Mus musculus

<400> SEQUENCE: 8

Ser Ala Ser Ser Ser Val Ser Ser Gly Asn Phe His
1               5                   10

<210> SEQ ID NO 9
<211> LENGTH: 7
<212> TYPE: PRT
<213> ORGANISM: Mus musculus

<400> SEQUENCE: 9

Arg Thr Ser Asn Leu Ala Ser
1               5

<210> SEQ ID NO 10
<211> LENGTH: 9
<212> TYPE: PRT
<213> ORGANISM: Mus musculus

<400> SEQUENCE: 10

Gln Gln Trp Ser Gly Tyr Pro Trp Thr
1               5

<210> SEQ ID NO 11
<211> LENGTH: 25
<212> TYPE: PRT
<213> ORGANISM: Mus musculus

<400> SEQUENCE: 11

Glu Val Lys Leu Val Glu Ser Gly Gly Asp Leu Val Lys Pro Gly Gly
1               5                   10                  15

Ser Leu Lys Leu Ser Cys Ala Ala Ser
            20                  25
```

-continued

```
<210> SEQ ID NO 12
<211> LENGTH: 14
<212> TYPE: PRT
<213> ORGANISM: Mus musculus

<400> SEQUENCE: 12

Trp Val Arg Gln Thr Pro Asp Lys Arg Leu Glu Trp Val Ala
1               5                   10

<210> SEQ ID NO 13
<211> LENGTH: 23
<212> TYPE: PRT
<213> ORGANISM: Mus musculus

<400> SEQUENCE: 13

Lys Asn Thr Leu Tyr Leu Gln Met Ser Ser Leu Lys Ser Glu Asp Thr
1               5                   10                  15

Ala Met Tyr Tyr Cys Ala Arg
            20

<210> SEQ ID NO 14
<211> LENGTH: 11
<212> TYPE: PRT
<213> ORGANISM: Mus musculus

<400> SEQUENCE: 14

Trp Gly Gln Gly Thr Ser Val Thr Val Ser Ser
1               5                   10

<210> SEQ ID NO 15
<211> LENGTH: 23
<212> TYPE: PRT
<213> ORGANISM: Mus musculus

<400> SEQUENCE: 15

Asp Ile Val Leu Thr Gln Ser Pro Ala Ile Met Ala Ala Ser Pro Gly
1               5                   10                  15

Glu Lys Val Thr Met Thr Cys
            20

<210> SEQ ID NO 16
<211> LENGTH: 15
<212> TYPE: PRT
<213> ORGANISM: Mus musculus

<400> SEQUENCE: 16

Trp Tyr Gln Gln Lys Pro Gly Thr Ser Pro Lys Leu Trp Ile Tyr
1               5                   10                  15

<210> SEQ ID NO 17
<211> LENGTH: 32
<212> TYPE: PRT
<213> ORGANISM: Mus musculus

<400> SEQUENCE: 17

Gly Val Pro Ala Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 18
<211> LENGTH: 10
<212> TYPE: PRT
```

<400> SEQUENCE: 18

Phe Gly Gly Gly Thr Lys Leu Glu Ile Lys
1               5                   10

<210> SEQ ID NO 19
<211> LENGTH: 894
<212> TYPE: PRT
<213> ORGANISM: Homo sapiens

<400> SEQUENCE: 19

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

```
Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
                420                 425                 430

Pro Val His Gln Leu Val Lys Glu Pro Ser Thr Pro Ala Phe Ser Trp
            435                 440                 445

Pro Trp Trp Tyr Val Leu Leu Gly Ala Val Ala Ala Ala Cys Val
            450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
                500                 505                 510

Leu Asn Ser Leu Gly Ile Ser Glu Glu Leu Lys Glu Lys Leu Arg Asp
            515                 520                 525

Val Met Val Asp Arg His Lys Val Ala Leu Gly Lys Thr Leu Gly Glu
530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
        610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Arg Gly Asn Arg Leu
            755                 760                 765
```

```
Lys Gln Pro Ala Asp Cys Leu Asp Gly Leu Tyr Ala Leu Met Ser Arg
    770                 775                 780
Cys Trp Glu Leu Asn Pro Gln Asp Arg Pro Ser Phe Thr Glu Leu Arg
785                 790                 795                 800
Glu Asp Leu Glu Asn Thr Leu Lys Ala Leu Pro Pro Ala Gln Glu Pro
                805                 810                 815
Asp Glu Ile Leu Tyr Val Asn Met Asp Glu Gly Gly Tyr Pro Glu
                820                 825                 830
Pro Pro Gly Ala Ala Gly Gly Ala Asp Pro Pro Thr Gln Pro Asp Pro
                835                 840                 845
Lys Asp Ser Cys Ser Cys Leu Thr Ala Ala Glu Val His Pro Ala Gly
850                 855                 860
Arg Tyr Val Leu Cys Pro Ser Thr Thr Pro Ser Pro Ala Gln Pro Ala
865                 870                 875                 880
Asp Arg Gly Ser Pro Ala Ala Pro Gly Gln Glu Asp Gly Ala
                885                 890
```

<210> SEQ ID NO 20
<211> LENGTH: 888
<212> TYPE: PRT
<213> ORGANISM: Mus musculus

<400> SEQUENCE: 20

```
Met Gly Arg Val Pro Leu Ala Trp Trp Leu Ala Leu Cys Cys Trp Gly
1               5                   10                  15
Cys Ala Ala His Lys Asp Thr Gln Thr Glu Ala Gly Ser Pro Phe Val
                20                  25                  30
Gly Asn Pro Gly Asn Ile Thr Gly Ala Arg Gly Leu Thr Gly Thr Leu
                35                  40                  45
Arg Cys Glu Leu Gln Val Gln Gly Glu Pro Pro Glu Val Val Trp Leu
    50                  55                  60
Arg Asp Gly Gln Ile Leu Glu Leu Ala Asp Asn Thr Gln Thr Gln Val
65                  70                  75                  80
Pro Leu Gly Glu Asp Trp Gln Asp Glu Trp Lys Val Val Ser Gln Leu
                85                  90                  95
Arg Ile Ser Ala Leu Gln Leu Ser Asp Ala Gly Glu Tyr Gln Cys Met
                100                 105                 110
Val His Leu Glu Gly Arg Thr Phe Val Ser Gln Pro Gly Phe Val Gly
                115                 120                 125
Leu Glu Gly Leu Pro Tyr Phe Leu Glu Glu Pro Glu Asp Lys Ala Val
            130                 135                 140
Pro Ala Asn Thr Pro Phe Asn Leu Ser Cys Gln Ala Gln Gly Pro Pro
145                 150                 155                 160
Glu Pro Val Thr Leu Leu Trp Leu Gln Asp Ala Val Pro Leu Ala Pro
                165                 170                 175
Val Thr Gly His Ser Ser Gln His Ser Leu Gln Thr Pro Gly Leu Asn
                180                 185                 190
Lys Thr Ser Ser Phe Ser Cys Glu Ala His Asn Ala Lys Gly Val Thr
            195                 200                 205
Thr Ser Arg Thr Ala Thr Ile Thr Val Leu Pro Gln Arg Pro His His
            210                 215                 220
Leu His Val Val Ser Arg Gln Pro Thr Glu Leu Glu Val Ala Trp Thr
225                 230                 235                 240
Pro Gly Leu Ser Gly Ile Tyr Pro Leu Thr His Cys Asn Leu Gln Ala
                245                 250                 255
```

-continued

Val Leu Ser Asp Asp Gly Val Gly Ile Trp Leu Gly Lys Ser Asp Pro
        260             265             270

Pro Glu Asp Pro Leu Thr Leu Gln Val Ser Val Pro Pro His Gln Leu
            275             280             285

Arg Leu Glu Lys Leu Leu Pro His Thr Pro Tyr His Ile Arg Ile Ser
    290             295             300

Cys Ser Ser Ser Gln Gly Pro Ser Pro Trp Thr His Trp Leu Pro Val
305             310             315             320

Glu Thr Thr Glu Gly Val Pro Leu Gly Pro Glu Asn Val Ser Ala
                325             330             335

Met Arg Asn Gly Ser Gln Val Leu Val Arg Trp Gln Glu Pro Arg Val
            340             345             350

Pro Leu Gln Gly Thr Leu Leu Gly Tyr Arg Leu Ala Tyr Arg Gly Gln
        355             360             365

Asp Thr Pro Glu Val Leu Met Asp Ile Gly Leu Thr Arg Glu Val Thr
    370             375             380

Leu Glu Leu Arg Gly Asp Arg Pro Val Ala Asn Leu Thr Val Ser Val
385             390             395             400

Thr Ala Tyr Thr Ser Ala Gly Asp Gly Pro Trp Ser Leu Pro Val Pro
            405             410             415

Leu Glu Pro Trp Arg Pro Gly Gln Gly Gln Pro Leu His His Leu Val
        420             425             430

Ser Glu Pro Pro Arg Ala Phe Ser Trp Pro Trp Trp Tyr Val Leu
    435             440             445

Leu Gly Ala Leu Val Ala Ala Cys Val Leu Ile Leu Ala Leu Phe
    450             455             460

Leu Val His Arg Arg Lys Lys Glu Thr Arg Tyr Gly Glu Val Phe Glu
465             470             475             480

Pro Thr Val Glu Arg Gly Glu Leu Val Val Arg Tyr Arg Val Arg Lys
            485             490             495

Ser Tyr Ser Arg Arg Thr Thr Glu Ala Thr Leu Asn Ser Leu Gly Ile
        500             505             510

Ser Glu Glu Leu Lys Glu Lys Leu Arg Asp Val Met Val Asp Arg His
    515             520             525

Lys Val Ala Leu Gly Lys Thr Leu Gly Glu Gly Glu Phe Gly Ala Val
530             535             540

Met Glu Gly Gln Leu Asn Gln Asp Asp Ser Ile Leu Lys Val Ala Val
545             550             555             560

Lys Thr Met Lys Ile Ala Ile Cys Thr Arg Ser Glu Leu Glu Asp Phe
            565             570             575

Leu Ser Glu Ala Val Cys Met Lys Glu Phe Asp His Pro Asn Val Met
        580             585             590

Arg Leu Ile Gly Val Cys Phe Gln Gly Ser Asp Arg Glu Gly Phe Pro
    595             600             605

Glu Pro Val Val Ile Leu Pro Phe Met Lys His Gly Asp Leu His Ser
    610             615             620

Phe Leu Leu Tyr Ser Arg Leu Gly Asp Gln Pro Val Phe Leu Pro Thr
625             630             635             640

Gln Met Leu Val Lys Phe Met Ala Asp Ile Ala Ser Gly Met Glu Tyr
            645             650             655

Leu Ser Thr Lys Arg Phe Ile His Arg Asp Leu Ala Ala Arg Asn Cys
        660             665             670

```
Met Leu Asn Glu Asn Met Ser Val Cys Val Ala Asp Phe Gly Leu Ser
            675                 680                 685

Lys Lys Ile Tyr Asn Gly Asp Tyr Tyr Arg Gln Gly Arg Ile Ala Lys
690                 695                 700

Met Pro Val Lys Trp Ile Ala Ile Glu Ser Leu Ala Asp Arg Val Tyr
705                 710                 715                 720

Thr Ser Lys Ser Asp Val Trp Ser Phe Gly Val Thr Met Trp Glu Ile
                725                 730                 735

Ala Thr Arg Gly Gln Thr Pro Tyr Pro Gly Val Glu Asn Ser Glu Ile
            740                 745                 750

Tyr Asp Tyr Leu Arg Gln Gly Asn Arg Leu Lys Gln Pro Val Asp Cys
        755                 760                 765

Leu Asp Gly Leu Tyr Ala Leu Met Ser Arg Cys Trp Glu Leu Asn Pro
    770                 775                 780

Arg Asp Arg Pro Ser Phe Ala Glu Leu Arg Glu Asp Leu Glu Asn Thr
785                 790                 795                 800

Leu Lys Ala Leu Pro Pro Ala Gln Glu Pro Asp Glu Ile Leu Tyr Val
                805                 810                 815

Asn Met Asp Glu Gly Gly Ser His Leu Glu Pro Arg Gly Ala Ala Gly
            820                 825                 830

Gly Ala Asp Pro Pro Thr Gln Pro Asp Pro Lys Asp Ser Cys Ser Cys
        835                 840                 845

Leu Thr Ala Ala Asp Val His Ser Ala Gly Arg Tyr Val Leu Cys Pro
    850                 855                 860

Ser Thr Ala Pro Gly Pro Thr Leu Ser Ala Asp Arg Gly Cys Pro Ala
865                 870                 875                 880

Pro Pro Gly Gln Glu Asp Gly Ala
                885

<210> SEQ ID NO 21
<211> LENGTH: 890
<212> TYPE: PRT
<213> ORGANISM: Homo sapiens

<400> SEQUENCE: 21

Met Ala Leu Arg Arg Ser Met Gly Arg Pro Gly Leu Pro Pro Leu Pro
1               5                   10                  15

Leu Pro Pro Pro Arg Leu Gly Leu Leu Ala Ala Leu Ala Ser
            20                  25                  30

Leu Leu Leu Pro Glu Ser Ala Ala Ala Gly Leu Lys Leu Met Gly Ala
        35                  40                  45

Pro Val Lys Leu Thr Val Ser Gln Gly Gln Pro Val Lys Leu Asn Cys
    50                  55                  60

Ser Val Glu Gly Met Glu Pro Asp Ile Gln Trp Val Lys Asp Gly
65                  70                  75                  80

Ala Val Val Gln Asn Leu Asp Gln Leu Tyr Ile Pro Val Ser Glu Gln
                85                  90                  95

His Trp Ile Gly Phe Leu Ser Leu Lys Ser Val Glu Arg Ser Asp Ala
            100                 105                 110

Gly Arg Tyr Trp Cys Gln Val Glu Asp Gly Gly Glu Thr Glu Ile Ser
        115                 120                 125

Gln Pro Val Trp Leu Thr Val Glu Gly Val Pro Phe Phe Thr Val Glu
    130                 135                 140

Pro Lys Asp Leu Ala Val Pro Pro Asn Ala Pro Phe Gln Leu Ser Cys
145                 150                 155                 160
```

```
Glu Ala Val Gly Pro Pro Glu Pro Val Thr Ile Val Trp Trp Arg Gly
                165                 170                 175

Thr Thr Lys Ile Gly Gly Pro Ala Pro Ser Pro Ser Val Leu Asn Val
            180                 185                 190

Thr Gly Val Thr Gln Ser Thr Met Phe Ser Cys Glu Ala His Asn Leu
            195                 200                 205

Lys Gly Leu Ala Ser Ser Arg Thr Ala Thr Val His Leu Gln Ala Leu
            210                 215                 220

Pro Ala Ala Pro Phe Asn Ile Thr Val Thr Lys Leu Ser Ser Ser Asn
225                 230                 235                 240

Ala Ser Val Ala Trp Met Pro Gly Ala Asp Gly Arg Ala Leu Leu Gln
                245                 250                 255

Ser Cys Thr Val Gln Val Thr Gln Ala Pro Gly Gly Trp Glu Val Leu
                260                 265                 270

Ala Val Val Pro Val Pro Phe Thr Cys Leu Leu Arg Asp Leu
                275                 280                 285

Val Pro Ala Thr Asn Tyr Ser Leu Arg Val Arg Cys Ala Asn Ala Leu
            290                 295                 300

Gly Pro Ser Pro Tyr Ala Asp Trp Val Pro Phe Gln Thr Lys Gly Leu
305                 310                 315                 320

Ala Pro Ala Ser Ala Pro Gln Asn Leu His Ala Ile Arg Thr Asp Ser
                325                 330                 335

Gly Leu Ile Leu Glu Trp Glu Val Ile Pro Glu Ala Pro Leu Glu
                340                 345                 350

Gly Pro Leu Gly Pro Tyr Lys Leu Ser Trp Val Gln Asp Asn Gly Thr
                355                 360                 365

Gln Asp Glu Leu Thr Val Glu Gly Thr Arg Ala Asn Leu Thr Gly Trp
370                 375                 380

Asp Pro Gln Lys Asp Leu Ile Val Arg Val Cys Val Ser Asn Ala Val
385                 390                 395                 400

Gly Cys Gly Pro Trp Ser Gln Pro Leu Val Val Ser Ser His Asp Arg
                405                 410                 415

Ala Gly Gln Gln Gly Pro Pro His Ser Arg Thr Ser Trp Val Pro Val
                420                 425                 430

Val Leu Gly Val Leu Thr Ala Leu Val Thr Ala Ala Leu Ala Leu
            435                 440                 445

Ile Leu Leu Arg Lys Arg Arg Lys Glu Thr Arg Phe Gly Gln Ala Phe
450                 455                 460

Asp Ser Val Met Ala Arg Gly Glu Pro Ala Val His Phe Arg Ala Ala
465                 470                 475                 480

Arg Ser Phe Asn Arg Glu Arg Pro Glu Arg Ile Glu Ala Thr Leu Asp
                485                 490                 495

Ser Leu Gly Ile Ser Asp Glu Leu Lys Glu Lys Leu Glu Asp Val Leu
            500                 505                 510

Ile Pro Glu Gln Gln Phe Thr Leu Gly Arg Met Leu Gly Lys Gly Glu
            515                 520                 525

Phe Gly Ser Val Arg Glu Ala Gln Leu Lys Gln Glu Asp Gly Ser Phe
530                 535                 540

Val Lys Val Ala Val Lys Met Leu Lys Ala Asp Ile Ile Ala Ser Ser
545                 550                 555                 560

Asp Ile Glu Glu Phe Leu Arg Glu Ala Ala Cys Met Lys Glu Phe Asp
                565                 570                 575
```

-continued

```
His Pro His Val Ala Lys Leu Val Gly Val Ser Leu Arg Ser Arg Ala
            580                 585                 590

Lys Gly Arg Leu Pro Ile Pro Met Val Ile Leu Pro Phe Met Lys His
        595                 600                 605

Gly Asp Leu His Ala Phe Leu Leu Ala Ser Arg Ile Gly Glu Asn Pro
    610                 615                 620

Phe Asn Leu Pro Leu Gln Thr Leu Ile Arg Phe Met Val Asp Ile Ala
625                 630                 635                 640

Cys Gly Met Glu Tyr Leu Ser Ser Arg Asn Phe Ile His Arg Asp Leu
                645                 650                 655

Ala Ala Arg Asn Cys Met Leu Ala Glu Asp Met Thr Val Cys Val Ala
            660                 665                 670

Asp Phe Gly Leu Ser Arg Lys Ile Tyr Ser Gly Asp Tyr Tyr Arg Gln
        675                 680                 685

Gly Cys Ala Ser Lys Leu Pro Val Lys Trp Leu Ala Leu Glu Ser Leu
    690                 695                 700

Ala Asp Asn Leu Tyr Thr Val Gln Ser Asp Val Trp Ala Phe Gly Val
705                 710                 715                 720

Thr Met Trp Glu Ile Met Thr Arg Gly Gln Thr Pro Tyr Ala Gly Ile
                725                 730                 735

Glu Asn Ala Glu Ile Tyr Asn Tyr Leu Ile Gly Gly Asn Arg Leu Lys
            740                 745                 750

Gln Pro Pro Glu Cys Met Glu Asp Val Tyr Asp Leu Met Tyr Gln Cys
        755                 760                 765

Trp Ser Ala Asp Pro Lys Gln Arg Pro Ser Phe Thr Cys Leu Arg Met
    770                 775                 780

Glu Leu Glu Asn Ile Leu Gly Gln Leu Ser Val Leu Ser Ala Ser Gln
785                 790                 795                 800

Asp Pro Leu Tyr Ile Asn Ile Glu Arg Ala Glu Pro Thr Ala Gly
                805                 810                 815

Gly Ser Leu Glu Leu Pro Gly Arg Asp Gln Pro Tyr Ser Gly Ala Gly
            820                 825                 830

Asp Gly Ser Gly Met Gly Ala Val Gly Gly Thr Pro Ser Asp Cys Arg
        835                 840                 845

Tyr Ile Leu Thr Pro Gly Gly Leu Ala Glu Gln Pro Gly Gln Ala Glu
    850                 855                 860

His Gln Pro Glu Ser Pro Leu Asn Glu Thr Gln Arg Leu Leu Leu Leu
865                 870                 875                 880

Gln Gln Gly Leu Leu Pro His Ser Ser Cys
                885                 890
```

<210> SEQ ID NO 22
<211> LENGTH: 823
<212> TYPE: PRT
<213> ORGANISM: Homo sapiens

<400> SEQUENCE: 22

```
Met Lys Ile Asn Asn Glu Glu Ile Val Ser Asp Pro Ile Tyr Ile Glu
1               5                   10                  15

Val Gln Gly Leu Pro His Phe Thr Lys Gln Pro Glu Ser Met Asn Val
                20                  25                  30

Thr Arg Asn Thr Ala Phe Asn Leu Thr Cys Gln Ala Val Gly Pro Pro
            35                  40                  45

Glu Pro Val Asn Ile Phe Trp Val Gln Asn Ser Ser Arg Val Asn Glu
        50                  55                  60
```

```
Gln Pro Glu Lys Ser Pro Ser Val Leu Thr Val Pro Gly Leu Thr Glu
 65                  70                  75                  80

Met Ala Val Phe Ser Cys Glu Ala His Asn Asp Lys Gly Leu Thr Val
             85                  90                  95

Ser Lys Gly Val Gln Ile Asn Ile Lys Ala Ile Pro Ser Pro Pro Thr
            100                 105                 110

Glu Val Ser Ile Arg Asn Ser Thr Ala His Ser Ile Leu Ile Ser Trp
        115                 120                 125

Val Pro Gly Phe Asp Gly Tyr Ser Pro Phe Arg Asn Cys Ser Ile Gln
        130                 135                 140

Val Lys Glu Ala Asp Pro Leu Ser Asn Gly Ser Val Met Ile Phe Asn
145                 150                 155                 160

Thr Ser Ala Leu Pro His Leu Tyr Gln Ile Lys Gln Leu Gln Ala Leu
                165                 170                 175

Ala Asn Tyr Ser Ile Gly Val Ser Cys Met Asn Glu Ile Gly Trp Ser
            180                 185                 190

Ala Val Ser Pro Trp Ile Leu Ala Ser Thr Thr Glu Gly Ala Pro Ser
        195                 200                 205

Val Ala Pro Leu Asn Val Thr Val Phe Leu Asn Glu Ser Ser Asp Asn
        210                 215                 220

Val Asp Ile Arg Trp Met Lys Pro Pro Thr Lys Gln Gln Asp Gly Glu
225                 230                 235                 240

Leu Val Gly Tyr Arg Ile Ser His Val Trp Gln Ser Ala Gly Ile Ser
                245                 250                 255

Lys Glu Leu Leu Glu Glu Val Gly Gln Asn Gly Ser Arg Ala Arg Ile
            260                 265                 270

Ser Val Gln Val His Asn Ala Thr Cys Thr Val Arg Ile Ala Ala Val
        275                 280                 285

Thr Lys Gly Gly Val Gly Pro Phe Ser Asp Pro Val Lys Ile Phe Ile
        290                 295                 300

Pro Ala His Gly Trp Val Asp Tyr Ala Pro Ser Ser Thr Pro Ala Pro
305                 310                 315                 320

Gly Asn Ala Asp Pro Val Leu Ile Ile Phe Gly Cys Phe Cys Gly Phe
                325                 330                 335

Ile Leu Ile Gly Leu Val Leu Tyr Ile Ser Leu Ala Ile Arg Lys Arg
            340                 345                 350

Val Gln Glu Thr Lys Phe Gly Asn Ala Phe Thr Glu Glu Asp Ser Glu
        355                 360                 365

Leu Val Val Asn Tyr Ile Ala Lys Lys Ser Phe Cys Arg Arg Ala Ile
        370                 375                 380

Glu Leu Thr Leu His Ser Leu Gly Val Ser Glu Glu Leu Gln Asn Lys
385                 390                 395                 400

Leu Glu Asp Val Val Ile Asp Arg Asn Leu Leu Ile Leu Gly Lys Ile
                405                 410                 415

Leu Gly Glu Gly Glu Phe Gly Ser Val Met Glu Gly Asn Leu Lys Gln
            420                 425                 430

Glu Asp Gly Thr Ser Leu Lys Val Ala Val Lys Thr Met Lys Leu Asp
        435                 440                 445

Asn Ser Ser Gln Arg Glu Ile Glu Glu Phe Leu Ser Glu Ala Ala Cys
        450                 455                 460

Met Lys Asp Phe Ser His Pro Asn Val Ile Arg Leu Leu Gly Val Cys
465                 470                 475                 480
```

-continued

```
Ile Glu Met Ser Ser Gln Gly Ile Pro Lys Pro Met Val Ile Leu Pro
                485                 490                 495

Phe Met Lys Tyr Gly Asp Leu His Thr Tyr Leu Leu Tyr Ser Arg Leu
            500                 505                 510

Glu Thr Gly Pro Lys His Ile Pro Leu Gln Thr Leu Leu Lys Phe Met
        515                 520                 525

Val Asp Ile Ala Leu Gly Met Glu Tyr Leu Ser Asn Arg Asn Phe Leu
    530                 535                 540

His Arg Asp Leu Ala Ala Arg Asn Cys Met Leu Arg Asp Asp Met Thr
545                 550                 555                 560

Val Cys Val Ala Asp Phe Gly Leu Ser Lys Lys Ile Tyr Ser Gly Asp
                565                 570                 575

Tyr Tyr Arg Gln Gly Arg Ile Ala Lys Met Pro Val Lys Trp Ile Ala
            580                 585                 590

Ile Glu Ser Leu Ala Asp Arg Val Tyr Thr Ser Lys Ser Asp Val Trp
        595                 600                 605

Ala Phe Gly Val Thr Met Trp Glu Ile Ala Thr Arg Gly Met Thr Pro
    610                 615                 620

Tyr Pro Gly Val Gln Asn His Glu Met Tyr Asp Tyr Leu Leu His Gly
625                 630                 635                 640

His Arg Leu Lys Gln Pro Glu Asp Cys Leu Asp Glu Leu Tyr Glu Ile
                645                 650                 655

Met Tyr Ser Cys Trp Arg Thr Asp Pro Leu Asp Arg Pro Thr Phe Ser
            660                 665                 670

Val Leu Arg Leu Gln Leu Glu Lys Leu Leu Glu Ser Leu Pro Asp Val
        675                 680                 685

Arg Asn Gln Ala Asp Val Ile Tyr Val Asn Thr Gln Leu Leu Glu Ser
690                 695                 700

Ser Glu Gly Leu Ala Gln Gly Ser Thr Leu Ala Pro Leu Asp Leu Asn
705                 710                 715                 720

Ile Asp Pro Asp Ser Ile Ile Ala Ser Cys Thr Pro Arg Ala Ala Ile
                725                 730                 735

Ser Val Val Thr Ala Glu Val His Asp Ser Lys Pro His Glu Gly Arg
            740                 745                 750

Tyr Ile Leu Asn Gly Gly Ser Glu Glu Trp Glu Asp Leu Thr Ser Ala
        755                 760                 765

Pro Ser Ala Ala Val Thr Ala Glu Lys Asn Ser Val Leu Pro Gly Glu
    770                 775                 780

Arg Leu Val Arg Asn Gly Val Ser Trp Ser His Ser Ser Met Leu Pro
785                 790                 795                 800

Leu Gly Ser Ser Leu Pro Asp Glu Leu Leu Phe Ala Asp Asp Ser Ser
                805                 810                 815

Glu Gly Ser Glu Val Leu Met
            820
```